United States Patent
Pati et al.

(10) Patent No.: US 6,200,812 B1
(45) Date of Patent: *Mar. 13, 2001

(54) SEQUENCE ALTERATIONS USING HOMOLOGOUS RECOMBINATION

(75) Inventors: Sushma Pati, Redwood City; David A. Zarling, Menlo Park, both of CA (US)

(73) Assignee: SRI International, Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/288,586

(22) Filed: Apr. 8, 1999

Related U.S. Application Data

(63) Continuation of application No. 08/910,367, filed on Aug. 13, 1997, now Pat. No. 5,948,653.
(60) Provisional application No. 60/041,173, filed on Mar. 21, 1997.

(51) Int. Cl.[7] ................................................. C12N 15/63
(52) U.S. Cl. ........................ 435/463; 435/455; 435/471
(58) Field of Search .................................. 435/91.1, 455, 435/463, 471; 530/350; 536/23.1

(56) References Cited

U.S. PATENT DOCUMENTS

| | | | |
|---|---|---|---|
| 4,873,191 | 10/1989 | Wagner et al. | 800/25 |
| 4,888,274 | 12/1989 | Radding et al. | 435/6 |
| 4,950,509 | 8/1990 | Bertling | 435/456 |
| 5,223,414 | 6/1993 | Zarling et al. | 435/91.2 |
| 5,264,618 | 11/1993 | Felgner et al. | 560/224 |
| 5,272,071 | 12/1993 | Chappel | 435/6 |
| 5,273,881 | 12/1993 | Sena et al. | 425/6 |
| 5,416,260 | 5/1995 | Koller et al. | 800/2 |
| 5,451,513 | 9/1995 | Maliga et al. | 800/278 |
| 5,459,072 | 10/1995 | McKay et al. | 435/320.1 |
| 5,460,941 | 10/1995 | Camerini-Otero et al. | 435/6 |
| 5,464,764 | 11/1995 | Capecchi et al. | 435/6 |
| 5,506,098 | 4/1996 | Zarling et al. | 435/6 |
| 5,527,674 | 6/1996 | Guerra et al. | 435/6 |
| 5,565,350 | 10/1996 | Kmiec | 435/463 |
| 5,571,688 | 11/1996 | Mekalanos et al. | 435/29 |
| 5,578,461 | 11/1996 | Sherwin et al. | 435/69.1 |
| 5,580,734 | 12/1996 | Treco et al. | 435/6 |
| 5,589,369 | 12/1996 | Seidman et al. | 435/6 |
| 5,948,653 | * 9/1999 | Pati et al. | 435/6 |

FOREIGN PATENT DOCUMENTS

| | | |
|---|---|---|
| 0 718 404 | 6/1996 | (EP). |
| 91/17267 | 11/1991 | (WO). |
| 91/19796 | 12/1991 | (WO). |
| 92/08791 | 5/1992 | (WO). |
| 92/15694 | 9/1992 | (WO). |
| 92/20808 | 11/1992 | (WO). |
| 93/03736 | 3/1993 | (WO). |
| 93/05177 | 3/1993 | (WO). |
| 93/05178 | 3/1993 | (WO). |
| 93/22443 | 11/1993 | (WO). |
| 94/04032 | 3/1994 | (WO). |
| 95/22625 | 8/1995 | (WO). |
| 96/40765 | 12/1996 | (WO). |
| 97/04111 | 2/1997 | (WO). |
| 97/05268 | 2/1997 | (WO). |

OTHER PUBLICATIONS

Gates, C.M., et al., "Affinity Selective Isolation of Ligands from Peptide Libraries Through Display on a lac Repressor "Headpiece Dimer"", *J. Mol. Biol.*, 255:373–386 (1996).

Rashid, N., et al., "Characterization of a RecA/RAD51 homologue from the hyperthermophilic archaeon *pyrococcus* sp. KOD1", *Nucleic Acids Research*, vol. 25, No. 4:719–726 (1997).

Jayasena, V.K., et al., "Complement–stabilized D–loop—RecA–catalyzed Stable Pairing of Linear DNA Molecules at Internal Sites", *J. Mol. Biol.*, 230:1015–1024 (1993).

Crameri, A., et al., "Construction and evolution of antibody–phage libraries by DNA shuffling", *Nature Medicine*, vol. 2, No. 1:100–102 (Jan. 1996).

Cole–Strauss, A., et al., "Correction of the Mutation Responsible for Sickle Cell Anemia by an RNA–DNA Oligonucleotide", *Science*, vol. 273:1386–1389 (Sep. 1996).

Matsumura, I., et al., "DNA Shuffling brightens prospects for GFP", *Nature Bio Tech.*, vol. 14:366 (Mar. 1996).

Stemmer, W.P.C., "DNA shuffling by random fragmentation and reassembly: In vitro recombination for molecular evolution", *Proc. Natl. Acad. Sci. USA*, vol. 91:10747–10751 (Oct. 1994).

Meyer Jr., R.B., et al., "Efficient, Specific Cross–Linking and Cleavage of DNA by Stable, Synthetic Complementary Oligodeoxynucleotides", *J. of the Amer. Chem. Soc.*, 111(22):8517–8519 (1989).

(List continued on next page.)

Primary Examiner—Robert A. Schwartzman
(74) Attorney, Agent, or Firm—Richard F. Trecartin; Flehr Hohbach Test Albritton & Herbert LLP

(57) ABSTRACT

The invention relates to methods for targeting an exogenous polynucleotide or exogenous complementary polynucleotide pair to a predetermined endogenous DNA target sequence in a target cell by homologous pairing, particularly for altering an endogenous DNA sequence, such as a chromosomal DNA sequence, typically by targeted homologous recombination. In certain embodiments, the invention relates to methods for targeting an exogenous polynucleotide having a linked chemical substituent to a predetermined endogenous DNA sequence in a metabolically active target cell, generating a DNA sequence-specific targeting of one or more chemical substituents in an intact nucleus of a metabolically active target cell, generally for purposes of altering a predetermined endogenous DNA sequence in the cell. The invention also relates to compositions that contain exogenous targeting polynucleotides, complementary pairs of exogenous targeting polynucleotides, chemical substituents of such polynucleotides, and recombinase proteins used in the methods of the invention.

39 Claims, 24 Drawing Sheets

OTHER PUBLICATIONS

Kido, M., et al., "*Escherichia coli* RecA Protein Modified with a Nuclear Location Signal Binds to Chromosomes in Living Mammalian Cells", *Exper. Cell Res.*, 198:107–114 (1992).

Woo, J., et al., "G/C–modified oligodeoxynucleotides with selective complementarity: synthesis and hybridization properties", *Nucleic Acids Res.*, 24(13):2470–2475 (1996).

Kowalczykowski, S.C., et al., "Homologous Recombination Proteins and their Potential Applications in Gene Targeting Technology," *Gene Targeting*, CRC Press: Boca Raton, ed. Manuel A. Vega, Chap. 7:167–210 (1995).

Kunzelmann, K., et al., "Gene targeting of CFTR DNA in CF epithelial cells", *Gene Therapy*, 3:859–867 (1996).

Voloshin, O.N., et al., "Homologous DNA pairing promoted by a 20 amino acid peptide derived from RecA", *Science*, 272:868–872 (1996).

Revet, B.M.J., et al., "Homologous DNA Targeting with RecA Protein–coated Short DNA Probes and Electron Microscope Mapping on Linear Duplex Molecules", rep. fr. *J. Mol. Biol.*, 232:779–791 (1993).

Camerini–Otero, R.D., et al., "Homologous Recombination Proteins in Prokaryotes and Eukaroyotes", *Annu. Rev. Genetics*, 29:509–52 (1995).

Crameri, A., et al., "Improved Green Fluorescent Protein by Molecular Evolution Using DNA Shuffling", *Nature BioTech.*, 14:315–319 (Mar. 1996).

Kutyavin, I.V., et al., "Oligonucleotides Containing 2–Aminoadenine and 2–Thiothymine Act as Selectively Binding Complementary Agents", *Biochemistry*, 35:11170–11176 (1996).

Herzing, L.B.K., et al., "Novel lacZ–based recombination vectors for mammalian cells", *Gene*, 137:163–169 (1993).

Stemmer, W.P.C., "Rapid evolution of a protein in vitro by DNA shuffling", *Nature*, 370:389–391 (Aug. 1994).

Reiss, B., et al., "RecA protein stimulates homologous recombination in plants", *Proc. Natl. Acad. Sci. USA*, 93:3094–3098 (Apr. 1996).

Podyminogin, M.A., et al., "RecA–Catalyzed, Sequence–Specific Alkylation of DNA by Cross–Linking Oligonucleotides. Effects of Length and Nonhomologous Base Substitutions", *Biochemistry*, 35:7267–7274 (1996).

Bertolotti, R., "Recombinase–mediated Gene Therapy", *Bionews*, Newsletter of BioTechnology, Health and Environmental Sciences, N14 (Nov. 1996).

Afonina, I., et al., "Sequence–specific arrest of primer extension on single–stranded DNA by an oligonucleotide–minor groove binder conjugate", *Proc. Natl. Acad. Sci. USA*, 93:3199–3204 (Apr. 1996).

Podyminogin, M.A., et al., "Sequence–Specific Covalent Modification of DNA by Cross–Linking Oligonucleotides. Catalysis by RecA and Implication for the Mechanism of Synaptic Joint Formation", *Biochemistry*, 34:13098–13108 (1995).

Pati, W., et al., "Sequence–Specific DNA Targeting", *Encyclo. of Cancer*, vol. III:1601–1625 (1997).

Fu, D., et al., "Sequence double–stranded DNA by strand displacement", *Nucleic Acids Res.*, 25(3):677–679 (1997).

Hunger–Bertling, K., et al., "Short DNA fragments induce site specific recombination in mammalian cells", *Mol. and Cellular Biochem.*, 92:107–116 (1990).

Stemmer, W.P.C., et al., "Single–step assembly of a gene and entire plasmid from large numbers of oligodeoxyribonucleotides", *Gene*, 164:49–53 (1995).

Ludwig, D.L., et al., "Spontaneous and Induced Homologous Recombination Between lacZ Chromosomal Direct Repeats in CV–1 Cells", *Somane Cell and Molecular Genetics*, 20(1):11–25 (1994).

Yoon, K., et al., "Targeted gene correction of episomal DNA in mammalian cells mediated by a chimeric RNA–DNA oligonucleotide", *Proc. Natl. Acad. Sci. USA*, 93:2071–2076 (Mar. 1996).

Jasin, M., et al., "Targeted transgenesis", *Proc. Natl. Acad. Sci. USA*, 93:8804–8808 (Aug. 1996).

Rawls, R., "Hybrid DNA–RNA efficiently repairs gene", *C&EN*, p. 11 (Sep. 1996).

Sena, E.P., et al., "Targeting in linear DNA duplexes with two complementary probe strands for hybrid stability", *Nature Genetics*, 3:365–372 (Apr. 1993).

Lukhtanov, E.A. et al., "Rapid and Efficient Hybridization–Triggered Crosslinking within a DNA Duplex by an Oligodeoxyribonucleotide Bearing a Conjugated Cyclopropapyrroloindole," *Nucleic Acids Research*, 24(4):683–687 (1996).

Tabone, J.C. et al., "Factors Influencing the Extent and Regiospecificity of Cross–Link Formation between Single–Stranded DNA and Reactive Complementary Oligodeoxynucleotides," *Biochemistry*, 33(1):375–383 (1994).

Bertling, "Transfection of a DNA/Protein Complex into Nuclei of Mammalian Cells Using Polyoma Capsids and Electroporation," *Bioscience Reports*, 7:107–111 (1987).

Ausubel et al., "Short Protocols in Molecular Biology," 2n ed. (John Wiley & Sons: New York), pp. 9–14 and 9–15 (1992).

Wu et al., "Targeting Genes: Delivery and Persistent Expression of a Foreign Gene Driven by Mammalian Regulatory Elements in Vivo," *The Journal of Biological Chemistry*, 264(29):16985–16987 (1989).

Felgner et al. "Lipofection: A Highly Efficient, Lipid–Mediated DNA–Transfection Procedure," *Proc. Natl. Acad. Sci. USA*, 84:7413–7417 (1987).

Drumm et al., "Correction of the Cystic Fibrosis Defect In Vitro by Retrovirus–Mediated Gene Transfer," *Cell*, 62:1227–1233 (1990).

Fields and Jang, "Presence of a Potent Transcription Activating Sequence in the p53 Protein," *Science*, 249:1046–1049 (1990).

Valancius and Smithies, "Testing and "In–Out" Targeting Procedure for Making Subtle Genomic Modifications in Mouse Embryonic Stem Cells," *Molecular and Cellular Biology*, 11(3):1402–1408 (1991).

Cox et al., "Enzymes of General Recombination," *Ann. Rev. Biochem.*, 56:229–262 (1987).

Sauer and Henderson, "Targeted Insertion of Exogenous DNA into the Eukaryotic Genome by the Cre Recombinase," *New Biologist*, 2:441–449 (1990).

Dunderdale et al., "Formation and Resolution of Recombination Intermediates by *E. coli* RecA and RuvC Proteins," *Nature*, 354(19):506–510 (1991).

Cheng et al., "RecA–Directed Hybridization of Psoralen–Monoadducted DNA Oligonucleotides to Duplex Targets," *NATO ASI Ser., Ser C., Photochemical Probes in Biochemistry*, 272:169–177, P.E. Nielsen (ed.), (1989).

Langer et al., "Enzymatic Synthesis of Biotin–Labeled Polynucleotides: Novel Nucleic Acid Affinity Probes," *Proc. Natl. Acad. Sci. USA*, 78(11):6633–6637 (1981).

Orkin et al., "Report and Recommendations of the Panel to Assess the NIH Investment in Research on Gene Therapy," *National Institutes of Health*, Dec. 7, 1995.

Thomas et al., "High Frequency Targeting of Genes to Specific Sites in the Mammalian Genome," *Cell*, 44:419–428 (1986).

Smithies et al., "Insertion of DNA Sequences into the Human Chromosomal β–Globin Locus by Homologous Recombination," *Nature*, 317:230–234 (1985).

Hasty et al., "Introduction of a Subtle Mutation into the Hox–2.6 Locus in Embryonic Stem Cells," *Nature*, 350:243–246 (1991).

Sauer et al., "Cre–stimulated recombination at loxP–containing DNA sequences placed into the mammalian genome," Nucleic Acids Research, 17(1):147–161 (1989).

O'Gorman et al., "Recombinase–mediated gene activation and site specific intergration in mannalian cells," *Science*, 251(15):1351–1355 (1991).

Matxuzaki et al., "Chromosome engeneering in Saccharomyces cerevisiae by using a site–specific recombination system of a yeast plasmid," J. Bacteriol., 172(2):610–618 (1990).

Wilson et al., "Hepatocyte–directed gene transfer in vivo leads to transient improvement of hypercholesteromia in low density lipoprotein receptor–defecient rabbits," J. Biol. Chem., 267(2):963–967 (1992).

Onouchi et al. "Operation of an efficient site–specific recombination system of Zygosaccharomyces rouxii in tobacco cells," Nucleic Acids Res., 19(23): 6373–6378 (1991).

Radding, C.M. "Homologous pairing and strand exchange in genetic recombination," *Ann. Rev. Genet.* 16: 405–37 (1982).

Hsieh et al. "Pairing of homologous DNA sequences by proteins: evidence for three–stranded DNA," *Genes and Development* 4: 1951–1963 (1990).

Rao et al., "Stable three–stranded DNA made by RecA protein," PNAS 88:2984–2988 (1991).

Holliday, R. "A mechanism for gene conversion in fungi," (1964) *Genet. Res.* 5: 282–304 (1964).

Lopez et al. "Homologous recombination intermediates between two duplex DNA catalysed by human cell extracts," *Nucleic Acids Res.* 15: 5643–5655 (1987).

Bardwell, "The mutagenic and carcinogenic effects of gene transfer," *Mutagenesis* 4: 245–253 (1989).

Capecchi, "Altering the genome by Homologous Recombination," *Science* 244: 1288–1292 (1989).

Joyner et al., "Production of a mutation in mouse En–2 gene by homologous recombination in embryonic stem cells," *Nature* 338: 153–156 (1989).

Mansour et al., "Disruption of the proto–oncogene int–2 in mouse embryo–derived stem cells: a general strategy for targeting mutations to non–selectable genes," *Nature* 336: 348–352 (1988).

Jasin and Berg, "Homologous integration in mammalian cells without target selection," *Genes and Development* 2: 1353–1363 (1988).

Doetschman et al. "Targeted mutation of the Hprt gene in mouse embryonic stem cess," (1988) *Proc. Natl. Acad. Sci. (U.S.A.)* 85: 8583–8587.

Dorin et al., "Selection for Precise chromosomal Targeting of a Dominant Marker by Homoolgous Recombination," (1989) *Science* 243: 1357–1360.

Itzhaki and Porter, "Targeted disruption of a human interferon–inducible gene detected by secretion of human growth hormone," (1991) *Nucl. Acids Res.* 19(14): 3835–3842.

Valancius and Smithies Testing an "In–Out" targeting procedure for making subtle genomic modification in Mouse Embryonic Stem Cells, (1991) *Molec. Cellular Biol.* 11: 1402–1408.

Reid et al., "Cotransformation and gene targeting in mouse embryonic stem cells," (1991) *Molec. Cellular Biol.* 11(5): 2769–2777.

Kucherlapati et al. "Homologous recombination between plasmids in mammalian can be enhanced by treatment of input DNA," (1984) *Proc. Natl. Acad. Sci. (U.S.A.)* 81: 3153–3157.

Smithies, O. "Insertion of DNA sequences into the human chromosomal β–globin locus by homologous recombination," (1985) *Nature* 317: 230–234.

Song et al. "Accurate modification of a chromosomal plasmid by homologous recombination in human cells," (1987) *Proc. Natl. Acad. Sci. (U.S.A.)* 84: 6820–6824.

Doetschman et al. "Targetted correction of a mutant HPRT gene in mouse embryonic stem cells," (1987) *Nature* 330: 576.–578.

Kim and Smithies "Recombinant fragment assay for gene targetting based on the polymerase chain reaction," (1988) *Nucleic Acids Res.* 16: 8887–8903.

Shesely et al. "Correction of a human $\beta^s$–globin gene by gene targeting," (1991) *Proc. Natl. Acad. Sci. (U.S.A.)* 88: 4294–4298.

Kim et al. "Problems encountered in detecting a targeted gene by the polymerase chain reaction," (1991) *Gene* 103: 227–233.

Koller et al. "Toward an animal model of cystic fibrosis: Targeted interruption of exon 10 of the cystic fibrosis transmembrane regulator in embryonic stem cells," (1991) *Proc. Natl. Acad. Sci. (U.S.A.)*, 88: 10730–10734.

Snouwaert et al. "An animal model for cystic fibrosis made by gene targeting," (1992) *Science* 257: 1083–1088.

Madiraju et al. "Properties of a mutant recA–encoded protein reveal a possible role for Escherichia coli recF–encoded protein in genetic recombination," (1988) *Proc. Natl. Acad. Sci. (U.S.A.)* 85: 6592–6596.

McCarthy et al. "Sensitive homologous recombination strand–transfer assay: Partial purification of a Drosophila melanogaster enzyme and detection of sequence effects on the strand–transfer activity of RecA protein," (1988) *Proc. Natl. Acad. Sci. (U.S.A.)* 85: 5854–5858.

Hsieh and Camerini–Otero "Formation of joint DNA molecules by two eukaryotic strand exchange proteins does not require melting of a DNA duplex," (1989) *J. Biol. Chem.* 264: 5089–5097.

Howard–Flanders et al. "Role of RecA protein spiral filaments in genetic recombination," (1984) *Nature* 309: 215–220.

Stasiak et al. Visualization of RecA–DNA complexes involved in consecutive stages of an in vitro strand exchange reaction, (1984) Cold Spring Harbor Symp. Quant. Biol. 49: 561–570.

Register et al. "Electron microscopic visualization of the RecA protein–mediated pairing and branch migration phases of DNA stand exchange," (1987) *J. Biol. Chem.* 262: 12812–12820.

Cheng et al. "Use of psoralen–modified oligonucleotides to trap three–stranded RecA–DNA complexes and repair of these cross–linked complexes and repair of these cross–linked complexes by ABC excinuclease," (1988) *J. Biol. Chem.* 263: 15110–15117.

Ferrin and Camerini–Otero "Selective cleavage of human DNA: RecA–assisted Restriction Endonuclease (RARE) cleavage," (1991) *Science* 354: 1494–1497.

Ramdas et al. "RecA protein promoted homologous pairing in vitro," (1989) *J. Biol Chem.* 264: 17395–17400.

Strobel et al. "Site–specific cleavage of human chromosome 4 mediated by triple–helix formation," (1991) *Science* 254: 1639–1642.

Rigas et al. "Rapid plasmid library screening using RecA–coated biotinylated probes," (1986) *Proc. Natl. Acad. Sci. (U.S.A.)* 83: 9591–9595.

* cited by examiner-

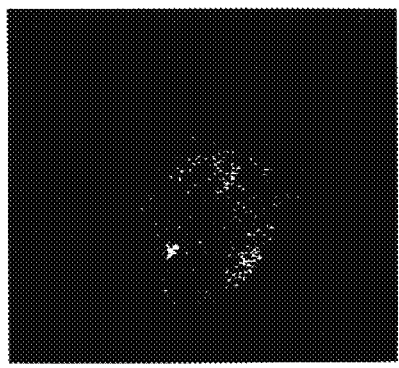 FIG._1A
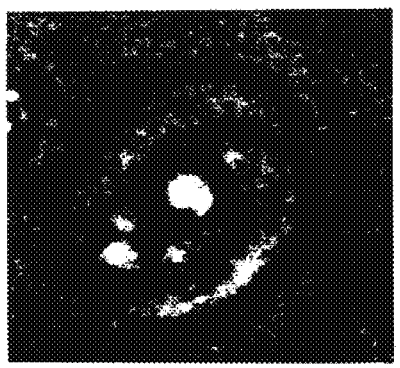 FIG._1B
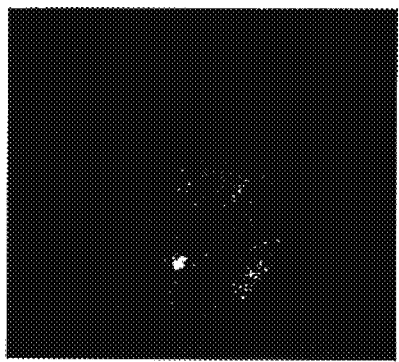 FIG._1C
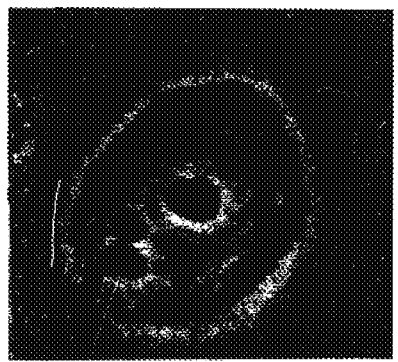 FIG._1D

FIG. 2A
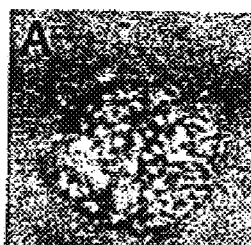
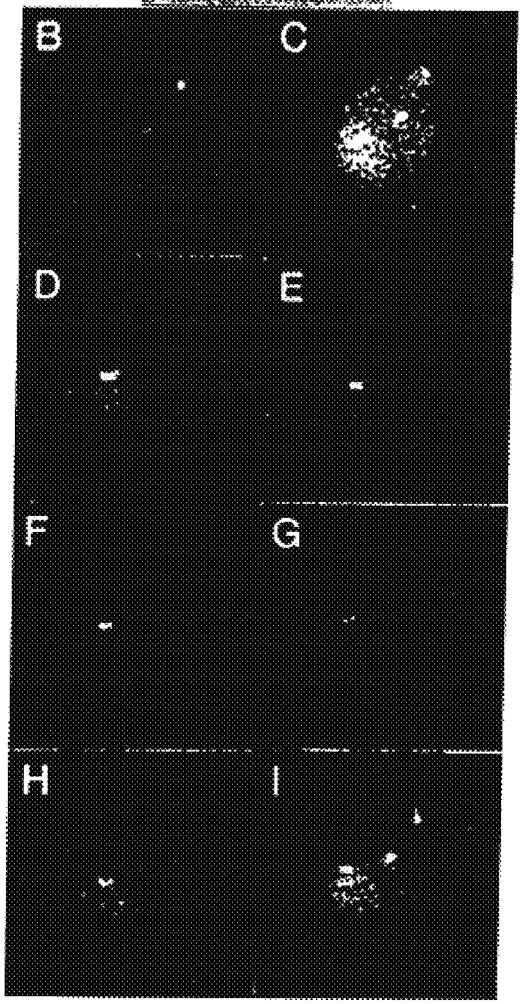
FIG. 2B　　　　　　　　　　　　FIG. 2C
FIG. 2D　　　　　　　　　　　　FIG. 2E
FIG. 2F　　　　　　　　　　　　FIG. 2G
FIG. 2H　　　　　　　　　　　　FIG. 2I
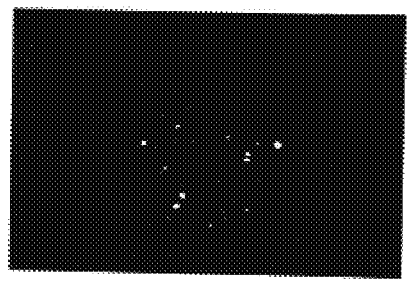
FIG. 2K
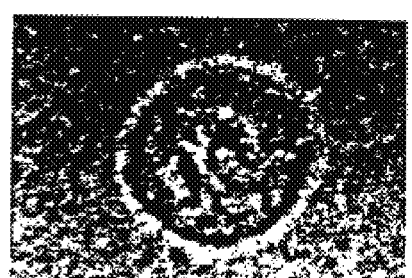
FIG. 2L

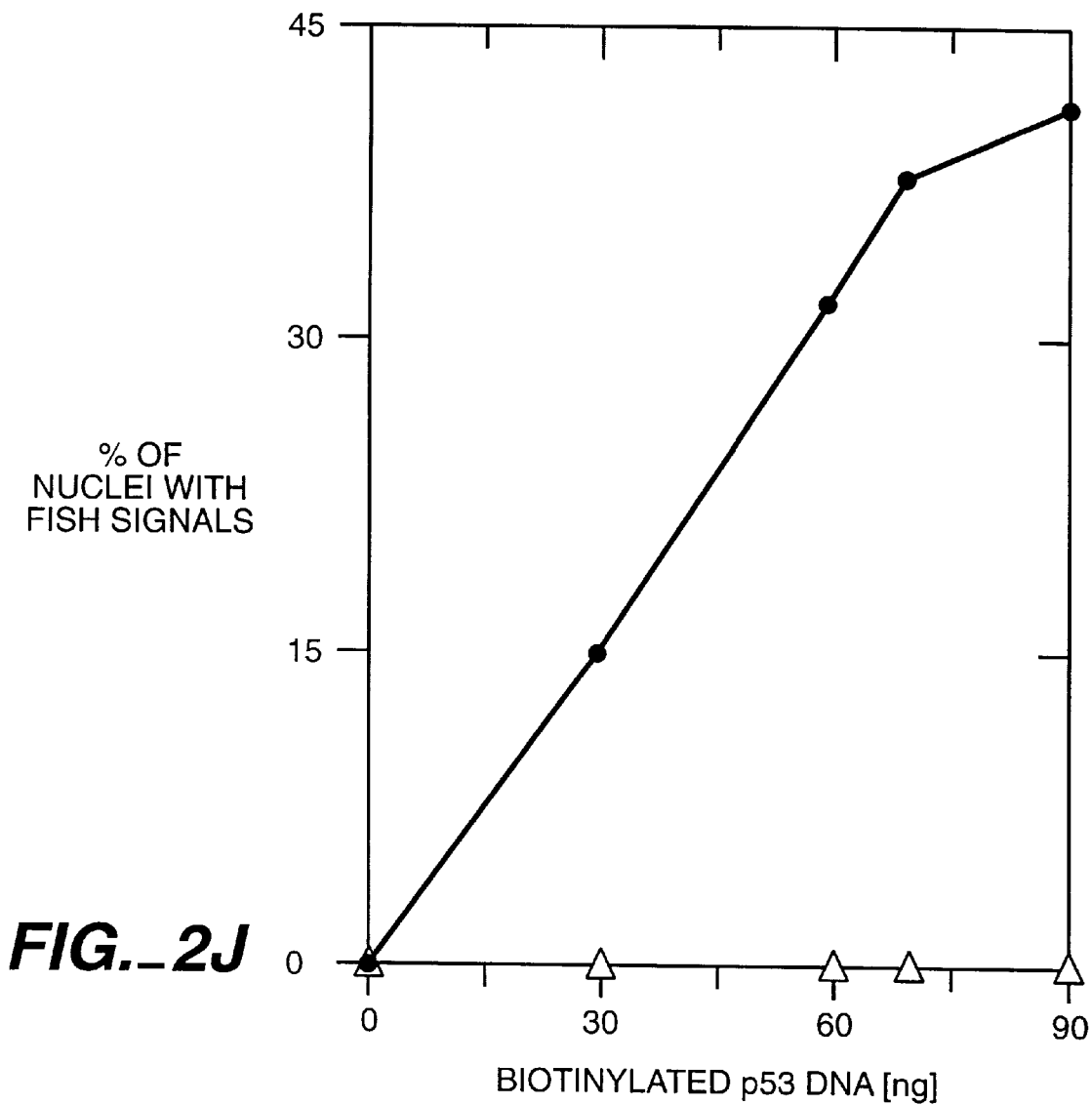

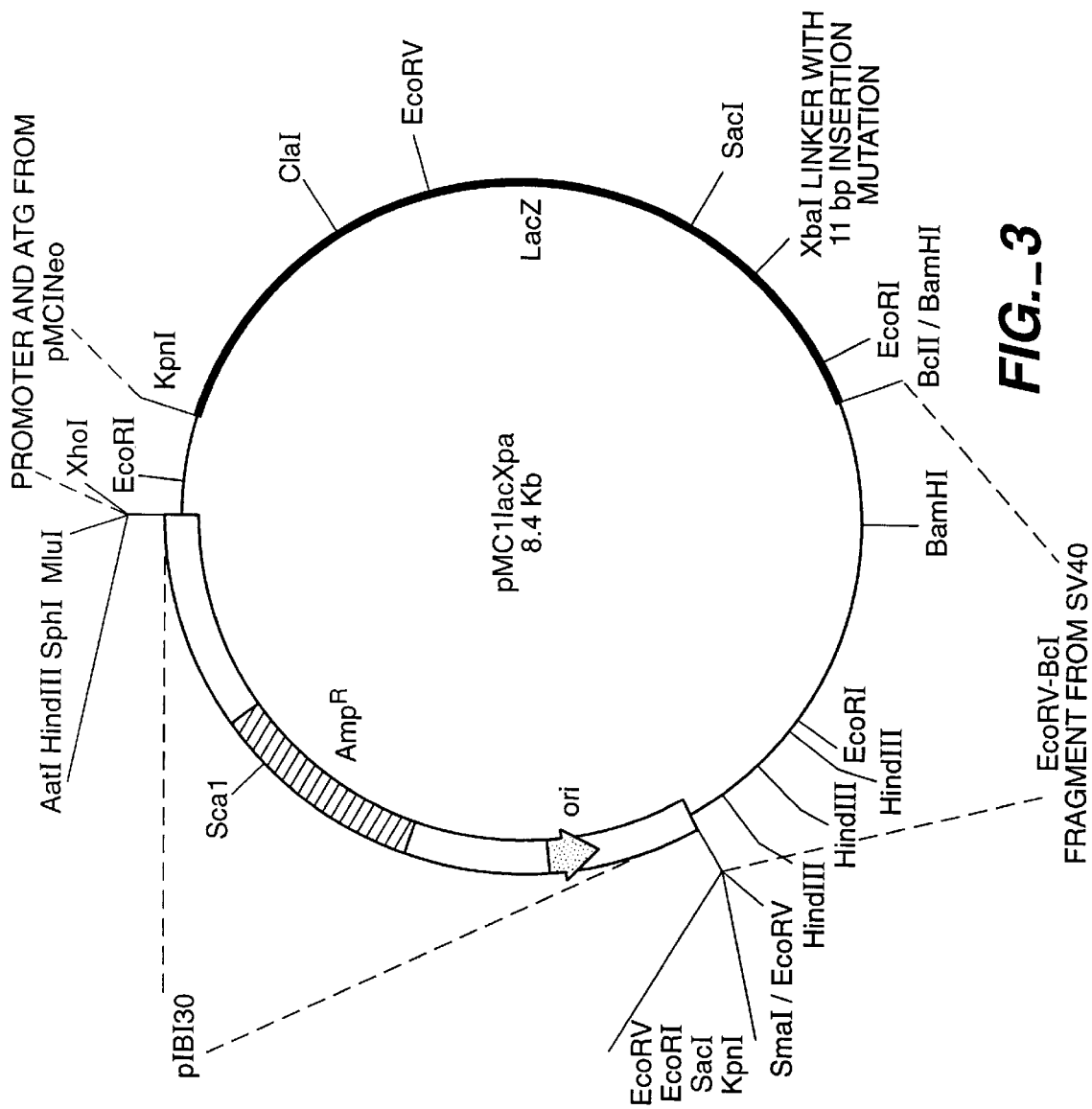
FIG._3

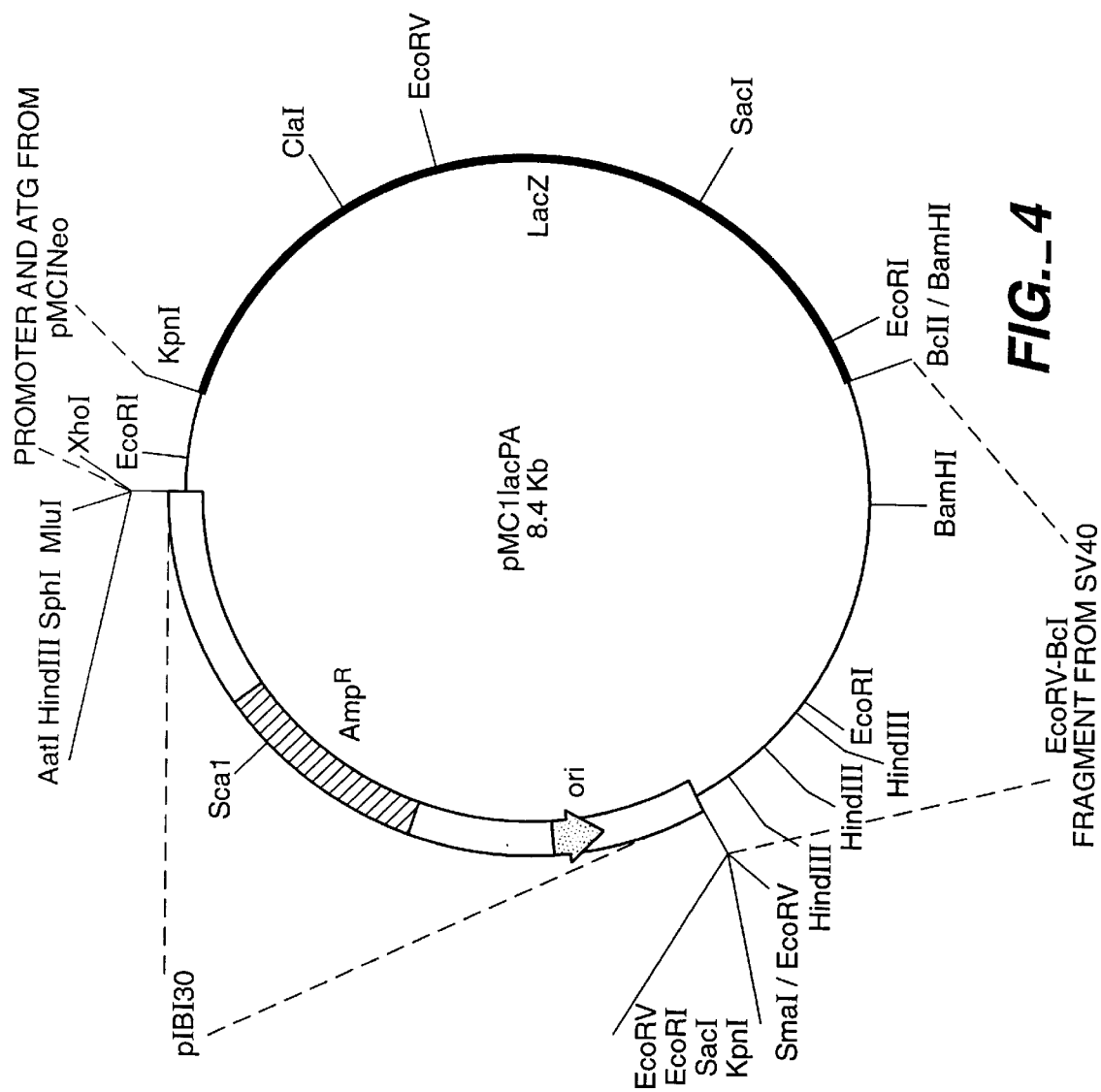
FIG._4

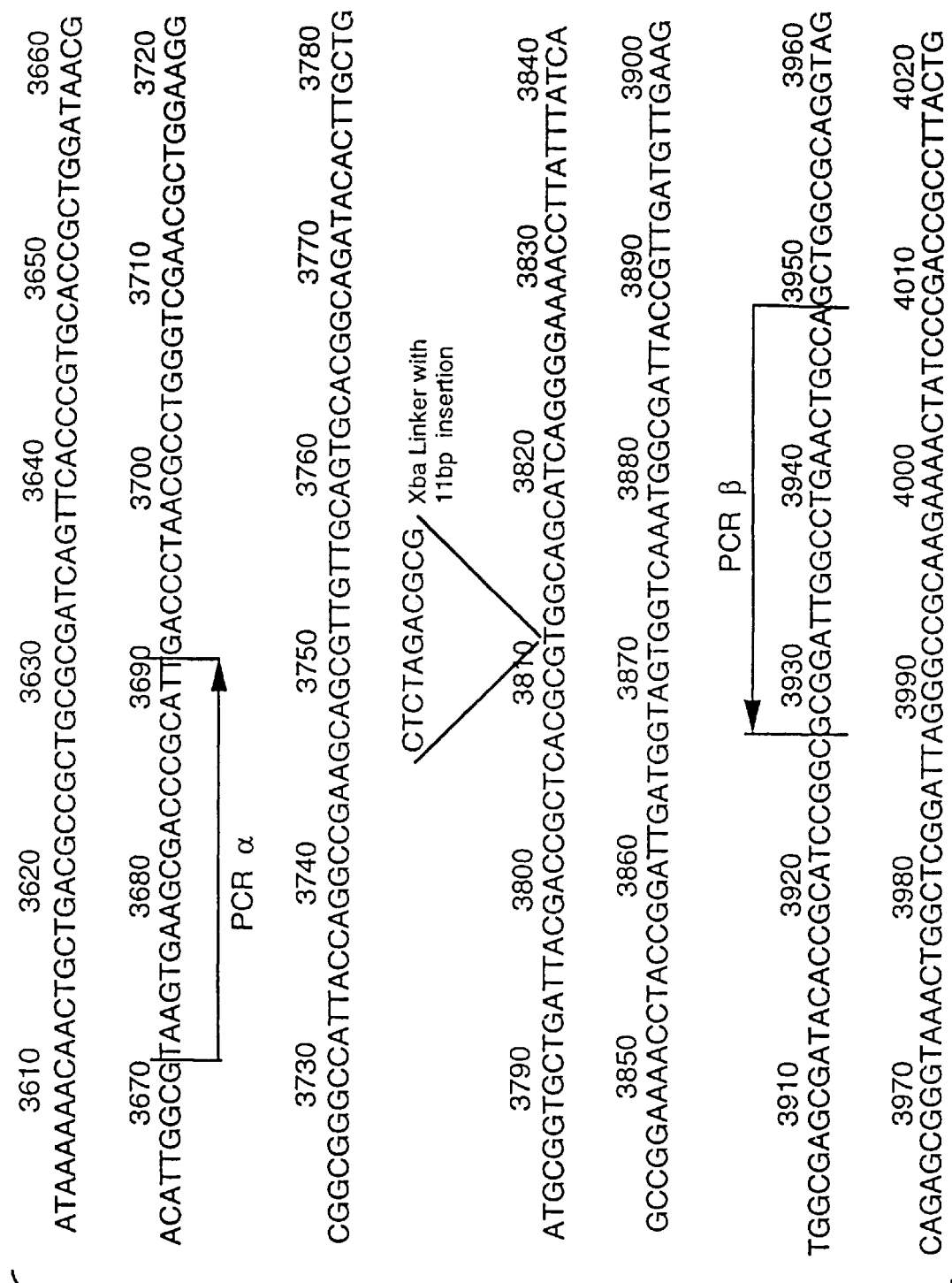
FIG._5

| EXPERIMENTAL SAMPLE | INJECTED PLASMID, 276-mer DNA AND RecA PROTEIN | | NUMBER OF INJECTED SURVIVING CELLS | NUMBER OF SURVIVING CELLS SCORING BLUE | SURVIVING CELLS SCORING BLUE (%) |
|---|---|---|---|---|---|
| 1 | pSV-β-gal | −276-mer − RecA | 168 | 21 | 12.5 |
| 2 | pMC1lacpa | −276-mer − RecA | 98 | 9 | 9.2 |
| 3 | pMC1lacXpa | −276-mer − RecA | 173 | 0 | 0 |
| 4 | pMC1lacXpa | +276-mer − RecA | 103 | 0 | 0 |
| 5 | pMC1lacXpa | +276-mer + RecA | 168 | 6 | 3.6 |

FIG._6

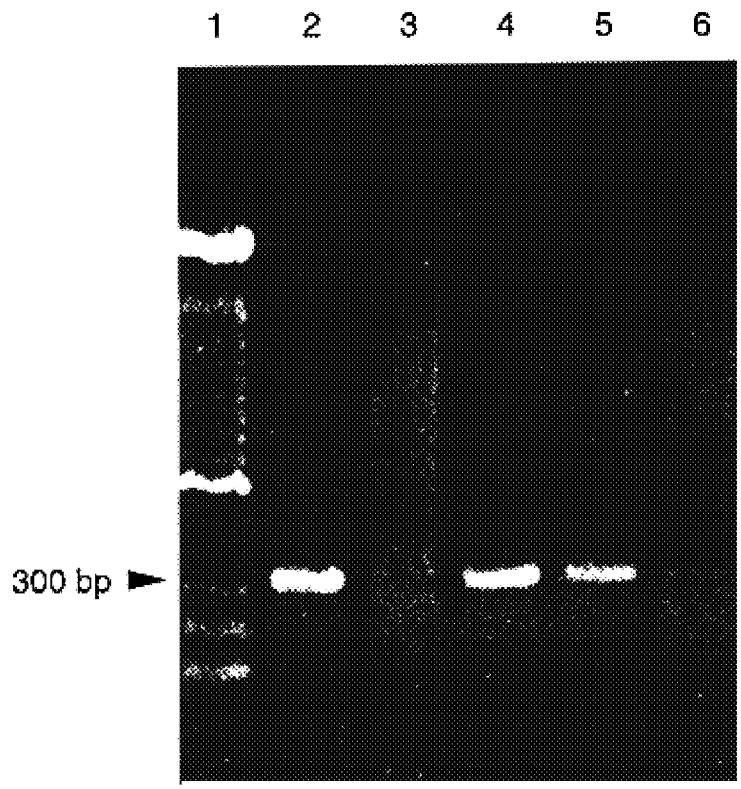
FIG._8A
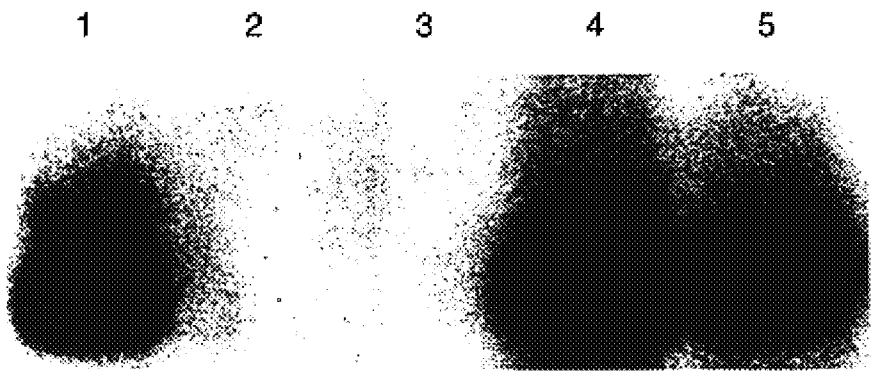
FIG._8B

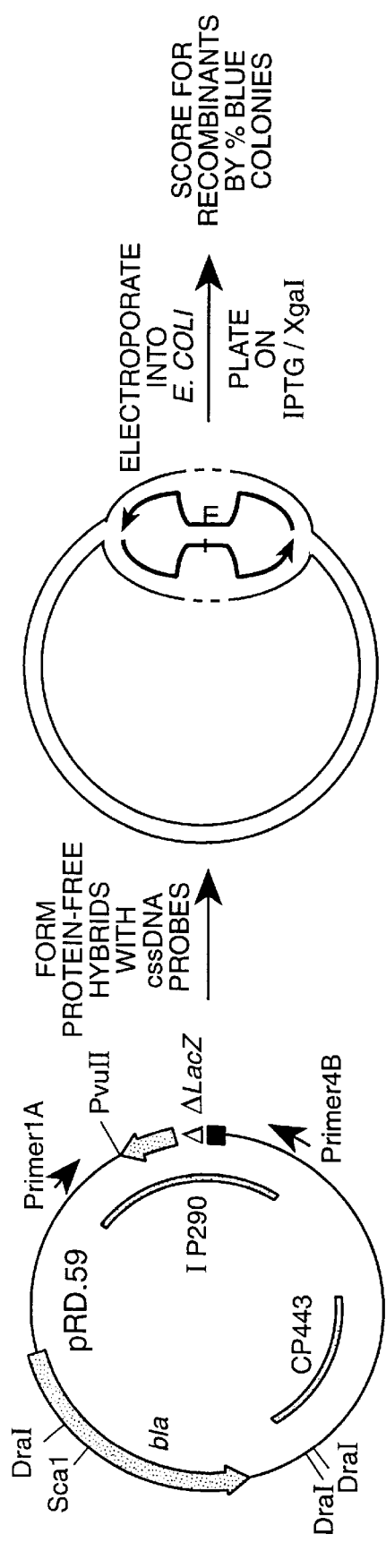
FIG._10
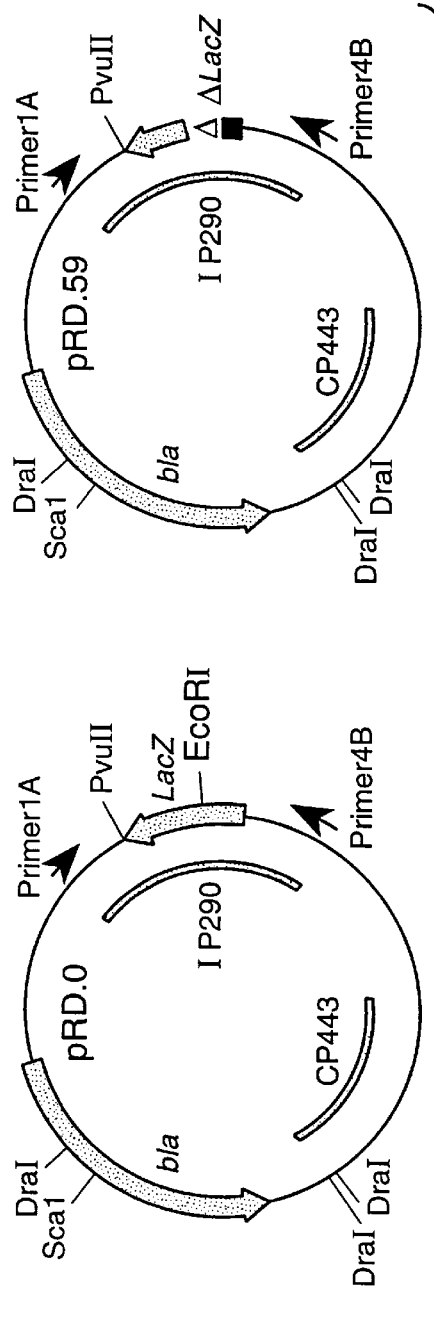
FIG._14A

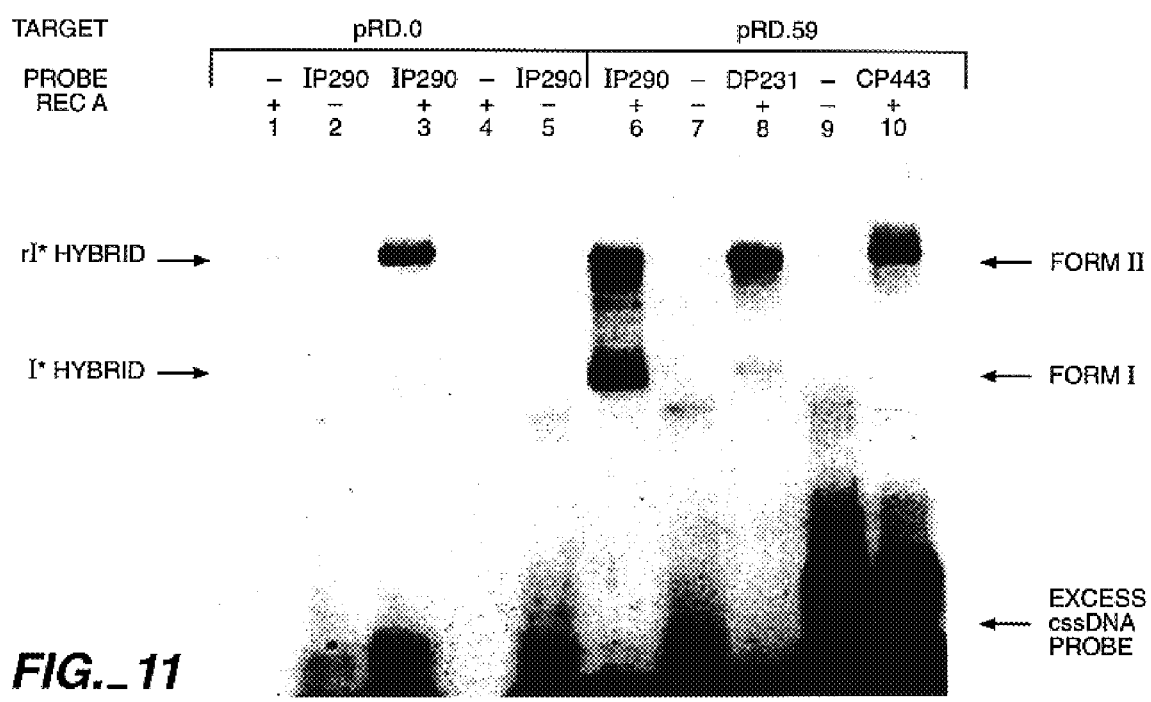
FIG._11

| TARGET | PROBE | RecA COATING | HOST | % RECOMBINANT / TOTAL COLONIES |
|---|---|---|---|---|
| pRD.59 | – | + | RecA+ | 0 |
|  | – | + | RecA– | 0 |
| pRD.59 | IP290 | – | RecA+ | 0 |
|  | IP290 | – | RecA– | 0 |
| pRD.59 | IP290 | + | RecA+ | 3 |
|  | IP290 | + | RecA– | 0 |
| pRD.59 | DP290 | – | RecA+ | 0 |
|  | DP290 | – | RecA– | 0 |
| pRD.59 | DP290 | + | RecA+ | 0 |
|  | DP290 | + | RecA– | 0 |
| pRD.59 | CP443 | – | RecA+ | 0 |
|  | CP443 | – | RecA– | 0 |
| pRD.59 | CP443 | + | RecA+ | 0 |
|  | CP443 | + | RecA– | 0 |
*FIG._12*
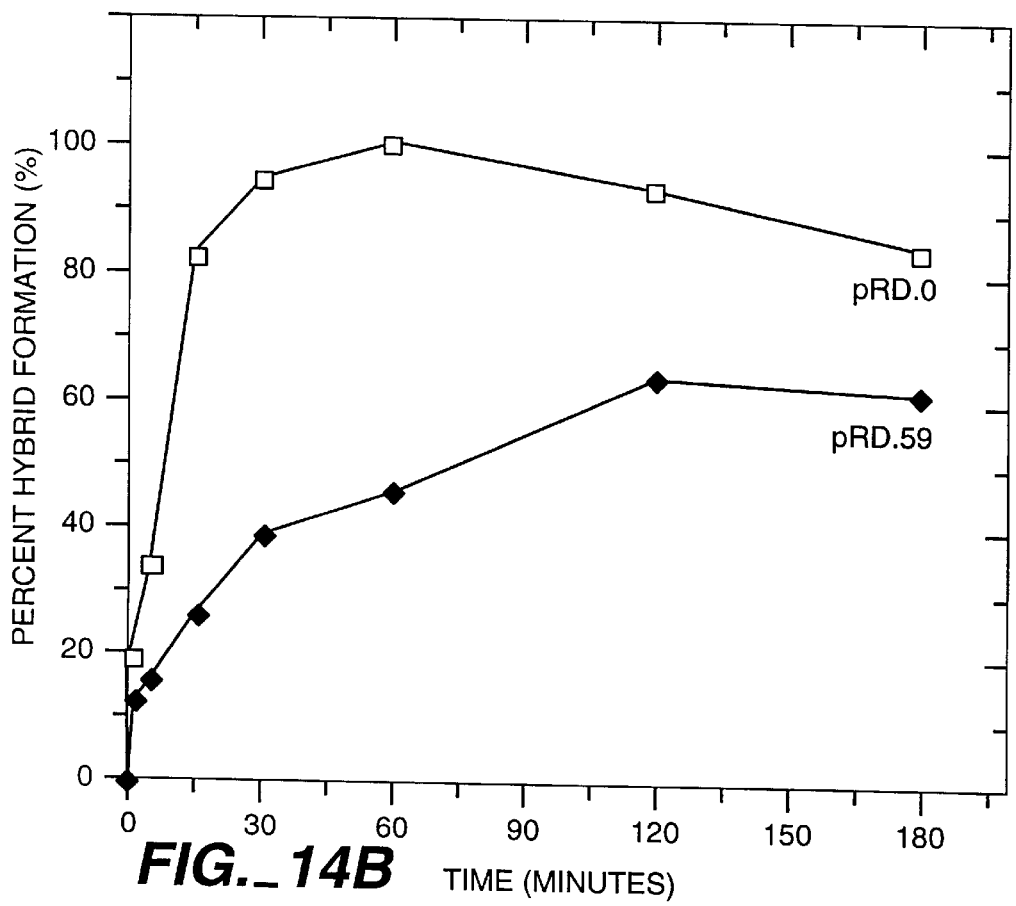
*FIG._14B*  TIME (MINUTES)

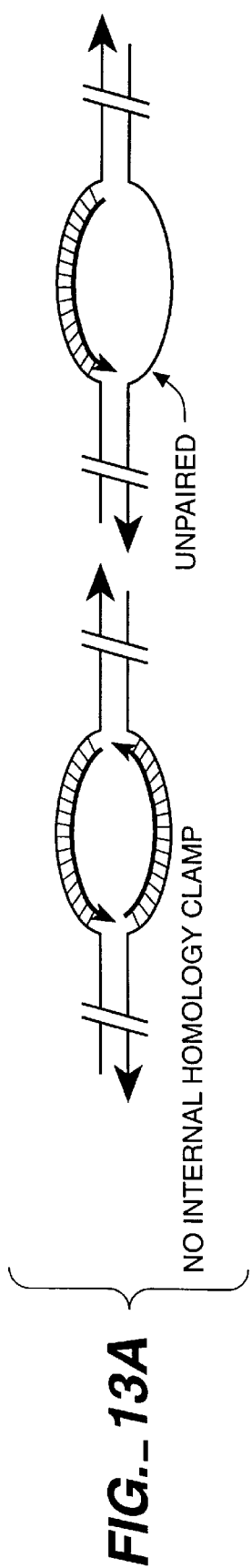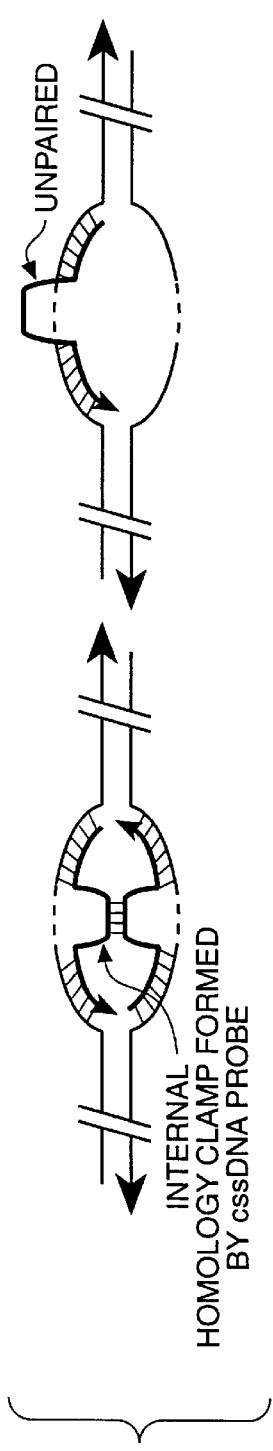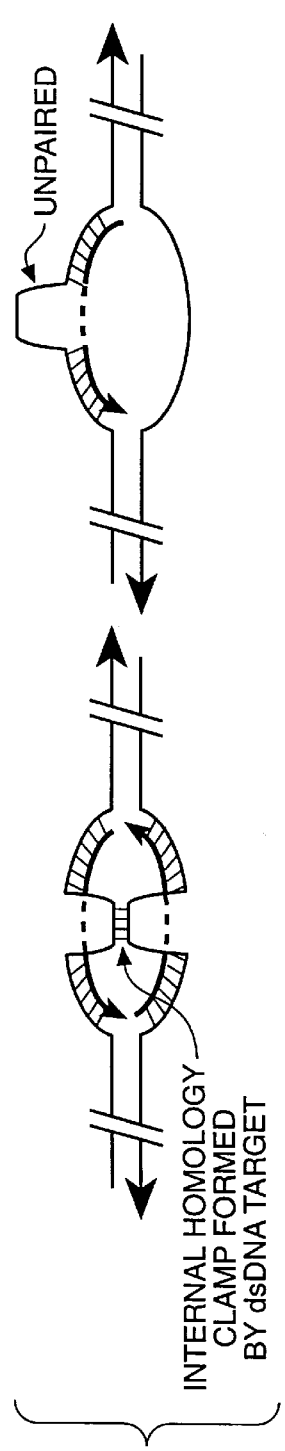

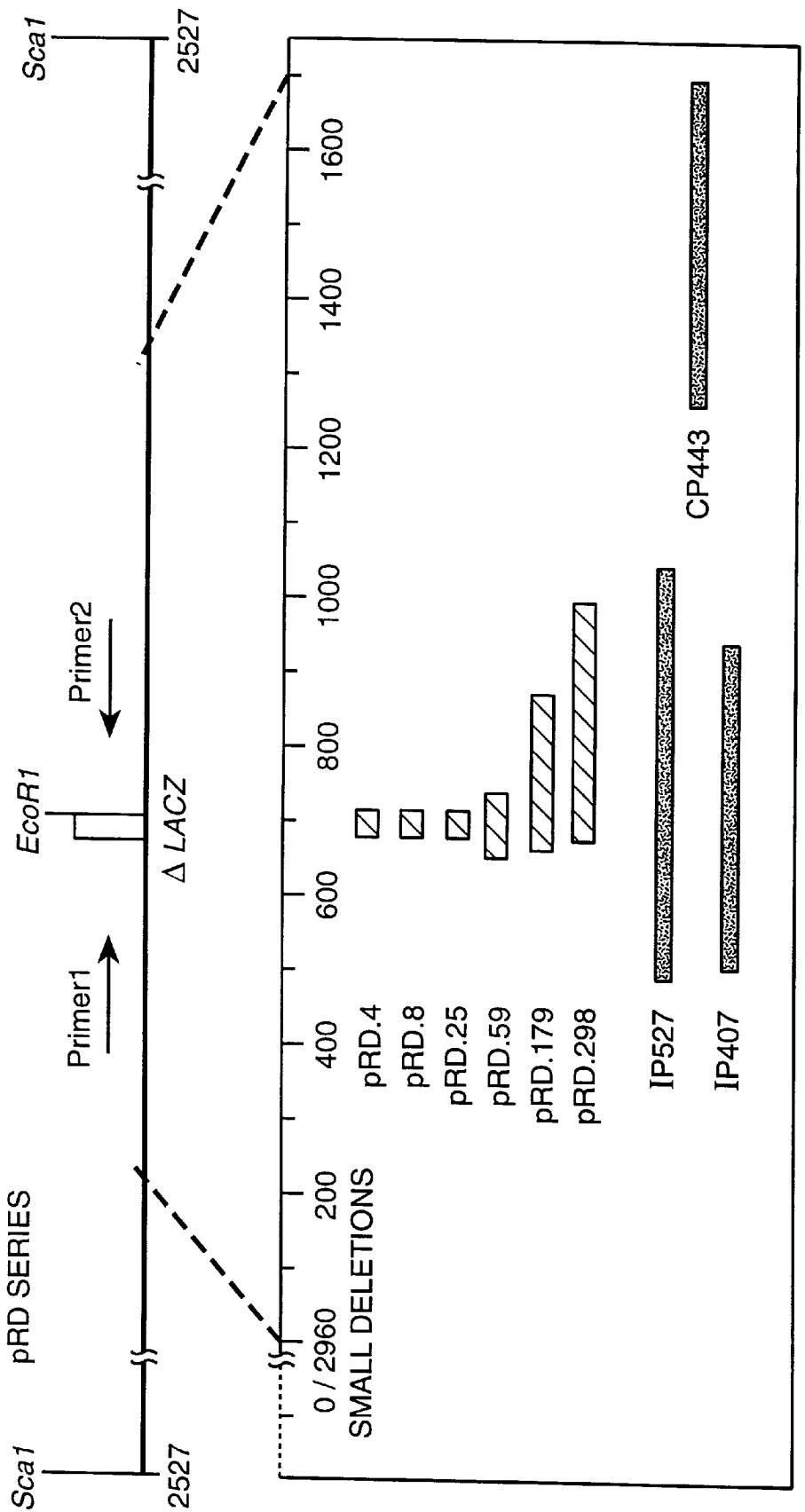
FIG._15A

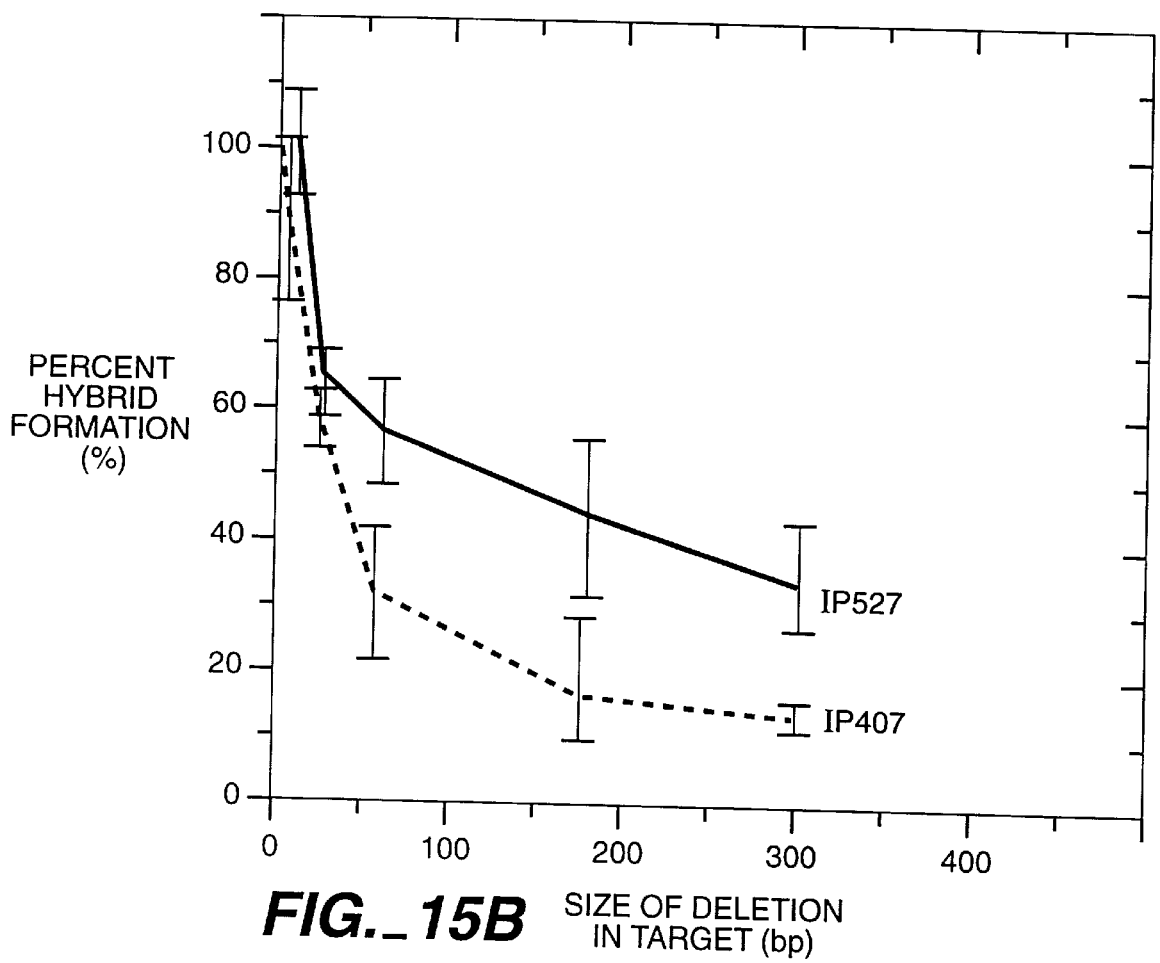
FIG._15B SIZE OF DELETION IN TARGET (bp)
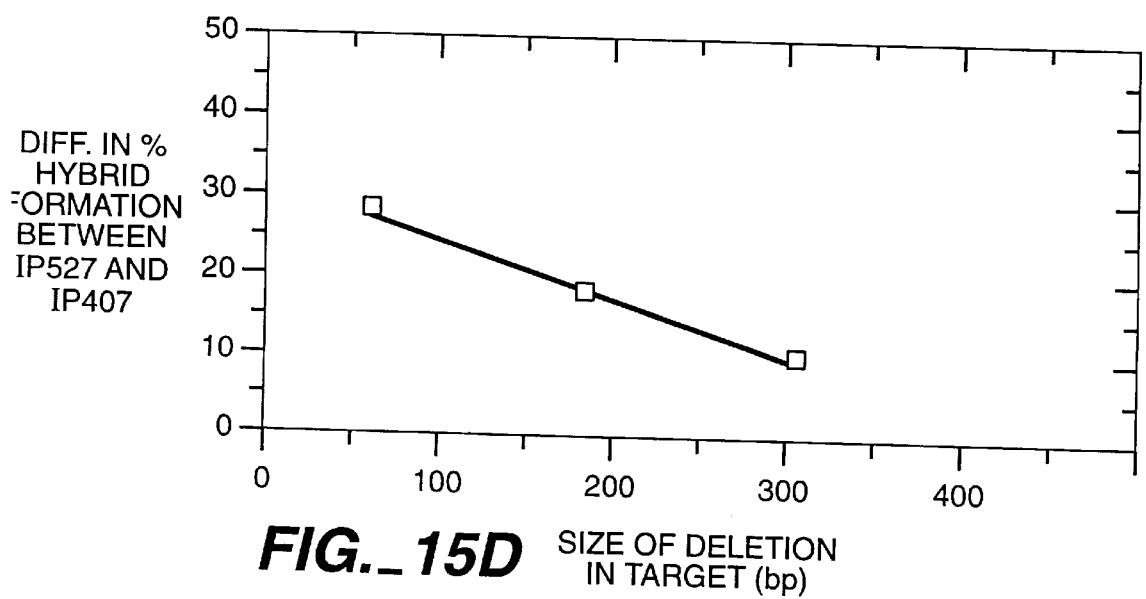
FIG._15D SIZE OF DELETION IN TARGET (bp)

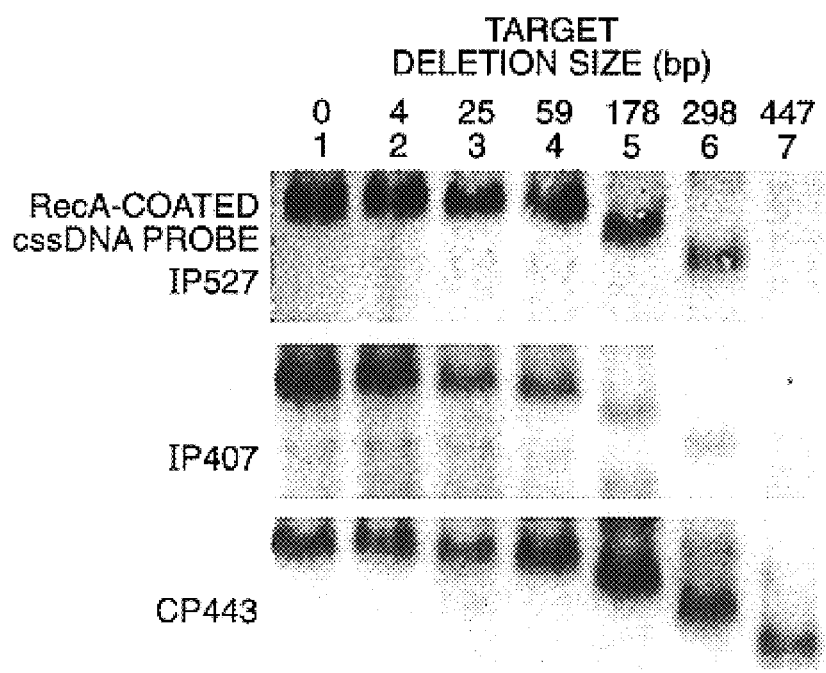
FIG._15C
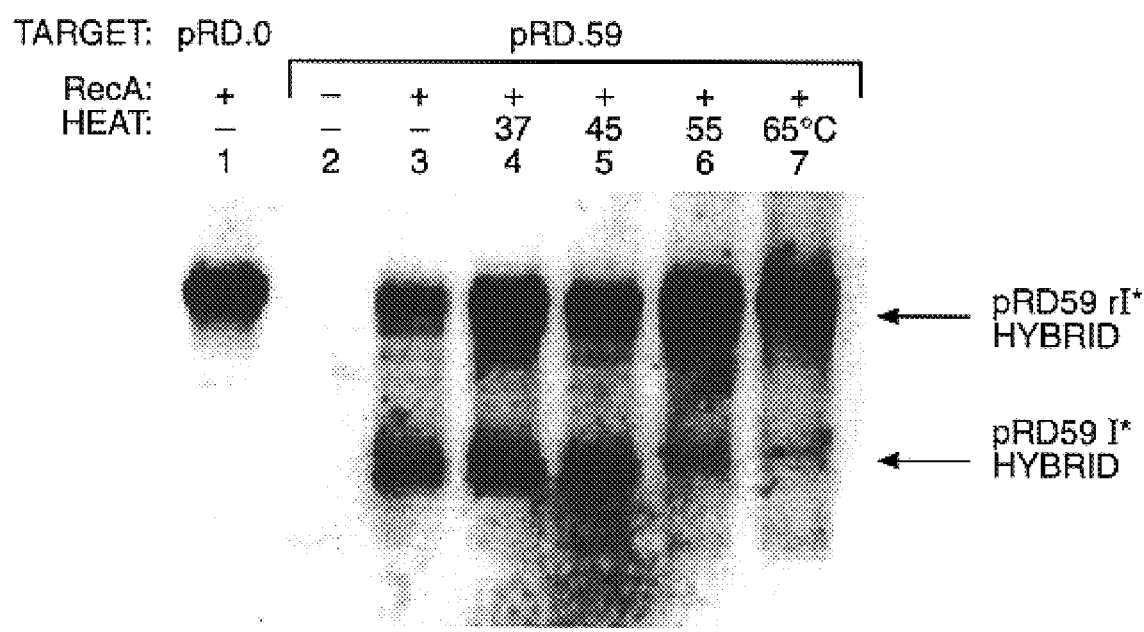
FIG._19

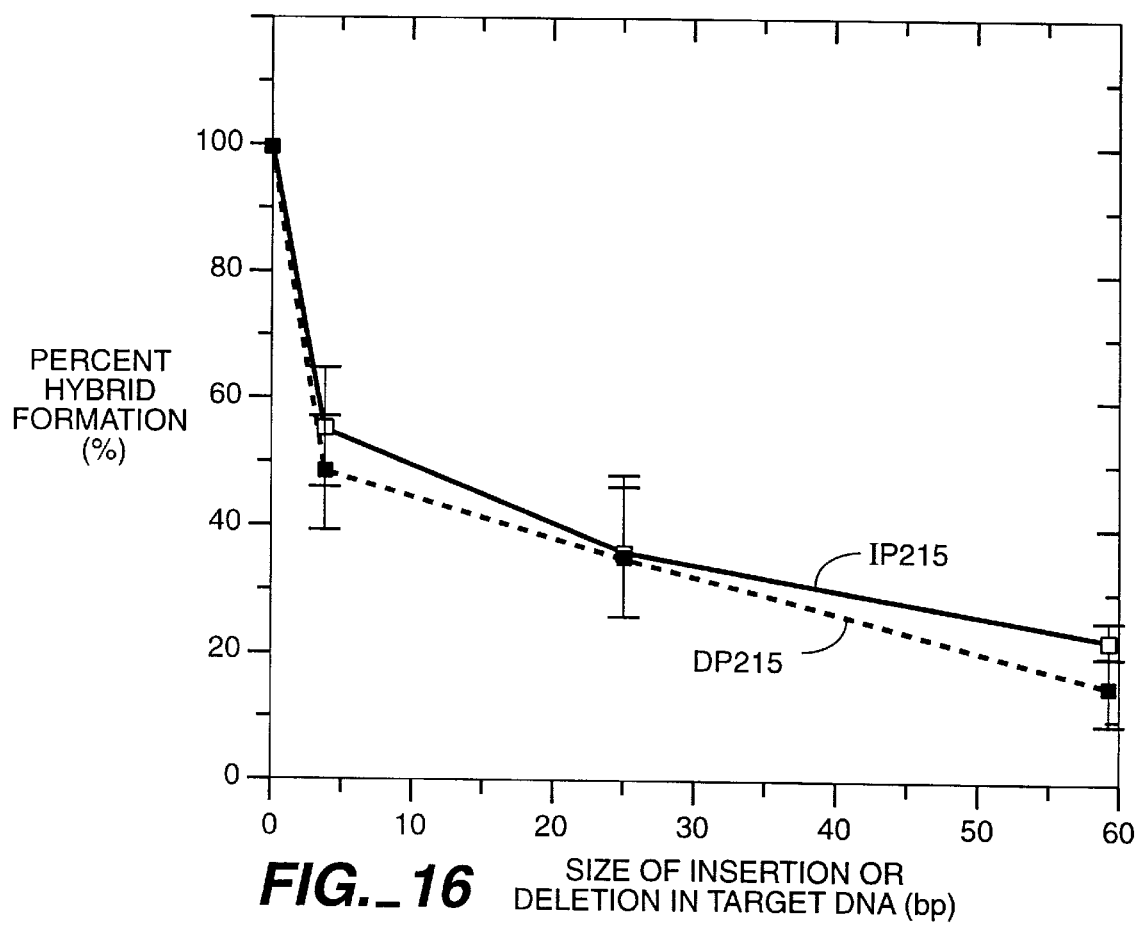
FIG._16  SIZE OF INSERTION OR DELETION IN TARGET DNA (bp)
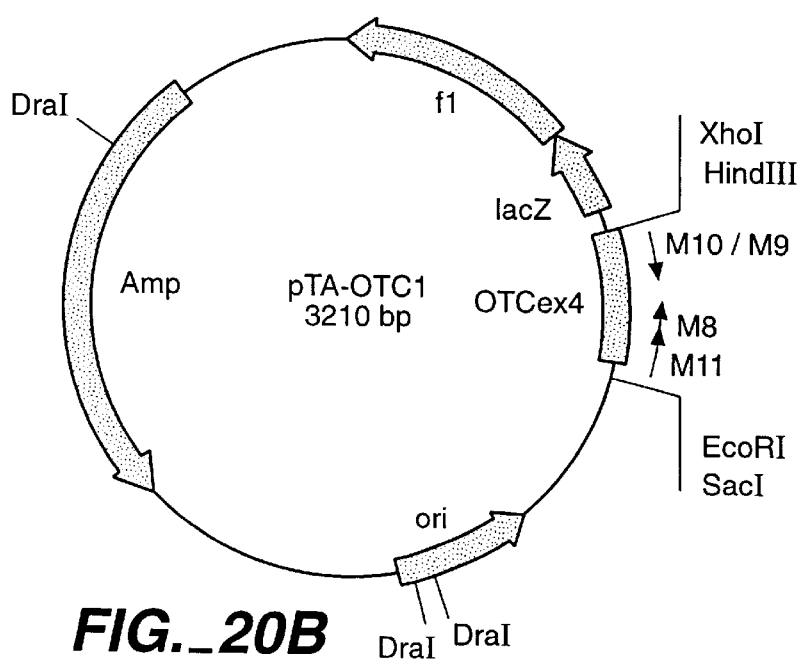
FIG._20B

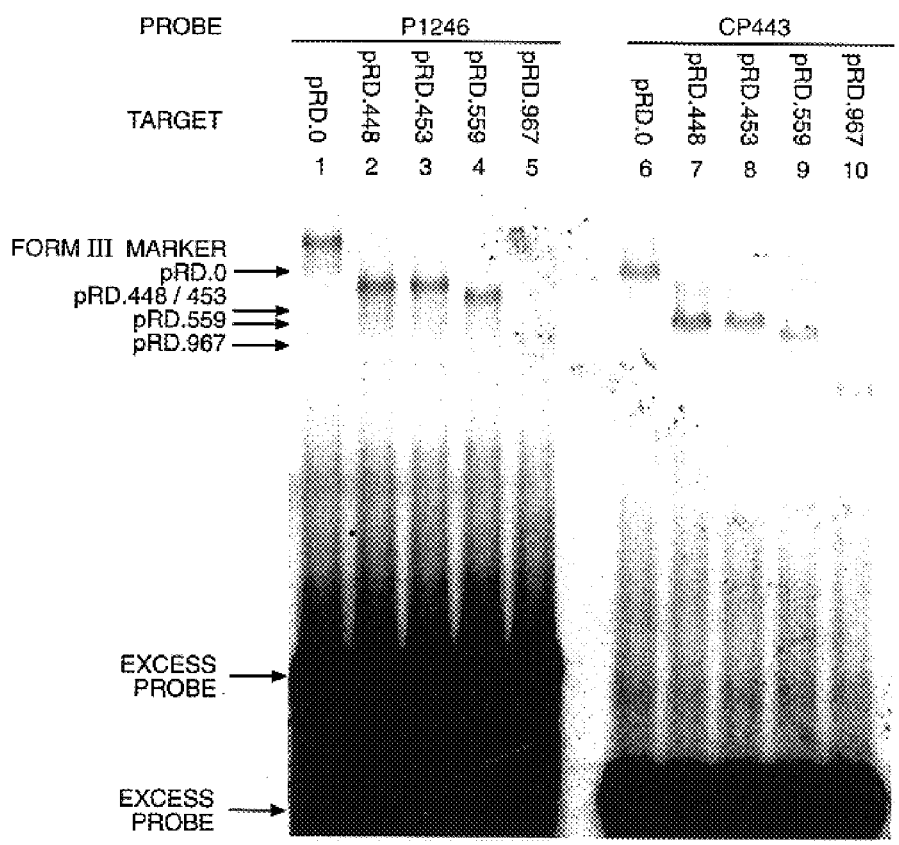
FIG._17A

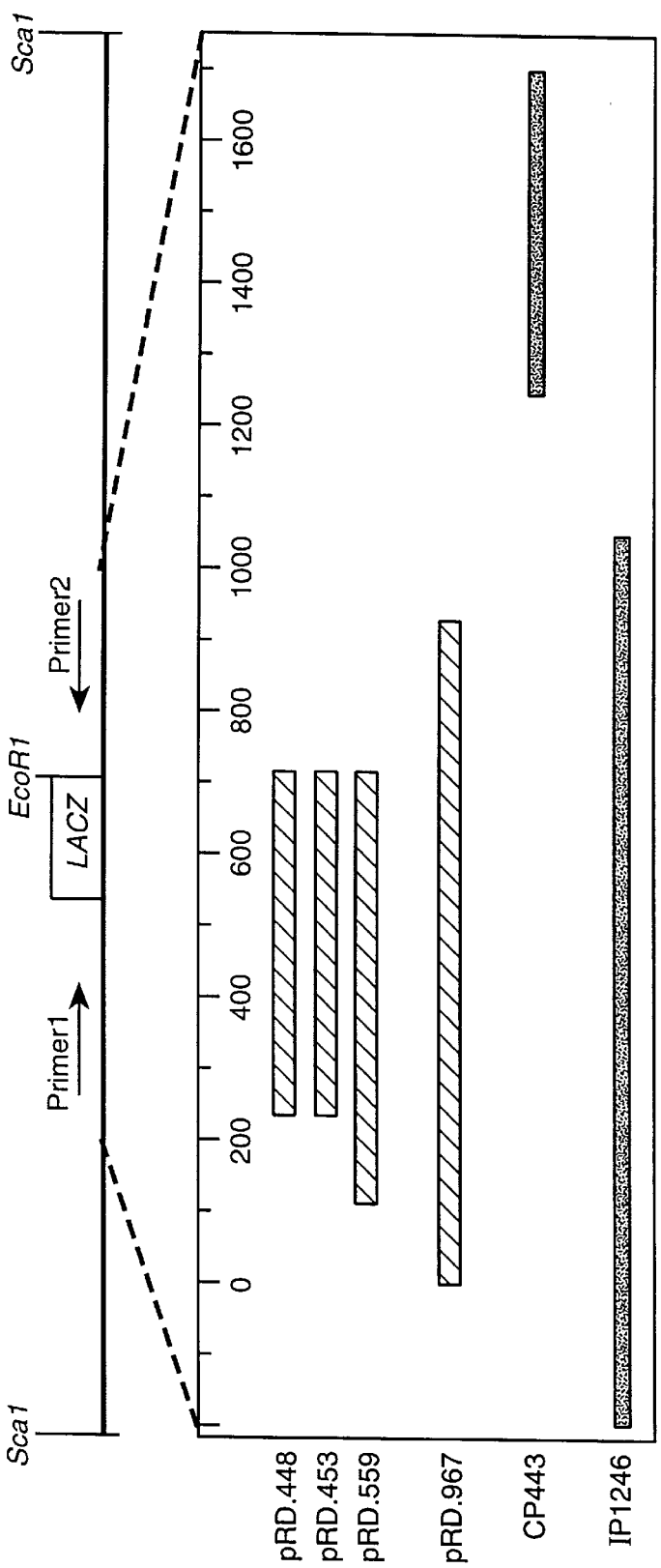
FIG._17B
FIG._17C

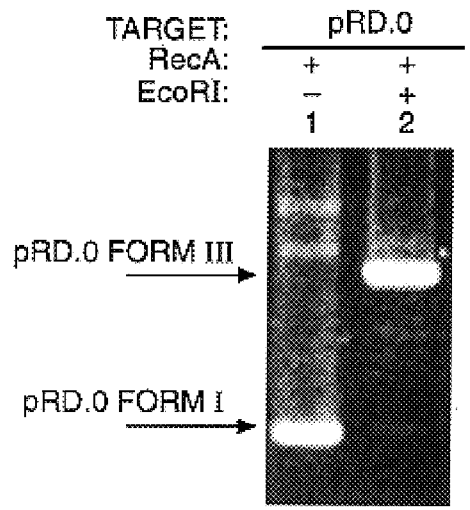
FIG._18A
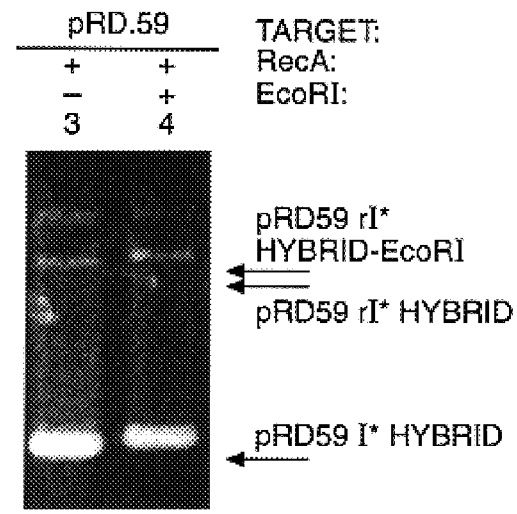
FIG._18B
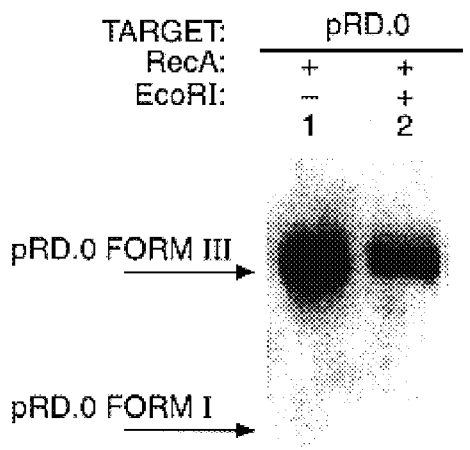
FIG._18C
FIG._18D

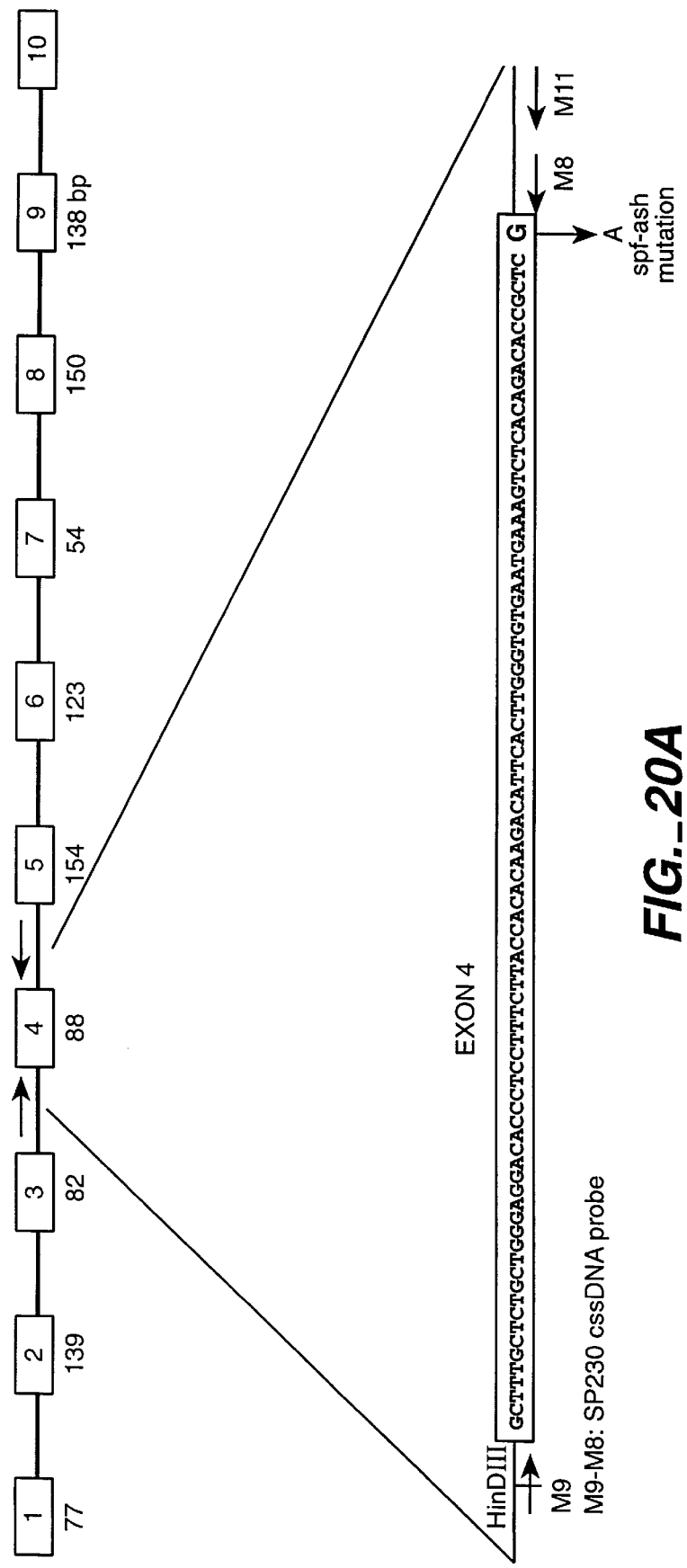
FIG._20A

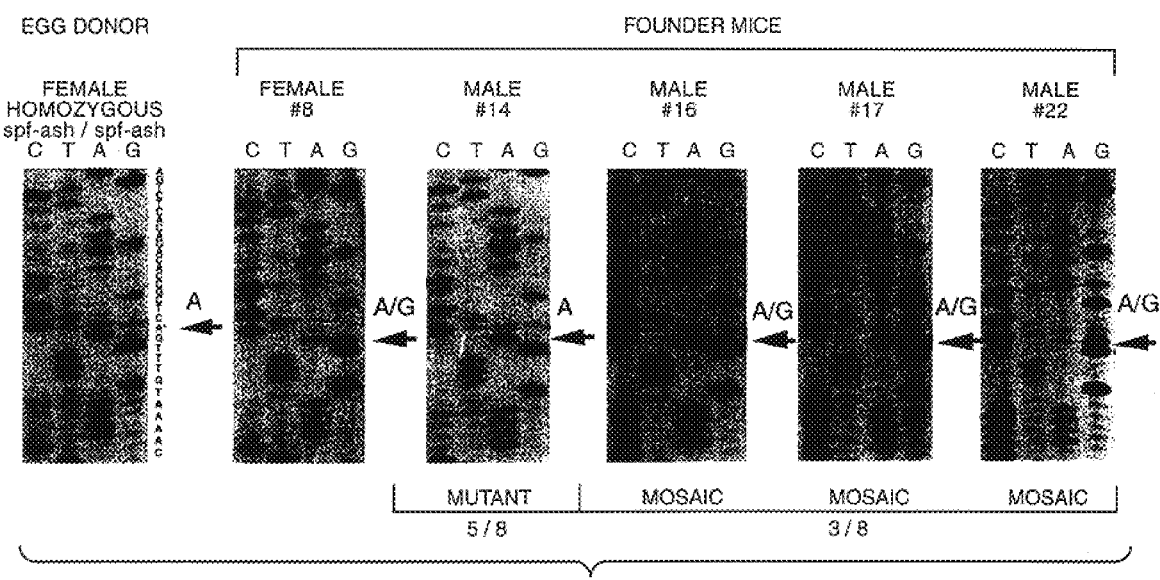
FIG._21

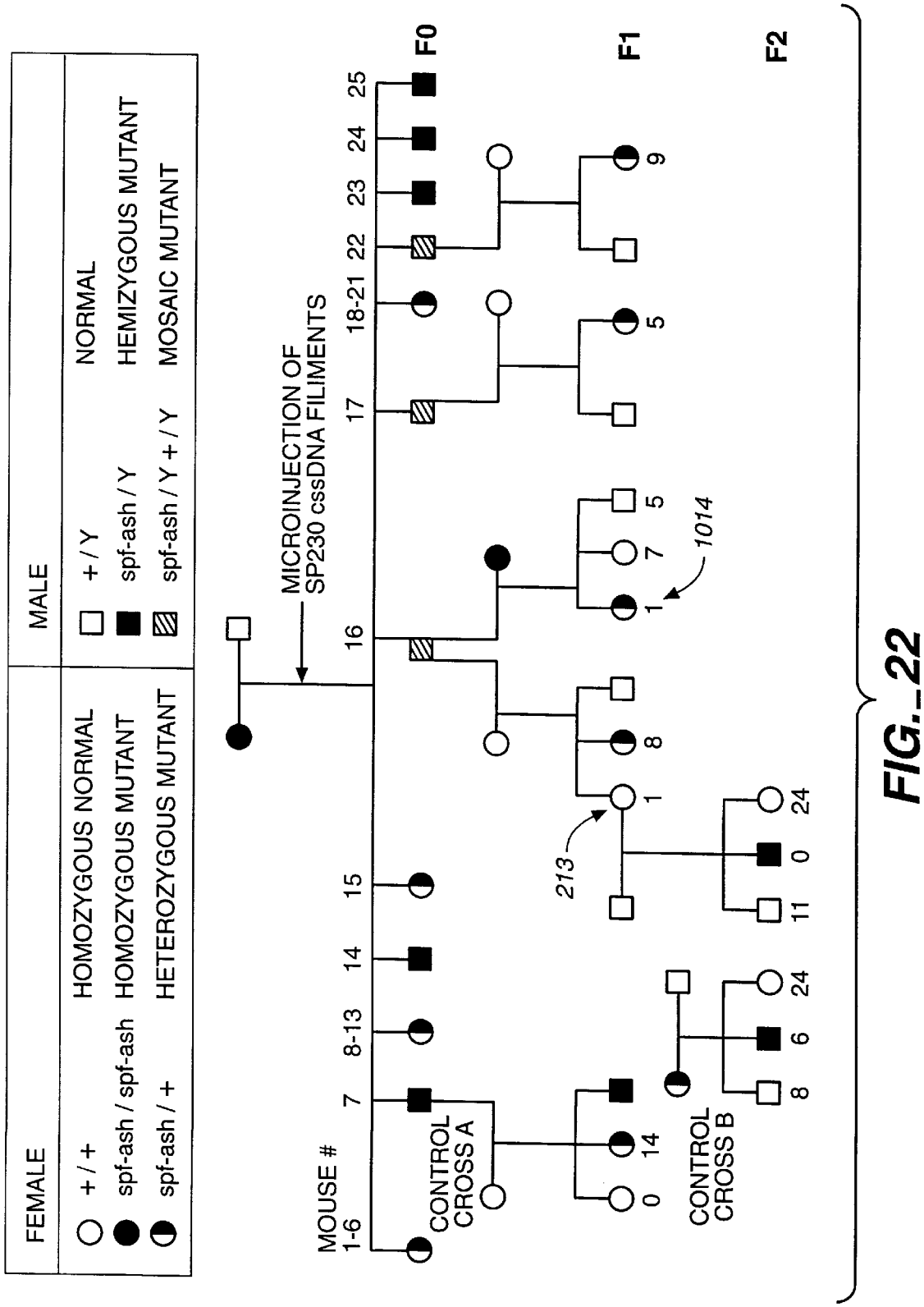
FIG._22

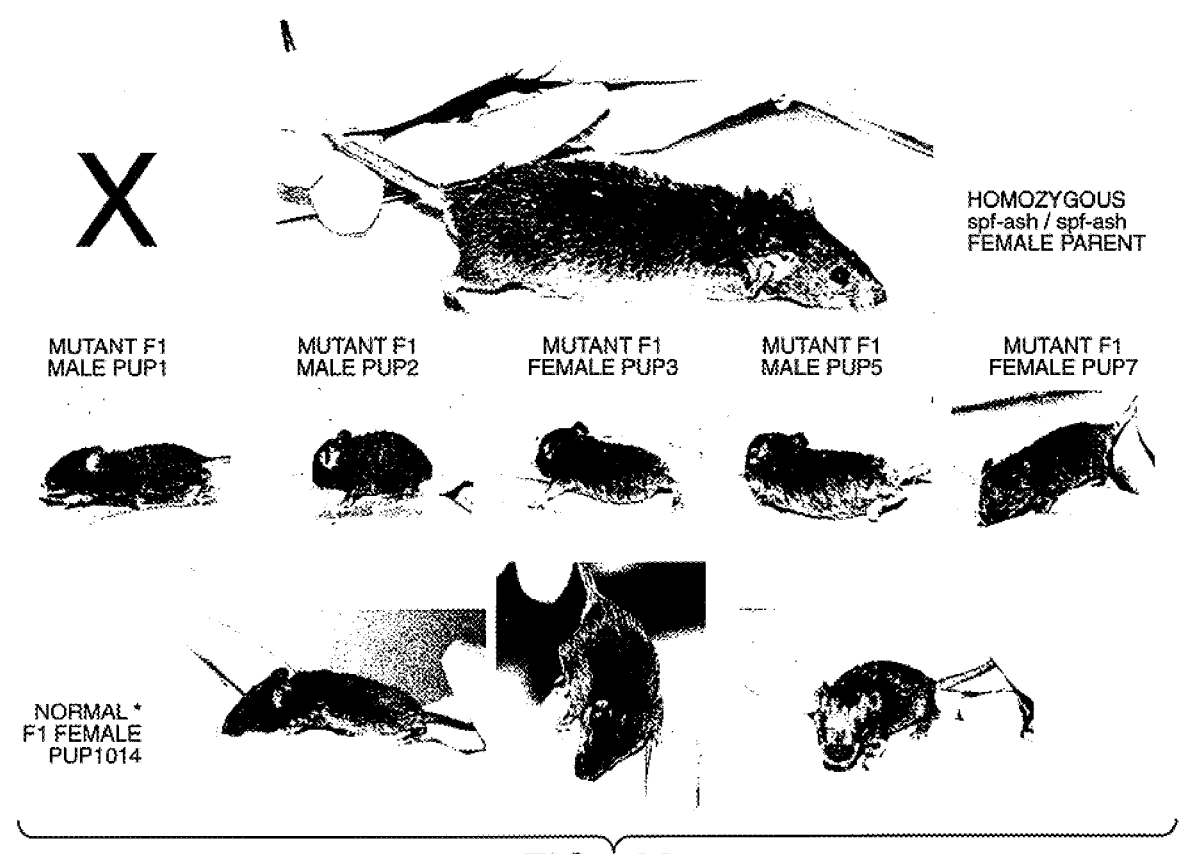
FIG._23

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 11 base pairs
      (B) TYPE: nucleic acid
      (C) STRANDEDNESS: unknown
      (D) TOPOLOGY: unknown (ii) MOLECULE TYPE: DNA (xi) SEQUENCE DESCRIPTION: SEQ ID NO: 1:

CTCTAGACGC G                                                            11

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: unknown
      (D) TOPOLOGY: unknown (ii) MOLECULE TYPE: DNA (xi) SEQUENCE DESCRIPTION: SEQ ID NO: 2:

GCAGAGTACC TGAAACAGGA                                      20

(2) INFORMATION FOR SEQ ID NO: 3:

(i) SEQUENCE CHARACTERISTICS:
      (A) LENGTH: 20 base pairs
      (B) TYPE: nucleic acid
      (C) STRANDEDNESS: unknown
      (D) TOPOLOGY: unknown (ii) MOLECULE TYPE: DNA (xi) SEQUENCE DESCRIPTION: SEQ ID NO: 3:

CATTCACAGT AGCTTACCCA                                      20

(2) INFORMATION FOR SEQ ID NO: 4:

(i) SEQUENCE CHARACTERISTICS:
      (A) LENGTH: 22 base pairs
      (B) TYPE: nucleic acid
      (C) STRANDEDNESS: unknown (D) TOPOLOGY: unknown (ii) MOLECULE TYPE: DNA (xi) SEQUENCE DESCRIPTION: SEQ ID NO: 4:

CCACATATCA CTATATGCAT GC                                              22

(2) INFORMATION FOR SEQ ID NO: 5:

(i) SEQUENCE CHARACTERISTICS:
          (A) LENGTH: 22 base pairs
          (B) TYPE: nucleic acid
          (C) STRANDEDNESS: unknown
          (D) TOPOLOGY: unknown (ii) MOLECULE TYPE: DNA (xi) SEQUENCE DESCRIPTION: SEQ ID NO: 5:

GAGGGATTTG GGGAATTATT TG                                              22

(2) INFORMATION FOR SEQ ID NO: 6:

(i) SEQUENCE CHARACTERISTICS:
          (A) LENGTH: 19 base pairs
          (B) TYPE: nucleic acid
          (C) STRANDEDNESS: unknown
          (D) TOPOLOGY: unknown (ii) MOLECULE TYPE: DNA (xi) SEQUENCE DESCRIPTION: SEQ ID NO: 6:

CACCAAAGAT GATATTTTC                                                  19

(2) INFORMATION FOR SEQ ID NO: 7:

(i) SEQUENCE CHARACTERISTICS:
          (A) LENGTH: 19 base pairs
          (B) TYPE: nucleic acid
          (C) STRANDEDNESS: unknown
          (D) TOPOLOGY: unknown (ii) MOLECULE TYPE: DNA (xi) SEQUENCE DESCRIPTION: SEQ ID NO: 7:

AACACCAAGA TATTTTCTT                                                  19

(2) INFORMATION FOR SEQ ID NO: 8:

(i) SEQUENCE CHARACTERISTICS:
          (A) LENGTH: 431 base pairs
          (B) TYPE: nucleic acid
          (C) STRANDEDNESS: unknown
          (D) TOPOLOGY: unknown (ii) MOLECULE TYPE: DNA (xi) SEQUENCE DESCRIPTION: SEQ ID NO: 8:

ATAAAAAACA ACTGCTGACG CCGCTGCGCG ATCAGTTCAC CCGTGCACCG CTGGATAACG      60

ACATTGGCGT AAGTGAAGCG ACCCGCATTG ACCCTAACGC CTGGGTCGAA CGCTGGAAG      120

CGGCGGGCCA TTACCAGGCC GAAGCAGCGT TGTTGCAGTG CACGGCAGAT ACACTTGCT      180

ATGCGGTGCT GATTACGACC GCTCACGCGT CTCTAGACGC GGGCAGCATC AGGGGAAAA      240

CTTATTTATC AGCCGGAAAA CCTACCGGAT TGATGGTAGT GGTCAAATGG CGATTACCG      300

TGATGTTGAA GTGGCGAGCG ATACACCGCA TCCGGCGCGG ATTGGCCTGA ACTGCCAGC      360

GGCGCAGGTA GCAGAGCGGG TAAACTGGCT CGGATTAGGG CCGCAAGAAA ACTATCCCG      420

```
CCGCCTTACT G                                                           431

(2) INFORMATION FOR SEQ ID NO: 9:

(i) SEQUENCE CHARACTERISTICS:
        (A) LENGTH: 86 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 9:

GCTTTGCTCT GCTGGGAGGA CACCCTCCTT TCTTACCACA CAAGACATTC ACTTGGGTGT       60

GAATGAAAGT CTCACAGACA CCGCTC                                            86

(2) INFORMATION FOR SEQ ID NO: 10:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 10:

AGTCTCACAG ACACCGCTCA GTTTGTAAAA C                                      31
```

SEQUENCE ALTERATIONS USING HOMOLOGOUS RECOMBINATION

CROSS-REFERENCE TO RELATED APPLICATIONS

This application is a continuing application of U.S. application Ser. No. 08/910,367, filed Aug. 13, 1997, now issued as U.S. Pat. No. 5,948,653 on Sep. 7, 1999, which claims the benefit of the filing date of U.S. application Ser. No. 60/041,173, filed Mar. 21, 1997.

FIELD OF THE INVENTION

The invention relates to methods for targeting an exogenous polynucleotide or exogenous complementary polynucleotide pair to a predetermined endogenous DNA target sequence in a target cell by homologous pairing, particularly for altering an endogenous DNA sequence, such as a chromosomal DNA sequence, typically by targeted homologous recombination. In certain embodiments, the invention relates to methods for targeting an exogenous polynucleotide having a linked chemical substituent to a predetermined endogenous DNA sequence in a metabolically active target cell, generating a DNA sequence-specific targeting of one or more chemical substituents in a metabolically active living target cell, generally for purposes of altering a predetermined endogenous DNA sequence in the cell. The invention also relates to compositions and formulations that contain exogenous targeting polynucleotides, complementary pairs of exogenous targeting polynucleotides, chemical substituents of such polynucleotides, and recombinase proteins, including recombinosome proteins and other targeting proteins, used in the methods of the invention.

BACKGROUND

Homologous recombination (or general recombination) is defined as the exchange of homologous segments anywhere along a length of two DNA molecules. An essential feature of general recombination is that the enzymes responsible for the recombination event can presumably use any pair of homologous sequences as substrates, although some types of sequence may be favored over others. Both genetic and cytological studies have indicated that such a crossing-over process occurs between pairs of homologous chromosomes during meiosis in higher organisms.

Alternatively, in site-specific recombination, exchange occurs at a specific site, as in the integration of phage λ into the *E. coli* chromosome and the excision of λ DNA from it. Site-specific recombination involves specific inverted repeat sequences; e.g. the Cre-loxP and FLP-FRT systems. Within these sequences there is only a short stretch of homology necessary for the recombination event, but not sufficient for it. The enzymes involved in this event generally cannot recombine other pairs of homologous (or nonhomologous) sequences, but act specifically.

Although both site-specific recombination and homologous recombination are useful mechanisms for genetic engineering of DNA sequences, targeted homologous recombination provides a basis for targeting and altering essentially any desired sequence in a duplex DNA molecule, such as targeting a DNA sequence in a chromosome for replacement by another sequence. Site-specific recombination has been proposed as one method to integrate transfected DNA at chromosomal locations having specific recognition sites (O'Gorman et al. (1991) *Science* 251: 1351; Onouchi et al. (1991) *Nucleic Acids Res.* 19: 6373). Unfortunately, since this approach requires the presence of specific target sequences and recombinases, its utility for targeting recombination events at any particular chromosomal location is severely limited in comparison to targeted general recombination.

For these reasons and others, targeted homologous recombination has been proposed for treating human genetic diseases. Human genetic diseases include (1) classical human genetic diseases wherein a disease allele having a mutant genetic lesion is inherited from a parent (e.g., adenosine deaminase deficiency, sickle cell anemia, thalassemias), (2) complex genetic diseases like cancer, where the pathological state generally results from one or more specific inherited or acquired mutations, and (3) acquired genetic disease, such as an integrated provirus (e.g., hepatitis B virus).

Homologous recombination has also been used to create transgenic animals. Transgenic animals are organisms that contain stably integrated copies of genes or gene constructs derived from another species in the chromosome of the transgenic animal. These animals can be generated by introducing cloned DNA constructs of the foreign genes into totipotent cells by a variety of methods, including homologous recombination. Animals that develop from genetically altered totipotent cells contain the foreign gene in all somatic cells and also in germ-line cells if the foreign gene was integrated into the genome of the recipient cell before the first cell division. Currently methods for producing transgenics have been performed on totipotent embryonic stem cells (ES) and with fertilized zygotes. ES cells have an advantage in that large numbers of cells can be manipulated easily by homologous recombination in vitro before they are used to generate transgenics. Currently, however, only embryonic stem cells from mice have been characterized as contributing to the germ line. Alternatively, DNA can also be introduced into fertilized oocytes by micro-injection into pronuclei which are then transferred into the uterus of a pseudo-pregnant recipient animal to develop to term. However because current homologous recombination methods are inefficient and it is not logistically possible to manipulate large numbers of fertilized zygotes, transgenic animals produced by zygote microinjection are generally the result of random integration (not targeted) of the gene construct. A few cases of relatively inefficient homologous recombination in mouse fertilized zygotes have been reported, however these methods have been only been applied to a few specific target genes (Brinster et al. (1989) PNAS 86: 7087; Susulic et al. (1995) JBC 49: 29483; Zimmer and Gruss (1989) Nature 338: 150] and the general utility of homologous recombination in zygotes for any desired target gene has not been observed.

Commercial applications to produce transgenic animals by homologous recombination include 1) animal models to study gene function; 2) animal models that mimic human disease; 3) animals that produce therapeutic proteins from a known, pre-designated stable site in the chromosome; 4) animals that produce milk with superior nutritional value; 5) animal livestock with superior qualities, including disease and pathogen resistance; and 6) genetically altered animals that produce organs that are suitable for xenotransplantation. However as stated above, current methods for homologous recombination are generally inefficient and since ES cells which contribute to the germ line have only been identified for mice, homologous recombination has not been enabled for producing transgenic animals in any other species other than two strains of mice. Thus, current methods of targeted homologous recombination are inefficient and produce desired homologous recombinants only rarely, necessitating complex cell selection schemes to identify and isolate correctly targeted recombinants.

A primary step in homologous recombination is DNA strand exchange, which involves a pairing of a DNA duplex with at least one DNA strand containing a complementary sequence to form an intermediate recombination structure containing heteroduplex DNA (see, Radding, C. M. (1982) *Ann. Rev. Genet.* 16: 405; U.S. Pat. No. 4,888,274). The heteroduplex DNA may take several forms, including a three DNA strand containing triplex form wherein a single complementary strand invades the DNA duplex (Hsieh et al. (1990) *Genes and Development* 4: 1951; Rao et al., (1991) PNAS 88:2984)) and, when two complementary DNA strands pair with a DNA duplex, a classical Holliday recombination joint or chi structure (Holliday, R. (1964) *Genet. Res.* 5: 282) may form, or a double-D loop ("Diagnostic Applications of Double-D Loop Formation" U.S. Ser. No. 07/755,462, filed Sep. 4, 1991, which is incorporated herein by reference). Once formed, a heteroduplex structure may be resolved by strand breakage and exchange, so that all or a portion of an invading DNA strand is spliced into a recipient DNA duplex, adding or replacing a segment of the recipient DNA duplex. Alternatively, a heteroduplex structure may result in gene conversion, wherein a sequence of an invading strand is transferred to a recipient DNA duplex by repair of mismatched bases using the invading strand as a template (*Genes,* 3rd Ed. (1987) Lewin, B., John Wiley, New York, N.Y.; Lopez et al. (1987) *Nucleic Acids Res.* 15: 5643). Whether by the mechanism of breakage and rejoining or by the mechanism(s) of gene conversion, formation of heteroduplex DNA at homologously paired joints can serve to transfer genetic sequence information from one DNA molecule to another.

The ability of homologous recombination (gene conversion and classical strand breakage/rejoining) to transfer genetic sequence information between DNA molecules makes targeted homologous recombination a powerful method in genetic engineering and gene manipulation.

The ability of mammalian and human cells to incorporate exogenous genetic material into genes residing on chromosomes has demonstrated that these cells have the general enzymatic machinery for carrying out homologous recombination required between resident and introduced sequences. These targeted recombination events can be used to correct mutations at known sites, replace genes or gene segments with defective ones, or introduce foreign genes into cells. The efficiency of such gene targeting techniques is related to several parameters: the efficiency of DNA delivery into cells, the type of DNA packaging (if any) and the size and conformation of the incoming DNA, the length and position of regions homologous to the target site (all these parameters also likely affect the ability of the incoming homologous DNA sequences to survive intracellular nuclease attack), the efficiency of hybridization and recombination at particular chromosomal sites and whether recombinant events are homologous or nonhomologous. Over the past 10 years or so, several methods have been developed to introduce DNA into mammalian cells: direct needle microinjection, transfection, electroporation, retroviruses, adenoviruses, adeno-associated viruses; Herpes viruses, and other viral packaging and delivery systems, polyamidoamine dendimers, liposomes, and more recently techniques using DNA-coated microprojectiles delivered with a gene gun (called a biolistics device), or narrow-beam lasers (laser-poration). The processes associated with some types of gene transfer have been shown to be pathogenic, mutagenic or carcinogenic (Bardwell, (1989) *Mutagenesis* 4: 245), and these possibilities must be considered in choosing a transfection approach.

The choice of a particular DNA transfection procedure depends upon its availability to the researcher, the technique's efficiency with the particular chosen target cell type, and the researchers concerns about the potential for generating unwanted genome mutations. For example, retroviral integration requires dividing cells, most often results in nonhomologous recombination events, and retroviral insertion within a coding sequence of nonhomologous (i.e., non-targeted) gene could cause cell mutation by inactivating the gene's coding sequence (Friedmann, (1989) *Science* 244:1275). Newer retroviral-based DNA delivery systems are being developed using modified retroviruses. However, these disabled viruses must be packaged using helper systems, are often obtained at low titer, and recombination is still not site-specific, thus recombination between endogenous cellular retrovirus sequences and disabled virus sequences could still produce wild-type retrovirus capable of causing gene mutation. Adeno- or polyoma virus based delivery systems appear promising (Samulski et al., (1991) *EMBO J.* 10: 2941; Gareis et al., (1991) *Cell. Molec. Biol.* 37: 191; Rosenfeld et al. (1992) *Cell* 68: 143) although they still require specific cell membrane recognition and binding characteristics for target cell entry. Liposomes often show a narrow spectrum of cell specificities, and when DNA is coated externally on to them, the DNA is often sensitive to cellular nucleases. Newer polycationic lipospermines compounds exhibit broad cell ranges (Behr et al., (1989) *Proc. Natl. Acad. Sci. USA* 86: 6982) and DNA is coated by these compounds. In addition, a combination of neutral and cationic lipid has been shown to be highly efficient at transfection of animal cells and showed a broad spectrum of effectiveness in a variety of cell lines (Rose et al., (1991) *BioTechniques* 10:520). Galactosylated bis-acridine has also been described as a carrier for delivery of polynucleotides to liver cells (Haensler J L and Szoka F C (1992), Abstract V211 in *J. Cell. Biochem.* Supplement 16F, Apr. 3–16, 1992, incorporated herein by reference). Electroporation also appears to be applicable to most cell types. The efficiency of this procedure for a specific gene is variable and can range from about one event per $3\times10^4$ transfected cells (Thomas and Capecchi, (1987) *Cell* 51: 503) to between one in $10^7$ and $10^8$ cells receiving the exogenous DNA (Koller and Smithies, (1989) *Proc. Natl. Acad. Sci. (U.S.A.)* 86: 8932). Microinjection of exogenous DNA into the nucleus has been reported to result in stable integration in transfected cells. Zimmer and Gruss (Zimmer and Gruss (1989) *Nature* 338: 150) have reported that for the mouse hox1.1 gene, 1 per 150 microinjected cells showed a stable homologous site specific alteration.

Several methods have been developed to detect and/or select for targeted site-specific recombinants between vector DNA and the target homologous chromosomal sequence (see, Capecchi, (1989) *Science* 244: 1288 for review). Cells which exhibit a specific phenotype after site-specific recombination, such as occurs with alteration of the hprt gene, can be obtained by direct selection on the appropriate growth medium. Alternatively, a selective marker sequence such as neo can be incorporated into a vector under promoter control, and successful transfection can be scored by selecting G418$^r$ cells followed by PCR to determine whether neo is at the targeted site (Joyner et al., (1989) *Nature* 338: 153). A positive-negative selection (PNS) procedure using both neo and HSV-tk genes allows selection for transfectants and against nonhomologous recombination events, and significantly enriched for desired disruption events at several different mouse genes (Mansour et al., (1988) *Nature* 336: 348). This procedure has the advantage that the method does not require that the targeted gene be transcribed. If the targeted gene is transcribed, a promoter-less marker gene can be incorporated into the targeting construct so that the gene becomes activated after homologous recombination with the target site (Jasin and Berg, (1988) *Genes and Development* 2: 1353; Doetschman et al. (1988) *Proc. Natl. Acad. Sci. (U.S.A.)* 85: 8583; Dorini et al., (1989) *Science* 243: 1357; Itzhaki and Porter, (1991) *Nucl. Acids Res.* 19: 3835). Recombinant products produced using vectors with selectable markers often continue to retain these markers as foreign genetic material at the site of transfection, although loss does occur. Valancius and Smithies (Valancius and Smithies, (1991) *Mole. Cellular Biol.* 11: 1402) have described an "in-out" targeting procedure that allowed a subtle 4-bp insertion modification of a mouse hprt target gene. The resulting transfectant contained only the desired modified gene sequence and no selectable marker remained after the "out" recombination step. Cotransformation of cells with two different vectors, one vector contained a selectable gene and the other used for gene disruption, increases the efficiency of isolating a specific targeting reaction (Reid et al., (1991) *Molec. Cellular Biol.* 11: 2769) among selected cells that are subsequently scored for stable recombinants.

Unfortunately, exogenous sequences transferred into eukaryotic cells undergo homologous recombination with homologous endogenous sequences only at very low frequencies, and are so inefficiently recombined that large numbers of cells must be transfected, selected, and screened in order to generate a desired correctly targeted homologous recombinant (Kucherlapati et al. (1984) *Proc. Natl. Acad. Sci. (U.S.A.)* 81: 3153; Smithies, O. (1985) *Nature* 317: 230; Song et al. (1987) *Proc. Natl. Acad. Sci. (U.S.A.)* 84: 6820; Doetschman et al. (1987) *Nature* 330: 576; Kim and Smithies (1988) *Nucleic Acids Res.* 16: 8887; Doetschman et al. (1988) op.cit.; Koller and Smithies (1989) op.cit.; Shesely et al. (1991) *Proc. Natl. Acad. Sci. (U.S.A.)* 88: 4294; Kim et al. (1991) *Gene* 103: 227, which are incorporated herein by reference).

Koller et al. (1991) *Proc. Natl. Acad. Sci. (U.S.A.)*, 88: 10730 and Snouwaert et al. (1992) *Science* 257: 1083, have described targeting of the mouse cystic fibrosis transmembrane regulator (CFTR) gene for the purpose of inactivating, rather than correcting, a murine CFTR allele. Koller et al. employed a large (7.8 kb) homology region in the targeting construct, but nonetheless reported a low frequency for correct targeting (only 1 of 2500 G418-resistant cells were correctly targeted). Thus, even targeting constructs having long homology regions are inefficiently targeted.

Several proteins or purified extracts having the property of promoting homologous recombination (i.e., recombinase activity) have been identified in prokaryotes and eukaryotes (Cox and Lehman (1987) *Ann. Rev. Biochem.* 56: 229; Radding, C. M. (1982) op.cit.; Madiraju et al. (1988) *Proc. Natl. Acad. Sci. (U.S.A.)* 85: 6592; McCarthy et al. (1988) *Proc. Natl. Acad. Sci. (U.S.A.)* 85: 5854; Lopez et al. (1987) op.cit., which are incorporated herein by reference). These general recombinases presumably promote one or more steps in the formation of homologously-paired intermediates, strand-exchange, gene conversion, and/or other steps in the process of homologous recombination.

The frequency of homologous recombination in prokaryotes is significantly enhanced by the presence of recombinase activities. Several purified proteins catalyze homologous pairing and/or strand exchange in vitro, including: *E. coli* recA protein, the T4 uvsX protein, the rec1 protein from *Ustilago maydis,* and Rad51 protein from *S. cervisiae* (Sung et al., Science 265:1241 (1994)) and human cells (Baumann et al., Cell 87:757 (1996)). Recombinases, like the recA protein of *E. coli* are proteins which promote strand pairing and exchange. The most studied recombinase to date has been the recA recombinase of *E. coli,* which is involved in homology search and strand exchange reactions (see, Cox and Lehman (1987) op.cit.). RecA is required for induction of the SOS repair response, DNA repair, and efficient genetic recombination in *E. coli.* RecA can catalyze homologous pairing of a linear duplex DNA and a homologous single strand DNA in vitro. In contrast to site-specific recombinases, proteins like recA which are involved in general recombination recognize and promote pairing of DNA structures on the basis of shared homology, as has been shown by several in vitro experiments (Hsieh and Camerini-Otero (1989) *J. Biol. Chem.* 264: 5089; Howard-Flanders et al. (1984) *Nature* 309: 215; Stasiak et al. (1984) *Cold Spring Harbor Symp. Quant. Biol.* 49: 561; Register et al. (1987) *J. Biol. Chem.* 262: 12812). Several investigators have used recA protein in vitro to promote homologously paired triplex DNA (Cheng et al. (1988) *J. Biol. Chem.* 263: 15110; Ferrin and Camerini-Otero (1991) *Science* 354: 1494; Ramdas et al. (1989) *J. Biol Chem.* 264: 11395; Strobel et al. (1991) *Science* 254: 1639; Hsieh et al. (1990) op.cit.; Rigas et al. (1986) *Proc. Natl. Acad. Sci. (U.S.A.)* 83: 9591; and Camerini-Otero et al. U.S. Pat. No. 7,611,268 (available from Derwent), which are incorporated herein by reference). Unfortunately many important genetic engineering manipulations involving homologous recombination, such as using homologous recombination to alter endogenous DNA sequences in a living cell, cannot be done in vitro. Further, gene therapy and transgenesis requires highly efficient homologous recombination of targeting vectors with predetermined endogenous target sequences, since selectable marker selection schemes such as those currently available in the art are not usually practicable. Thus, there exists a need in the art for methods of efficiently altering predetermined endogenous genetic sequences by homologous pairing and homologous recombination in vivo by introducing one or more exogenous targeting polynucleotide(s) that efficiently and specifically homologously pair with a predetermined endogenous DNA sequence. There exists a need in the art for high-efficiency gene targeting, so as to avoid complex in vitro selection protocols (e.g., neo gene selection with G418) which are of limited utility for in vivo gene therapy on affected individuals

SUMMARY OF THE INVENTION

It is an object of the present invention to provide methods for targeting an exogenous polynucleotide to a predetermined endogenous DNA target sequence in a target cell with high efficiency and with sequence specificity. Exogenous polynucleotides, are localized (or targeted) to one or more predetermined DNA target sequence(s) by homologous pairing in vivo. Such targeted homologous pairing of exogenous polynucleotides to endogenous DNA sequences in vivo may be used: (1) to target chemical substituents in a sequence-specific manner in vivo, (2) to correct or to generate genetic mutations in endogenous DNA sequences by homologous recombination and/or gene conversion, (3) to produce homologously targeted transgenic organisms, including animals and plants at high efficiency, and (4) in other applications (e.g., targeted drug delivery) based on in vivo homologous pairing. Some embodiments of the invention employ targeted exogenous polynucleotides to correct endogenous mutant gene alleles in human cells; the invention provides methods and compositions for correcting disease alleles involved in producing human genetic diseases, such as inherited genetic diseases (e.g., cystic fibrosis) and neoplasia (e.g., neoplasms induced by somatic mutation of an oncogene or tumor suppressor gene, such as p53, or viral genes associated with neoplasia, such as HBV genes).

In one embodiment, at least one exogenous polynucleotide is targeted to a predetermined endogenous DNA sequence and alters the endogenous DNA sequence, such as a chromosomal DNA sequence, typically by targeted homologous recombination within and/or flanking the predetermined endogenous DNA sequence. Generally, two complementary exogenous polynucleotides are used for targeting an endogenous DNA sequence. Typically, the targeting polynucleotide(s) are introduced simultaneously or contemporaneously with one or more recombinase species. Alternatively, one or more recombinase species may be produced in vivo by expression of a heterologous expression cassette in a cell containing the preselected target DNA sequence.

It is another object of the invention to provide methods whereby at least one exogenous polynucleotide containing a chemical substituent can be targeted to a predetermined endogenous DNA sequence in a metabolically-active or intact living target cell, permitting sequence-specific targeting of chemical substituents such as, for example crosslinking agents, metal chelates (e.g., iron/EDTA chelate for iron catalyzed cleavage), topoisomerases, endonucleases, exonucleases, ligases, phosphodiesterases, photodynamic porphyrins, free-radical generating drugs, chemotherapeutic drugs (e.g., adriamycin, doxirubicin), intercalating agents, base-modification agents, immunoglobulin chains, oligonucleotides, and other substituents. The methods of the invention can be used to target such a chemical substituent to a predetermined DNA sequence by homologous pairing for various applications, for example: producing sequence-specific strand scission(s), producing sequence-specific chemical modifications (e.g., base methylation, strand crosslinking), producing sequence-specific localization of polypeptides (e.g., topoisomerases, helicases, proteases), producing sequence-specific localization of polynucleotides (e.g., loading sites for transcription factors and/or RNA polymerase), and other applications.

It is another object of the present invention to provide methods for correcting a genetic mutation in an endogenous DNA target sequence, such as a sequence encoding an RNA or a protein. For example, the invention can be used to correct genetic mutations, such as base substitutions, additions, and/or deletions, by converting a mutant DNA sequence that encodes a non-functional, dysfunctional, and/or truncated polypeptide into a corrected DNA sequence that encodes a functional polypeptide (e.g., has a biological activity such as an enzymatic activity, hormone function, or other biological property). The methods and compositions of the invention may also be used to correct genetic mutations or dysfunctional alleles with genetic lesions in non-coding sequences (e.g., promoters, enhancers, silencers, origins of replication, splicing signals). In contradistinction, the invention also can be used to target DNA sequences for inactivating gene expression; a targeting polynucleotide can be employed to make a targeted base substitution, addition, and/or deletion in a structural or regulatory endogenous DNA sequence to alter expression of one or more genes, typically by knocking out at least one allele of a gene (i.e., making a mutant, nonfunctional allele). The invention can also be used to correct disease alleles, such as a human or non-human animal CFTR gene allele associated with cystic fibrosis, by producing a targeted alteration in the disease allele to correct a disease-causing lesion (e.g., a deletion).

It is a further object of the invention to provide methods and compositions for high-efficiency gene targeting of human genetic disease alleles, such as a CFTR allele associated with cystic fibrosis or an LDL receptor allele associated with familial hypercholesterolemia. In one aspect of the invention, targeting polynucleotides having at least one associated recombinase are targeted to cells in vivo (i.e., in an intact animal) by exploiting the advantages of a receptor-mediated uptake mechanism, such as an asialoglycoprotein receptor-mediated uptake process. In this variation, a targeting polynucleotide is associated with a recombinase and a cell-uptake component which enhances the uptake of the targeting polynucleotide-recombinase into cells of at least one cell type in an intact individual. For example, but not limitation, a cell-uptake component typically consists of: (1) a galactose-terminal (asialo-) glycoprotein (e.g., asialoorosomucoid) capable of being recognized and internalized by specialized receptors (asialoglycoprotein receptors) on hepatocytes in vivo, and (2) a polycation, such as poly-L-lysine, which binds to the targeting polynucleotide, usually by electrostatic interaction. Typically, the targeting polynucleotide is coated with recombinase and cell-uptake component simultaneously so that both recombinase and cell-uptake component bind to the targeting polynucleotide; alternatively, a targeting polynucleotide can be coated with recombinase prior to incubation with a cell-uptake component; alternatively the targeting polynucleotide can be coated with the cell-uptake component and introduced into cells contemporaneously with a separately delivered recombinase (e.g., by targeted liposomes containing one or more recombinase).

The invention also provides methods and compositions for diagnosis, treatment and prophylaxis of genetic diseases of animals, particularly mammals, wherein a recombinase and a targeting polynucleotide are used to produce a targeted sequence modification in a disease allele of an endogenous gene. The invention may also be used to produce targeted sequence modification(s) in a non-human animal, particularly a non-human mammal such as a mouse, which create(s) a disease allele in a non-human animal. Sequence-modified non-human animals harboring such a disease allele may provide useful models of human and veterinary disease(s). Alternatively, the methods and compositions of the invention can be used to provide nonhuman animals having homologously-targeted human disease alleles integrated into a non-human genome; such non-human animals may provide useful experimental models of human or other animal genetic disease, including neoplastic and other pathogenic diseases.

It is also an object of the invention to provide methods and compositions to introduce genes at a predetermined site in the chromosome. The invention may be used to introduce heterologous cDNA and/or genomic DNA sequences into the chromosome of non-human animals to allow expression and/or production of the heterologous gene.

It is also an object of the invention to provide methods and compositions for recombinase-enhanced positioning of a targeting polynucleotide to a homologous sequence in an endogenous chromosome to form a stable multistrand complex, and thereby alter expression of a predetermined gene sequence by interfering with transcription of sequence (s) adjacent to the multistrand complex. Recombinase(s) are used to ensure correct homologous pairing and formation of a stable multistrand complex, which may include a double-D loop structure. For example, a targeting polynucleotide coated with a recombinase may homologously pair with an endogenous chromosomal sequence in a structural or regulatory sequence of a gene and form a stable multistrand complex which may: (1) constitute a significant physical or chemical obstacle to formation of or procession of an active transcriptional complex comprising at least an RNA polymerase, or (2) alter the local chromatin structure so as to alter the transcription rate of gene sequences within about 1 to 500 kilobases of the multistrand complex.

It is another object of the invention to provide methods and compositions for treating or preventing acquired human and animal diseases, particularly parasitic or viral diseases, such as human hepatitis B virus (HBV) hepatitis, by targeting viral gene sequences with a recombinase-associated targeting polynucleotide and thereby inactivating said viral gene sequences and inhibiting viral-induced pathology.

It is a further object of the invention to provide compositions that contain exogenous targeting polynucleotides, complementary pairs of targeting polynucleotides, chemical substituents of such polynucleotides, and recombinase proteins used in the methods of the invention. Such compositions may include a targeting or cell-uptake components to facilitate intracellular uptake of a targeting polynucleotide, especially for in vivo gene therapy and gene modification.

In accordance with the above objects, the present invention provides methods for targeting and altering, by homologous recombination, a pre-selected target nucleic acid sequence in a procaryotic cell to make a targeted sequence modification. The methods comprise introducing into at least one procaryotic cell at least one recombinase and at least two single-stranded targeting polynucleotides, each of which are substantially complementary to each other and comprise a homology clamp that substantially corresponds to or is substantially complementary to a preselected target nucleic acid sequence.

In an additional aspect, the methods comprise adding to an extrachromosomal sequence at least one recombinase and at least two single-stranded targeting polynucleotides, each of which are substantially complementary to each other and comprise a homology clamp that substantially corresponds to or is substantially complementary to a preselected target nucleic acid sequence to form an altered extrachromosomal sequence. The recombinase is then removed and the altered sequence is introduced into a target cell.

In a further embodiment, the present invention provides methods of generating a library of variant nucleic acid sequences of a pre-selected target nucleic acid sequence in an extrachromosomal sequence. The method comprises adding to an extrachromosomal sequence at least one recombinase and a plurality of pairs of single-stranded targeting polynucleotides, which are substantially complementary to each other and each comprising a homology clamp that substantially corresponds to or is substantially complementary to a preselected target nucleic acid sequence. The plurality of pairs comprises a library of mismatches between the targeting polynucleotides and the target nucleic acid sequence, to form a library of altered extrachromosomal sequences.

In an additional aspect, the invention provides methods of generating a cellular library comprising variant nucleic acid sequences of a pre-selected target nucleic acid sequence. The methods comprise introducing into a population of target cells at least one recombinase and a plurality of pairs of single-stranded targeting polynucleotides which are substantially complementary to each other and each comprising a homology clamp that substantially corresponds to or is substantially complementary to a preselected target nucleic acid sequence. The plurality of pairs comprises a library of mismatches between the targeting polynucleotides and the target nucleic acid sequence, to form said cellular library comprising variant nucleic acid sequences.

In a further aspect, the invention provides methods of generating a cellular library comprising variant nucleic acid sequences of a pre-selected target nucleic acid sequence in an extrachromosomal sequence of a target cell. The methods comprises adding to an extrachromosomal sequence at least one recombinase and a plurality of pairs of single-stranded targeting polynucleotides which are substantially complementary to each other and each comprising a homology clamp that substantially corresponds to or is substantially complementary to a preselected target nucleic acid sequence. The plurality of pairs comprises a library of mismatches between the targeting polynucleotides and the target nucleic acid sequence, to form a plurality of altered extrachromosomal sequences. The recombinase is then removed and the altered sequences are introduced into a population of target cells to form the library of variant nucleic acid sequences.

The invention also provides compositions comprising at least one recombinase and a variant library comprising a plurality of pairs of single stranded targeting polynucleotides which are substantially complementary to each other and each comprising a homology clamp that substantially corresponds to or is substantially complementary to a pre-selected target nucleic acid sequence. The plurality of pairs comprises a library of mismatches between the targeting polynucleotides and the target nucleic acid sequence.

BRIEF DESCRIPTION OF THE DRAWINGS

FIGS. 1A–D. Homologous targeting of recA-coated chromosome 1 alpha-satellite polynucleotides in metabolically active cell nuclei. The homologously targeted biotinylated polynucleotides were visualized by addition of FITC-avidin followed by washing to remove unbound FITC. Signals were visualized using a Zeiss Confocal Laser Scanning Microscope (CLSM-10) with 488 nm argon laser beam illumination for FITC-DNA detection. FIG. 1A:—localized FITC-DNA signals in cell nucleus. FIG. 1C:—enhanced image of FITC-DNA signals in cell nucleus. FIG. 1B:—image of FITC-DNA signals overlaid on phase image of nucleus. FIG. 1D:—phase image of center of cell nucleus showing nucleoli. Note: all images except FIG. 1D: were photographed at same focus level (focus unchanged between these photos).

FIGS. 2A, 2B, 2C, 2D, 2E, 2F, 2G, 2H, 2I, 2J, 2K, and 2L. RecA protein-mediated native FISH in metabolically active cell nuclei. Hep-2 cell nuclei from cells encapsulated in agarose were incubated with RecA-coated biotinylated p53 DNA (A–I) or RecA-coated biotinylated chromosome 1 satellite III DNA probes (K–L). Panels B–I show FISH signals in digital images from serial CLSM optical sections of FITC-labeled p53 probe DNA incubated in metabolically active Hep-2 nuclei. The phase image of a representative nucleous in shown in Panel A and was sectioned by CLSM. Digital images in Panels B–H were serially overlaid upon one another to produce the composite digital image shown in Panel I containing all three FITC labeled p53 FISH signals. The effect of cssDNA probe concentration and RecA protein on efficiency of native dsDNA hybridization in metabolically active nuclei is shown in Panel J. The percentage of labeled RecA coated or uncoated p53 cssDNA is shown as a function of the amount of p53 DNA probe per hybridization reaction. Closed circles show hybridization reactions with RecA-coated p53 cssDNA probe, open triangles show control reactions without RecA protein coating of p53 cssDNA probe. Panel K shows the FISH digital image in Panel L overlaid onto the phase image.

FIG. 3. Genetic map of mammalian expression lacZ plasmid pMC1lacXpA with an 11 base insertion in Xba linker site.

FIG. 4. Genetic map of mammalian expression lacZ plasmid pMC1lacpA, with insertion mutation.

FIG. 5. PCR products and primers from the lacZ (β-galactosidase) gene sequence. The location of the 11 bp Xba linker is shown (SEQ ID NO:8).

FIG. 6. Tests for alteration of an insertion mutation in the lacZ gene of a eukaryotic expression vector. NIH 3T3 cells were needle microinjected with five types of plasmids: Two plasmids contained a wild-type β-galactosidase gene (pMC1lacpa or pSV-β-gal [Promega]); a plasmid with a mutant β-gal gene (pMC1lacXpa); pMC1lacXpa plasmid reacted with an uncoated wild-type 276-mer DNA; or pMC1lacXpa plasmid reacted and D-looped with RecA-coated wild-type 276-mer DNA. The wild-type 276-mer DNA was either coated or not with RecA protein in a standard coating reaction protocol (Sena and Zarling, supra). Following a 10-min RecA coating reaction, the complementary RecA-coated single-stranded 276-mers were incubated at 37° C. for 60 min. with the mutant target plasmid to allow hybrid formation. A 60 min incubation of the mutant target plasmid DNA with uncoated complementary single-stranded normal wild-type 276-mers was carried out as a control. The β-galactosidase activity in needle microinjected cells using the wild-type plasmids is shown for comparison. On average, about 50% of the total microinjected cells survived. The numbers of surviving cells scoring blue with the mutant plasmid RecA-treated and non-RecA-treated samples (3, 4 and 5) were compared with fourfold $X^2$ tests. The frequency of corrected blue cells in the RecA-treated sample (Sample 5; 6 out of 168) is significantly higher than that of either Sample 3 or Sample 4. The frequency of corrected RecA-treated blue cells in Sample 5 is significantly higher than that of Sample 4 at the 5% significance level ($X^2=3.76>X^2_{0.05}$). The frequency of corrected RecA-treated blue cells in Sample 5 is significantly higher than that of Sample 3 at the 1% significance level ($X^2=6.28>X^2_{0.01}$). When Sample 3 and 4 are combined and compared with Sample 5, the frequency of corrected blue cells in the RecA-treated Sample 5 is significantly higher than that of the combined sample at the 0.1% signficance level ($X^2=9.99>X^2_{0.001}$).

FIG. 8A. Analysis of DNA from cells electroporated or transfected with DNA encapsulated in a protein-lipid complex. Allele-specific PCR amplification of the 687/684 bp DNA fragment amplified in the first round with primers CF1 and oligo N (N) or oligo ΔF (ΔF). Ethidium bromide-stained 300 bp DNA fragment separated by electrophoresis in a 1% agarose gel. The DNA in each lane is as follows: lane 1, 100-bp marker DNA; lane 2, control 16HBE14o-cell DNA amplified with the CF1/N primer pair; lane 3, nontransfected ΣCFTE29o-cell DNA amplified with CF1/N primers; lane 4, nontransfected ΣCFTE29o-cell DNA amplified with CF1/ΔF primers; lane 5, DNA from ΣCFTE29o-cells electroporated with recA-coated 491-nucleotide fragments and amplified with CF1/N primers; lane 6, DNA from ΣCFTE29o-cells transfected with reCA-coated 491-nucleotide fragment encapsulated in a protein-lipid complex and amplified with CF1/N primers.

FIG. 8B. Autoradiographic analysis of the DNA in FIG. IIA transferred to Gene Screen Plus filters and hybridized with $^{32}$P-labeled oligo N probe. Samples in lanes 1–5 for the autoradiographic analysis are equivalent to samples in lanes 2–6 in FIG. IIA.

FIG. 10 depicts the scheme for the recombination assay used in Example 4.

FIG. 11 shows RecA mediated cssDNA targeting to dsDNA with deletions produces a mixed population of probe:target hybrids. The biotinylated cssDNA probes were denatured and coated with RecA at 37° C. as described in Material. The reaction mixture was incubated for 60 minutes at 37° C. All reactions were stopped by deproteinization with 1.2% SDS and separated by electrophoresis on a 20 cm×25 cm 1% agarose gel. The gel was run overnight at 30V then blotted onto a positively charged TropilonPlus (TROPIX) membrane. The DNA was monitored for the presence of unhybridized probe or probe:target hybrids using an alkaline phosphatase based chemiluminescent detection of biotin. When the membranes were exposed to X-ray film and developed, it is evident that cssDNA probes will hybridize to dsDNA targets which are completely homologous as well as dsDNA targets which contain a deletion (lanes 3 and 6, respectively). RecA mediated cssDNA targeting to completely homologous dsDNA (pRD.0) forms a probe:target hybrid whose electrophoretic mobility is comparable to the electrophoretic mobility of completely relaxed Form I DNA which is similar to the mobility of Form II DNA (lanes 3, 8, and 10), referred to as the rI* hybrid. RecA hybridization of mediated cssDNA to dsDNA containing a 59 base pair deletion (pRD.59), a probe:target hybrid that migrates to a position similar to Form I DNA (lane 6), referred to as the I* hybrid.

FIG. 12 shows data for the enhanced homologous recombination (EHR) of cssDNA probe:target hybrids in *E. coli*, as per Example 4. The homologously targeted probe:target hybrids have enhanced homologous recombination frequencies in recombination proficient cells. cssDNA probe:target hybrids formed as in the legend of FIG. 11 were introduced into RecA+ and RecA– E. coli as in FIG. 12. The molar ratio of cssDNA probe:target in the in vitro targeting reaction varied from 1:1 to 1:5.6. The % recombinant/total colonies is the percentage blue colonies in the total population of ampicillin-resistant colonies. Groups with 0% recombinants did not produce any blue colonies in at least $10^5$ plated colonies. Plasmid DNA was isolated from blue colonies that were serially propagated for three generations to determine if homologous recombination stably occurred in the lacZ gene.

FIGS. 13A–C shows double D-loop hybrids with internal homology clamps. FIG. 13A: Duplex target DNA (thin line) is completely homologous to the cssDNA probe (thick) and each probe strand can pair with its complementary strand in the target. FIG. 13B: Duplex target has a deletion with respect to the cssDNA probe. The deleted region is indicated with a dashed line. The region of the cssDNA probes homologous to the deleted region in the target can re-pair with each other forming a stable hybrid complex. FIG. 13C: Duplex target has an insertion (dashed line) with respect to the cssDNA probe. Structures on the left show the re-annealing of cssDNA probe or target strands to form internal homology clamps. Structures on the right show the presence of unpaired regions in comparable single D-loop hybrids.

FIGS. 14A and 14B. FIG. 14A depicts the Maps of Plasmids pRD.0 and pRD.59. Relative positions of cssDNA probes IP290 and CP443, PCR primers 1A and 4B, restriction endonuclease sites EcoRI, ScaI, and DraI are indicated. The alpha peptide sequence of the LacZ gene is indicated. Note the deletion (Δ) in pRD.59 is approximately equidistant from the ends of primers 1A and 4B. FIG. 14B). Time Course for cssDNA probe:target hybrid formation with linear dsDNA targets. Biotinylated, RecA coated cssDNA probe IP290 was hybridized as described to Sca1-digested plasmids pRD.0 and pRD.59 carrying 0 or 59 bp deletion, respectively at the EcoR1 site in pRD.0. Probe IP290 is completely homologous to pRD.0, but has a 59 bp insertion with respect to pRD.59.

FIGS. 15A–D depicts the formation of cssDNA probe target hybrids in linear dsDNA targets containing small deletions. FIG. 15A: Plasmid constructs and probes used in this study. A series of plasmids with defined deletions were constructed from the EcoR1 site of pRD.0 (pbluescriptIISK+ (Stratagene) as described in Example 5. Each plasmid is named for the size of the deletion, as indicated on the left. A series of cssDNA probes were labelled and constructed by PCR from various primers which flank the deleted region. Probes were made from either pRD.0 or the deleted plasmids and named for the size of the probe when made from pRD.0 (2960 bp). For example, p527 is 527 bp long. When the cssDNA probes are produced from pRD.0 and targeted to plasmids containing deletions, the probe is called IP527 to indicate that the probe has an insertion with respect to the target. When the probe is made from one of the targets with a deletion and then, targeted to pRD.0, the probe is called DP527 to indicate that the probe has a deletion with respect to pRD.0. Control probe CP443 is made from a region of pRD.0 that does not contain any insertions or deletions. The limits of the deleted regions in the plasmid DNA target are indicated by dashed line and the size limits of cssDNA probes are indicated by solid lines. FIG. 15: Biotinylated cssDNA probes IP527, IP407, and CP443 were coated with RecA protein and hybridized at 37° C. to a series of linear duplex DNA targets containing deletions ranging in size from 0 to 447 bp. The products of the targeting reaction were deproteinized and separated on a 1% TAE-agarose gel and then transferred to nylon membranes as described in Example 5. Biotinylated DNA was detected with a chemiluminescent substrate as described. The extent of hybrid product formation of FormIII DNA targets was determined by densitometry of the autoradiographs. The relative amount of hybrid formed between RecA coated cssDNA probes IP527 and IP407 is shown in (B). Error bars are indicated. The amount of probe:target hybrids formed with each target DNA was normalized by the amount of probe:target hybrids formed with control probe CP443 which hybridizes to the target away from the deletion site. FIG. 15C: Examples of the cssDNA probe:target hybrid formed with linear targets is shown in the autoradiogram. FIG. 15D: The difference in the percent hybrid formation between cssDNA probes IP527 and IP407 are plotted from the data shown in FIG. 15B.

FIG. 16 depicts that insertions and deletions have the same effect on the relative efficiency of probe:target hybrid formation. RecA-coated cssDNA probes IP215 made from pRD.0 was targeted to Sca1-digests of plasmids pRD.0, pRD.8, pRD.25, and pRD.59 and compared to similar reactions of DP215 cssDNA probes made from pRD.0, pRD.8, pRD.25, and pRD.59 and targeted to pRD.0. The effect of insertions in the cssDNA probe (dark line) is compared with deletions in the cssDNA probe (shaded line) of the same size. The relative level of hybrid formation for each cssDNA probe with a heterologous target is normalized by the level of hybridization with the homologous target, respectively. The data represents an average of three experiments. Error bars are indicated.

FIGS. 17A, 17B and 17C. FIG. 17A depict the formation of stable Double-D-Loop hybrids in linear dsDNA targets containing large deletions. Biotinylated cssDNA probe IP1246 was coated with RecA protein and targeted to Sca1 digests of the indicated plasmids as described herein. The relative amount of hybrid formation formed between RecA-coated cssDNA probes and plasmids with deletions ranging from 0–967 bp was normalized to the amount of probe:target hybrids formed with control probe CP443. Autoradiograph (17A) shows the biotinylated cssDNA probes or probe:target hybrids. The position of the untargeted Sca1-digested (FormIII) marker for each of the plasmids are indicated on the right. The relative level of hybrid formation (B) of each of the bands in (A) was normalized to the level of hybrid formation with control cssDNA probe CP443 as described herein. The relative position of the cssDNA probes with respect to the position of the deletion in the target DNA is shown in (C).

FIGS. 18A, 18B, 18C and 18D depict the formation of restriction endonuclease sites in probe:target hybrids. The probe:target hybrids formed between probe IP290 and pRD.0 and pRD.59 targets were deproteinized by extraction with chloroform:phenol:isoamyl alcohol and chloroform. Restriction enzyme treated DNA samples were incubated with EcoRI for three hours before separation on a 1% agarose gel and transferred onto a nylon membrane. The ethidium bromide stained DNA of the products of the targeting reactions formed between cssDNA probe IP290 and circular plasmid targets pRD.0 or pRD.59 (A and B) and autoradiographs showing the positions of biotinylated cssDNA probe:target hybrids (C and D) are shown. The positions of form I and form III markers of pRD.0 are shown on the right. The positions of the pRD59 hybrids I* (form I) and rI* (relaxed) are shown on the left.

FIG. 19 depicts the thermal stability of relaxed and non-relaxed probe:target hybrids. The RecA mediated cssDNA targeting reaction was performed with the cssDNA probe IP290 and the dsDNA target pRD.59 as described herein. The probe:target hybrids were deproteinized with 1.2% SDS and then incubated for 5 minutes at the indicated temperatures. The thermally melted products were then separated on a 1% agarose gel and blotted onto a positively charged Tropilon membrane. Autoradiograph shows the position of biotinylated cssDNA probe:target hybrids I* (formI) and rI* (relaxed) as shown on the left.

FIGS. 20A and 20B. The organization of the mouse OTC gene. Sequence of cssDNA probes and PCR primers used in this study are indicated. Sizes of the exons in basepairs are indicated. The relative position of PCR primers M9, M8 and M11 are shown. B) Map of plasmid pTAOTC1. A 250 bp fragment containing the normal OTC exon4 sequence (SEQ ID NO:9) and surrounding introns were cloned into the EcoRV site of pbluescript SK (+)(Stratagene).

FIG. 21. Sequence analysis of exon4 of the mouse OTC gene in founder mice. PCR amplification of genomic DNA from tail biopsies of a pool of all of the homozygous (spf-ash/spf-ash) females used as egg donors and each indicated individual founder mice were sequenced using cycle sequencing with the M11 primer (Cyclist kit, Stratagene). The DNA sequence surrounding the spf-ash locus (arrow; SEQ ID NO:10) in the OTC gene is shown.

FIG. 22. Germline transmission of OTC+ allele corrected by EHR. The inheritance patterns of the OTC alleles are depicted. Legend indicates the genotype and/or phenotype of the F0, F1, and F2 mice produced from microinjected zygotes obtained from the cross of homozygous (spf-ash/spf-ash) mutant females and normal males (top). The genotype of F0 and F1 animals were determined by DNA sequencing and the typing of F2 animals as deduced by phenotype. Control cross A of (hemizygous spf-ash/Y) mutant F0 male with normal (+/+) females and control cross B of heterozygous (spf-ash/+) F1 females with a normal male are indicated. The number below the boxes or circles indicate the total number of mice of each type produced from each cross. Total numbers of mice counted are representative of 2–4 litters. Mouse #213 and #1014 (noted by arrow) are F1 animals that carry a germline transmitted gene corrected allele from mosaic HR gene corrected male mouse #16.

FIG. 23. Germline transmission of corrected allele of F0 male #16. Pictures of F1 progeny from the cross of mouse #16 with homozygous (spf-ash/spf-ash) females (top). This cross produced several pups with spf-ash mutant phenotypes (middle) and one F1 pup (#1014) with a normal phenotype. Three views of mouse #1014 are shown (bottom). All of the F1 animals were two weeks old at the time of photography.

DEFINITIONS

Figure 7A:
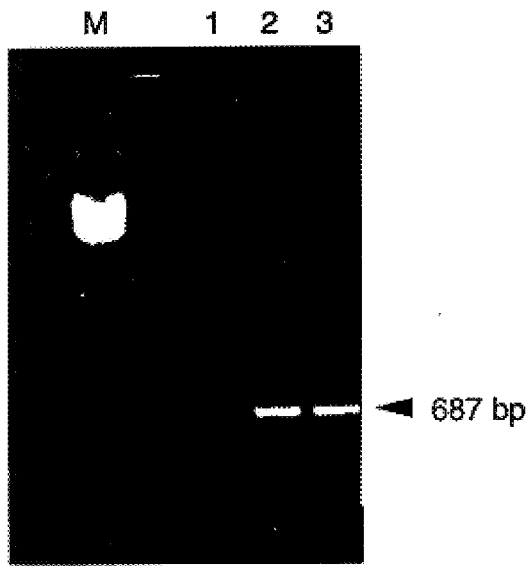
FIG. 7A. Southern hybridization analysis of the 687-bp fragment amplified from genomic DNA. Electrophoretic migration of a 687-bp DNA fragment generated with primers CF1 and CF6 from genomic DNA of ΣCFTE29o-cells which were capillary needle-microinjected with the 491-nucleotide DNA fragment in the presence of recA (lane 2) or transfected as a protein-DNA-lipid complex where the 491-nucleotide fragments were coated with recA (+; lane 3). The control DNA was amplified from nontransfected ΣCFTE29o-cultures (lane 1).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis*, 2nd Edition, E. S. Golub and D. R. Green, Eds., Sinauer Associates, Sunderland, Mass. (1991), which is incorporated herein by reference).

By "nucleic acid", "oligonucleotide", and "polynucleotide" or grammatical equivalents herein means at least two nucleotides covalently linked together. A nucleic acid of the present invention will generally contain phosphodiester bonds, although in some cases nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). These modifications of the ribose-phosphate backbone or bases may be done to facilitate the addition of other moieties such as chemical constituents, including 2'O-methyl and 5' modified substituents, as discussed below, or to increase the stability and half-life of such molecules in physiological environments.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo-and ribo-nucleotides, and any combination of bases, including uracil, adenine, thymine, cytosine, guanine, inosine, xathanine and hypoxathanine, etc. Thus, for example, chimeric DNA-RNA molecules may be used such as described in Cole-Strauss et al., Science 273:1386 (1996) and Yoon et al., PNAS USA 93:2071 (1996), both of which are hereby incorporated by reference.

In general, the targeting polynucleotides may comprise any number of structures, as long as the changes do not substantially effect the functional ability of the targeting polynucleotide to result in homologous recombination. For example, recombinase coating of alternate structures should still be able to occur.

As used herein, the terms "predetermined endogenous DNA sequence" and "predetermined target sequence" refer to polynucleotide sequences contained in a target cell. Such sequences include, for example, chromosomal sequences (e.g., structural genes, regulatory sequences including promoters and enhancers, recombinatorial hotspots, repeat sequences, integrated proviral sequences, hairpins, palindromes), episomal or extrachromosomal sequences (e.g., replicable plasmids or viral replication intermediates) including chloroplast and mitochondrial DNA sequences. By "predetermined" or "pre-selected" it is meant that the target sequence may be selected at the discretion of the practitioner on the basis of known or predicted sequence information, and is not constrained to specific sites recognized by certain site-specific recombinases (e.g., FLP recombinase or CRE recombinase). In some embodiments, the predetermined endogenous DNA target sequence will be other than a naturally occurring germline DNA sequence (e.g., a transgene, parasitic, mycoplasmal or viral sequence). An exogenous polynucleotide is a polynucleotide which is transferred into a target cell but which has not been replicated in that host cell; for example, a virus genome polynucleotide that enters a cell by fusion of a virion to the cell is an exogenous polynucleotide, however, replicated copies of the viral polynucleotide subsequently made in the infected cell are endogenous sequences (and may, for example, become integrated into a cell chromosome). Similarly, transgenes which are microinjected or transfected into a cell are exogenous polynucleotides, however integrated and replicated copies of the transgene(s) are endogenous sequences.

The term "corresponds to" is used herein to mean that a polynucleotide sequence is homologous (i.e., may be similar or identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. As outlined below, preferably, the homology is at least 70%, preferably 85%, and more preferably 95% identical. Thus, the complementarity between two single-stranded targeting polynucleotides need not be perfect. For illustration, the nucleotide sequence "TATAC" corresponds to a reference sequence "TATAC" and is perfectly complementary to a reference sequence "GTATA".

The terms "substantially corresponds to" or "substantial identity" or "homologous" as used herein denotes a characteristic of a nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. "Substantially complementary" as used herein refers to a sequence that is complementary to a sequence that substantially corresponds to a reference sequence. In general, targeting efficiency increases with the length of the targeting polynucleotide portion that is substantially complementary to a reference sequence present in the target DNA.

"Specific hybridization" is defined herein as the formation of hybrids between a targeting polynucleotide (e.g., a polynucleotide of the invention which may include substitutions, deletion, and/or additions as compared to the predetermined target DNA sequence) and a predetermined target DNA, wherein the targeting polynucleotide preferentially hybridizes to the predetermined target DNA such that, for example, at least one discrete band can be identified on a Southern blot of DNA prepared from target cells that contain the target DNA sequence, and/or a targeting polynucleotide in an intact nucleus localizes to a discrete chromosomal location characteristic of a unique or repetitive sequence. In some instances, a target sequence may be present in more than one target polynucleotide species (e.g., a particular target sequence may occur in multiple members of a gene family or in a known repetitive sequence). It is evident that optimal hybridization conditions will vary depending upon the sequence composition and length(s) of the targeting polynucleotide(s) and target(s), and the experimental method selected by the practitioner. Various guidelines may be used to select appropriate hybridization conditions (see, Maniatis et al., *Molecular Cloning: A Laboratory Manual* (1989), 2nd Ed., Cold Spring Harbor, N.Y. and Berger and Kimmel, *Methods in Enzymology, Volume* 152. *Guide to Molecular Cloning Techniques* (1987), Academic Press, Inc., San Diego, Calif., which are incorporated herein by reference. Methods for hybridizing a targeting polynucleotide to a discrete chromosomal location in intact nuclei are provided herein in the Detailed Description.

The term "naturally-occurring" as used herein as applied to an object refers to the fact that an object can be found in nature. For example, a polynucleotide sequence that is present in an organism (including viruses) that can be isolated from a source in nature and which has not been intentionally modified by man in the laboratory is naturally-occurring.

A metabolically-active cell is a cell, comprising an intact nucleoid or nucleus, which, when provided nutrients and incubated in an appropriate medium carries out DNA synthesis and RNA for extended periods (e.g., at least 12–24 hours). Such metabolically-active cells are typically undifferentiated or differentiated cells capable or incapable of further cell division (although non-dividing cells many undergo nuclear division and chromosomal replication), although stem cells and progenitor cells are also metabolically-active cells.

As used herein, the term "disease allele" refers to an allele of a gene which is capable of producing a recognizable disease. A disease allele may be dominant or recessive and may produce disease directly or when present in combination with a specific genetic background or pre-existing pathological condition. A disease allele may be present in the gene pool or may be generated de novo in an individual by somatic mutation. For example and not limitation, disease to alleles include: activated oncogenes, a sickle cell anemia allele, a Tay-Sachs allele, a cystic fibrosis allele, a Lesch-Nyhan allele, a retinoblastoma-susceptibility allele, a Fabry's disease allele, and a Huntington's chorea allele. As used herein, a disease allele encompasses both alleles associated with human diseases and alleles associated with recognized veterinary diseases. For example, the ΔF508 CFTR allele in a human disease allele which is associated with cystic fibrosis in North Americans.

As used herein, the term "cell-uptake component" refers to an agent which, when bound, either directly or indirectly, to a targeting polynucleotide, enhances the intracellular uptake of the targeting polynucleotide into at least one cell type (e.g., hepatocytes). A cell-uptake component may include, but is not limited to, the following: specific cell surface receptors such as a galactose-terminal (asialo-) glycoprotein capable of being internalized into hepatocytes via a hepatocyte asialoglycoprotein receptor, a polycation (e.g., poly-L-lysine), and/or a protein-lipid complex formed with the targeting polynucleotide. Various combinations of the above, as well as alternative cell-uptake components will be apparent to those of skill in the art and are provided in the published literature.

Detailed Description

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgenesis. Generally enzymatic reactions, oligonucleotide synthesis, oligonucleotide modification, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

Transgenic mice are derived according to Hogan, et al., "Manipulating the Mouse Embryo: A Laboratory Manual", Cold Spring Harbor Laboratory (1988) which is incorporated herein by reference.

Embryonic stem cells are manipulated according to published procedures (Teratocarcinomas and embryonic stem cells: a practical approach, E. J. Robertson, ed., IRL Press, Washington, D.C., 1987; Zjilstra et al., Nature 342:435–438 (1989); and Schwartzberg et al., Science 246:799–803 (1989), each of which is incorporated herein by reference).

Zygotes are manipulated according to known procedures; for example see U.S. Pat. No. 4,873,191, Brinster et al., PNAS 86:7007 (1989); Susulic et al., J. Biol. Chem. 49:29483 (1995), and Cavard et al., Nucleic Acids Res. 16:2099 (1988), hereby incorporated by reference.

Oligonucleotides can be synthesized on an Applied Bio Systems oligonucleotide synthesizer according to specifications provided by the manufacturer. Modified oligonucleotides and peptide nucleic acids are made as is generally known in the art.

The present invention provides methods for targeting and altering, by homologous recombination, a pre-selected target nucleic acid sequence in a target cell, to make targeted sequence modifications. The methods comprise introducing into the target cells a recombinase and at least two single-stranded targeting polynucleotides which are substantially complementary to each other. The targeting polynucleotides each comprise at least one homology clamp that substantially corresponds to or is substantially complementary to the preselected target nucleic acid sequence. The target cells are then screened to identify target cells containing the targeted sequence modification.

Targeting Polynucleotides

Targeting polynucleotides may be produced by chemical synthesis of oligonucleotides, nick-translation of a double-stranded DNA template, polymerase chain-reaction amplification of a sequence (or ligase chain reaction amplification), purification of prokaryotic or target cloning vectors harboring a sequence of interest (e.g., a cloned cDNA or genomic clone, or portion thereof) such as plasmids, phagemids, YACs, cosmids, bacteriophage DNA, other viral DNA or replication intermediates, or purified restriction fragments thereof, as well as other sources of single and double-stranded polynucleotides having a desired nucleotide sequence. Targeting polynucleotides are generally ssDNA or dsDNA, most preferably two complementary single-stranded DNAs.

Targeting polynucleotides are generally at least about 2 to 100 nucleotides long, preferably at least about 5- to 100 nucleotides long, at least about 250 to 500 nucleotides long, more preferably at least about 500 to 2000 nucleotides long, or longer; however, as the length of a targeting polynucleotide increases beyond about 20,000 to 50,000 to 400,000 nucleotides, the efficiency or transferring an intact targeting polynucleotide into the cell decreases. The length of homology may be selected at the discretion of the practitioner on the basis of the sequence composition and complexity of the predetermined endogenous target DNA sequence(s) and guidance provided in the art, which generally indicates that 1.3 to 6.8 kilobase segments of homology are preferred (Hasty et al. (1991) Molec. Cell. Biol. 11: 5586; Shulman et al. (1990) Molec. Cell. Biol. 10: 4466, which are incorporated herein by reference). Targeting polynucleotides have at least one sequence that substantially corresponds to, or is substantially complementary to, a predetermined endogenous DNA sequence (i.e., a DNA sequence of a polynucleotide located in a target cell, such as a chromosomal, mitochondrial, chloroplast, viral, episomal, or mycoplasmal polynucleotide). Such targeting polynucleotide sequences serve as templates for homologous pairing with the predetermined endogenous sequence(s), and are also referred to herein as homology clamps. In targeting polynucleotides, such homology clamps are typically located at or near the 5' or 3' end, preferably homology clamps are internally or located at each end of the polynucleotide (Berinstein et al. (1992) Molec. Cell. Biol. 12: 360, which is incorporated herein by reference). Without wishing to be bound by any particular theory, it is believed that the addition of recombinases permits efficient gene targeting with targeting polynucleotides having short (i.e., about 50 to 1000 basepair long) segments of homology, as well as with targeting polynucleotides having longer segments of homology.

Therefore, it is preferred that targeting polynucleotides of the invention have homology clamps that are highly homologous to the predetermined target endogenous DNA sequence(s), most preferably isogenic. Typically, targeting polynucleotides of the invention have at least one homology clamp that is at least about 18 to 35 nucleotides long, and it is preferable that homology clamps are at least about 20 to 100 nucleotides long, and more preferably at least about 100–500 nucleotides long, although the degree of sequence homology between the homology clamp and the targeted sequence and the base composition of the targeted sequence will determine the optimal and minimal clamp lengths (e.g., G-C rich sequences are typically more thermodynamically stable and will generally require shorter clamp length). Therefore, both homology clamp length and the degree of sequence homology can only be determined with reference to a particular predetermined sequence, but homology clamps generally must be at least about 12 nucleotides long and must also substantially correspond or be substantially complementary to a predetermined target sequence. Preferably, a homology clamp is at least about 12, and preferably at least about 50 nucleotides long and is identical to or complementary to a predetermined target sequence. Without wishing to be bound by a particular theory, it is believed that the addition of recombinases to a targeting polynucleotide enhances the efficiency of homologous recombination between homologous, nonisogenic sequences (e.g., between an exon 2 sequence of a albumin gene of a Balb/c mouse and a homologous albumin gene exon 2 sequence of a C57/BL6 mouse), as well as between isogenic sequences.

The formation of heteroduplex joints is not a stringent process; genetic evidence supports the view that the classical phenomena of meiotic gene conversion and aberrant meiotic segregation result in part from the inclusion of mismatched base pairs in heteroduplex joints, and the subsequent correction of some of these mismatched base pairs before replication. Observations on recA protein have provided information on parameters that affect the discrimination of relatedness from perfect or near-perfect homology and that affect the inclusion of mismatched base pairs in heteroduplex joints. The ability of recA protein to drive strand exchange past all single base-pair mismatches and to form extensively mismatched joints in superhelical DNA reflect its role in recombination and gene conversion. This errorprone process may also be related to its role in mutagenesis. RecA-mediated pairing reactions involving DNA of φX174 and G4, which are about 70 percent homologous, have yielded homologous recombinants (Cunningham et al. (1981) Cell 24: 213), although recA preferentially forms homologous joints between highly homologous sequences, and is implicated as mediating a homology search process between an invading DNA strand and a recipient DNA strand, producing relatively stable heteroduplexes at regions of high homology. Accordingly, it is the fact that recombinases can drive the homologous recombination reaction between strands which are significantly, but not perfectly, homologous, which allows gene conversion and the modification of target sequences. Thus, targeting polynucleotides may be used to introduce nucleotide substitutions, insertions and deletions into an endogeneous DNA sequence, and thus the corresponding amino acid substitutions, insertions and deletions in proteins expressed from the endogeneous DNA sequence.

In a preferred embodiment, two substantially complementary targeting polynucleotides are used. In one embodiment, the targeting polynucleotides form a double stranded hybrid, which may be coated with recombinase, although when the recombinase is recA, the loading conditions may be somewhat different from those used for single stranded nucleic acids.

In a prefered embodiment, two substantially complementary single-stranded targeting polynucleotides are used. The two complementary single-stranded targeting polynucleotides are usually of equal length, although this is not required. However, as noted below, the stability of the four strand hybrids of the invention is putatively related, in part, to the lack of significant unhybridized single-stranded nucleic acid, and thus significant unpaired sequences are not preferred. Furthermore, as noted above, the complementarity between the two targeting polynucleotides need not be perfect. The two complementary single-stranded targeting polynucleotides are simultaneously or contemporaneously introduced into a target cell harboring a predetermined endogenous target sequence, generally with at lease one recombinase protein (e.g., recA). Under most circumstances, it is preferred that the targeting polynucleotides are incubated with recA or other recombinase prior to introduction into a target cell, so that the recombinase protein(s) may be "loaded" onto the targeting polynucleotide(s), to coat the nucleic acid, as is described below. Incubation conditions for such recombinase loading are described infra, and also in U.S. Ser. No. 07/755,462, filed Sep. 4, 1991, U.S. Pat. No. 5,273,881; U.S. Ser. No. 07/910,791, filed Jul. 9, 1992, abandoned; and U.S. Ser. No. 07/520,321, filed May 7, 1990 U.S. Pat. No. 5,223,414, each of which is incorporated herein by reference. A targeting polynucleotide may contain a sequence that enhances the loading process of a recombinase, for example a recA loading sequence is the recombinogenic nucleation sequence poly[d(A-C)], and its complement, poly[d(G-T)]. The duplex sequence poly[d(A-C).d(G-T)$_n$, where n is from 5 to 25, is a middle repetitive element in target DNA.

There appears to be a fundamental difference in the stability of RecA-protein-mediated D-loops formed between one single-stranded DNA (ssDNA) probe hybridized to negatively supercoiled DNA targets in comparison to relaxed or linear duplex DNA targets. Internally located dsDNA target sequences on relaxed linear DNA targets hybridized by ssDNA probes produce single D-loops, which are unstable after removal of RecA protein (Adzuma, Genes Devel. 6:1679 (1992); Hsieh et al, PNAS USA 89:6492 (1992); Chiu et al., Biochemistry 32:13146 (1993)). This probe DNA instability of hybrids formed with linear duplex DNA targets is most probably due to the incoming ssDNA probe W-C base pairing with the complementary DNA strand of the duplex target and disrupting the base pairing in the other DNA strand. The required high free-energy of maintaining a disrupted DNA strand in an unpaired ssDNA conformation in a protein-free single-D-loop apparently can only be compensated for either by the stored free energy inherent in negatively supercoiled DNA targets or by base pairing initiated at the distal ends of the joint DNA molecule, allowing the exchanged strands to freely intertwine.

However, the addition of a second complementary ssDNA to the three-strand-containing single-D-loop stabilizes the deproteinized hybrid joint molecules by allowing W-C base pairing of the probe with the displaced target DNA strand. The addition of a second RecA-coated complementary ssDNA (cssDNA) strand to the three-strand containing single D-loop stabilizes deproteinized hybrid joints located away from the free ends of the duplex target DNA (Sena & Zarling, Nature Genetics 3:365 (1993); Revet et al. J. Mol. Biol. 232:779 (1993); Jayasena and Johnston, J. Mol. Bio. 230:1015 (1993)). The resulting four-stranded structure, named a double D-loop by analogy with the three-stranded single D-loop hybrid has been shown to be stable in the absence of RecA protein. This stability likely occurs because the restoration of W-C basepairing in the parental duplex would require disruption of two W-C basepairs in the double-D-loop (one W-C pair in each heteroduplex D-loop). Since each base-pairing in the reverse transition (double-D-loop to duplex) is less favorable by the energy of one W-C basepair, the pair of cssDNA probes are thus kinetically trapped in duplex DNA targets in stable hybrid structures. The stability of the double-D loop joint molecule within internally located probe:target hybrids is an intermediate stage prior to the progression of the homologous recombination reaction to the strand exchange phase. The double D-loop permits isolation of stable multistranded DNA recombination intermediates.

In addition, when the targeting polynucleotides are used to generate insertions or deletions in an endogeneous nucleic acid sequence, the use of two complementary single-stranded targeting polynucleotides allows the use of internal homology clamps as depicted in FIG. 13. The use of internal homology clamps allows the formation of stable deproteinized cssDNA:probe target hybrids with homologous DNA sequences containing either relatively small or large insertions and deletions within a homologous DNA target. Without being bound by theory, it appears that these probe:target hybrids, with heterologous inserts in the cssDNA probe, are stabilized by the re-annealing of cssDNA probes to each other within the double-D-loop hybrid, forming a novel DNA structure with an internal homology clamp. Similarly stable double-D-loop hybrids formed at internal sites with heterologous inserts in the linear DNA targets (with respect to the cssDNA probe) are equally stable. Because cssDNA probes are kinetically trapped within the duplex target, the multi-stranded DNA intermediates of homologous DNA pairing are stabilized and strand exchange is facilitated.

In a preferred embodiment, the length of the internal homology clamp (i.e. the length of the insertion or deletion) is from about 1 to 50% of the total length of the targeting polynucleotide, with from about 1 to about 20% being preferred and from about 1 to about 10% being especially preferred, although in some cases the length of the deletion or insertion may be significantly larger. As for the targeting homology clamps, the complementarity within the internal homology clamp need not be perfect.

The invention may also be practiced with individual targeting polynucleotides which do not comprise part of a complementary pair. In each case, a targeting polynucleotide is introduced into a target cell simultaneously or contemporaneously with a recombinase protein, typically in the form of a recombinase coated targeting polynucleotide as outlined herein (i.e., a polynucleotide pre-incubated with recombinase wherein the recombinase is noncovalently bound to the polynucleotide; generally referred to in the art as a nucleoprotein filament).

A targeting polynucleotide used in a method of the invention typically is a single-stranded nucleic acid, usually a DNA strand, or derived by denaturation of a duplex DNA, which is complementary to one (or both) strand(s) of the target duplex nucleic acid. Thus, one of the complementary single stranded targeting polynucleotides is complementary to one strand of the endogeneous target sequence (i.e. Watson) and the other complementary single stranded targeting polynucleotide is complementary to the other strand of the endogeneous target sequence (i.e. Crick). The homology clamp sequence preferably contains at least 90–95% sequence homology with the target sequence, to insure sequence-specific targeting of the targeting polynucleotide to the endogenous DNA target. Each single-stranded targeting polynucleotide is typically about 50–600 bases long, although a shorter or longer polynucleotide may also be employed. Alternatively, targeting polynucleotides may be prepared in single-stranded form by oligonucleotide synthesis methods, which may first require, especially with larger targeting polynucleotides, formation of subfragments of the targeting polynucleotide, typically followed by splicing of the subfragments together, typically by enzymatic ligation.

Recombinase Proteins

Recombinases are proteins that, when included with an exogenous targeting polynucleotide, provide a measurable increase in the recombination frequency and/or localization frequency between the targeting polynucleotide and an endogenous predetermined DNA sequence. Thus, in a preferred embodiment, increases in recombination frequency from the normal range of $10^{-8}$ to $10^{-4}$, to $10^{-4}$ to $10^1$, preferably $10^{-3}$ to $10^1$, and most preferably $10^{-2}$ to $10^1$, may be acheived.

In the present invention, recombinase refers to a family of RecA-like recombination proteins all having essentially all or most of the same functions, particularly: (i) the recombinase protein's ability to properly bind to and position targeting polynucleotides on their homologous targets and (ii) the ability of recombinase protein/targeting polynucleotide complexes to efficiently find and bind to complementary endogenous sequences. The best characterized recA protein is from *E. coli,* in addition to the wild-type protein a number of mutant recA-like proteins have been identified (e.g., recA803; see Madiraju et al., PNAS USA 85(18):6592 (1988); Madiraju et al, Biochem. 31:10529 (1992); Lavery et al., J. Biol. Chem. 267:20648 (1992)). Further, many organisms have recA-like recombinases with strand-transfer activities (e.g., Fugisawa et al., (1985) *Nucl. Acids Res.* 13: 7473; Hsieh et al., (1986) *Cell* 44: 885; Hsieh et al., (1989) *J. Biol. Chem.* 264: 5089; Fishel et al., (1988) *Proc. Natl. Acad. Sci. (USA)* 85: 3683; Cassuto et al., (1987) *Mol. Gen. Genet.* 208: 10; Ganea et al., (1987) *Mol. Cell Biol.* 7: 3124; Moore et al., (1990) *J. Biol. Chem.* 19: 11108; Keene et al., (1984) *Nucl. Acids Res.* 12: 3057; Kimeic, (1984) *Cold Spring Harbor Svmp.* 48: 675; Kmeic, (1986) *Cell* 44: 545; Kolodner et al., (1987) *Proc. Natl. Acad. Sci. USA* 84: 5560; Sugino et al., (1985) *Proc. Natl. Acad. Sci. USA* 85: 3683; Halbrook et al., (1989) *J. Biol. Chem.* 264: 21403; Eisen et al., (1988) *Proc. Natl. Acad. Sci. USA* 85: 7481; McCarthy et al., (1988) *Proc. Natl. Acad. Sci. USA* 85: 5854; Lowenhaupt et al., (1989) *J. Biol. Chem.* 264: 20568, which are incorporated herein by reference. Examples of such recombinase proteins include, for example but not limitation: recA, recA803, uvsX, and other recA mutants and recA-like recombinases (Roca, A. I. (1990) *Crit. Rev. Biochem. Molec. Biol.* 25: 415), sep1 (Kolodner et al. (1987) *Proc. Natl. Acad. Sci. (U.S.A.)* 84:5560; Tishkoff et al. *Molec. Cell. Biol.* 11:2593), RuvC (Dunderdale et al. (1991) *Nature* 354: 506), DST2, KEM1, XRN1 (Dykstra et al. (1991) *Molec. Cell. Biol.* 11:2583), STPα/DST1 (Clark et al. (1991) *Molec. Cell. Biol.* 11:2576), HPP-1 (Moore et al. (1991) *Proc. Natl. Acad. Sci. (U.S.A.)* 88:9067), other target recombinases (Bishop et al. (1992) *Cell* 69: 439; Shinohara et al. (1992) *Cell* 69: 457); incorporated herein by reference. RecA may be purified from *E. coli* strains, such as *E. coli* strains JC12772 and JC15369 (available from A. J. Clark and M. Madiraju, University of California-Berkeley, or purchased commercially). These strains contain the recA coding sequences on a "runaway" replicating plasmid vector present at a high copy numbers per cell. The recA803 protein is a high-activity mutant of wild-type recA. The art teaches several examples of recombinase proteins, for example, from Drosophila, yeast, plant, human, and non-human mammalian cells, including proteins with biological properties similar to recA (i.e., recA-like recombinases), such as Rad51 from mammals and yeast, and Pk-rec (see Rashid et al., Nucleic Acid Res. 25(4):719 (1997), hereby incorporated by reference). In addition, the recombinase may actually be a complex of proteins, i.e. a "recombinosome". In addition, included within the definition of a recombinase are portions or fragments of recombinases which retain recombinase biological activity, as well as variants or mutants of wild-type recombinases which retain biological activity, such as the *E. coli* recA803 mutant with enhanced recombinase activity.

In a preferred embodiment, recA or rad51 is used. For example, recA protein is typically obtained from bacterial strains that overproduce the protein: wild-type *E. coli* recA protein and mutant recA803 protein may be purified from such strains. Alternatively, recA protein can also be purchased from, for example, Pharmacia (Piscataway, N.J.).

RecA proteins, and its homologs, form a nucleoprotein filament when it coats a single-stranded DNA. In this nucleoprotein filament, one monomer of recA protein is bound to about 3 nucleotides. This property of recA to coat single-stranded DNA is essentially sequence independent, although particular sequences favor initial loading of recA onto a polynucleotide (e.g., nucleation sequences). The nucleoprotein filament(s) can be formed on essentially any DNA molecule and can be formed in cells (e.g., mammalian cells), forming complexes with both single-stranded and double-stranded DNA, although the loading conditions for dsDNA are somewhat different than for ssDNA.

Recombinase Coating of Targeting Polynucleotides

The conditions used to coat targeting polynucleotides with recombinases such as recA protein and ATPγS have been described in commonly assigned U.S. Ser. No. 07/910, 791, filed Jul. 9, 1992; U.S. Ser. No. 07/755,462, filed Sep. 4, 1991; and U.S. Ser. No. 07/520,321, filed May 7, 1990, each incorporated herein by reference. The procedures below are directed to the use of *E. coli* recA, although as will be appreciated by those in the art, other recombinases may be used as well. Targeting polynucleotides can be coated using GTPγS, mixes of ATPγS with rATP, rGTP and/or dATP, or dATP or rATP alone in the presence of an rATP generating system (Boehringer Mannheim). Various mixtures of GTPγS, ATPγS, ATP, ADP, dATP and/or rATP or other nucleosides may be used, particularly preferred are mixes of ATPγS and ATP or ATPγS and ADP.

RecA protein coating of targeting polynucleotides is typically carried out as described in U.S. Ser. No. 07/910,791, filed Jul. 9, 1992 and U.S. Ser. No. 07/755,462, filed Sep. 4, 1991, which are incorporated herein by reference. Briefly, the targeting polynucleotide, whether double-stranded or single-stranded, is denatured by heating in an aqueous solution at 95–100° C. for five minutes, then placed in an ice bath for 20 seconds to about one minute followed by centrifugation at 0° C. for approximately 20 sec, before use. When denatured targeting polynucleotides are not placed in a freezer at −20° C. they are usually immediately added to standard recA coating reaction buffer containing ATPγS, at room temperature, and to this is added the recA protein. Alternatively, recA protein may be included with the buffer components and ATPγS before the polynucleotides are added. RecA coating of targeting polynucleotide(s) is initiated by incubating polynucleotide-recA mixtures at 37° C. for 10–15 min. RecA protein concentration tested during reaction with polynucleotide varies depending upon polynucleotide size and the amount of added polynucleotide, and the ratio of recA molecule:nucleotide preferably ranges between about 3:1 and 1:3. When single-stranded polynucleotides are recA coated independently of their homologous polynucleotide strands, the mM and μM concentrations of ATPγS and recA, respectively, can be reduced to one-half those used with double-stranded targeting polynucleotides (i.e., recA and ATPγS concentration ratios are usually kept constant at a specific concentration of individual polynucleotide strand, depending on whether a single- or double-stranded polynucleotide is used).

RecA protein coating of targeting polynucleotides is normally carried out in a standard 1×RecA coating reaction buffer. 10×RecA reaction buffer (i.e., 10×AC buffer) consists of: 100 mM Tris acetate (pH 7.5 at 37° C.), 20 mM magnesium acetate, 500 mM sodium acetate, 10 mM DTT, and 50% glycerol). All of the targeting polynucleotides, whether double-stranded or single-stranded, typically are denatured before use by heating to 95–100° C. for five minutes, placed on ice for one minute, and subjected to centrifugation (10,000 rpm) at 0° C. for approximately 20 seconds (e.g., in a Tomy centrifuge). Denatured targeting polynucleotides usually are added immediately to room temperature RecA coating reaction buffer mixed with ATPγS and diluted with double-distilled $H_2O$ as necessary.

A reaction mixture typically contains the following components: (i) 0.2–4.8 mM ATPγS; and (ii) between 1–100 ng/μl of targeting polynucleotide. To this mixture is added about 1–20 μl of recA protein per 10–100 μl of reaction mixture, usually at about 2–10 mg/ml (purchased from Pharmacia or purified), and is rapidly added and mixed. The final reaction volume-for RecA coating of targeting polynucleotide is usually in the range of about 10–500 μl. RecA coating of targeting polynucleotide is usually initiated by incubating targeting polynucleotide-RecA mixtures at 37° C. for about 10–15 min.

RecA protein concentrations in coating reactions varies depending upon targeting polynucleotide size and the amount of added targeting polynucleotide: recA protein concentrations are typically in the range of 5 to 50 μM. When single-stranded targeting polynucleotides are coated with recA, independently of their complementary strands, the concentrations of ATPγS and recA protein may optionally be reduced to about one-half of the concentrations used with double-stranded targeting polynucleotides of the same length: that is, the recA protein and ATPγS concentration ratios are generally kept constant for a given concentration of individual polynucleotide strands.

The coating of targeting polynucleotides with recA protein can be evaluated in a number of ways. First, protein binding to DNA can be examined using band-shift gel assays (McEntee et al., (1981) *J. Biol. Chem.* 256: 8835). Labeled polynucleotides can be coated with recA protein in the presence of ATPγS and the products of the coating reactions may be separated by agarose gel electrophoresis. Following incubation of recA protein with denatured duplex DNAs the recA protein effectively coats single-stranded targeting polynucleotides derived from denaturing a duplex DNA. As the ratio of recA protein monomers to nucleotides in the targeting polynucleotide increases from 0, 1:27, 1:2.7 to 3.7:1 for 121-mer and 0, 1:22, 1:2.2 to 4.5:1 for 159-mer, targeting polynucleotide's electrophoretic mobility decreases, i.e., is retarded, due to recA-binding to the targeting polynucleotide. Retardation of the coated polynucleotide's mobility reflects the saturation of targeting polynucleotide with recA protein. An excess of recA monomers to DNA nucleotides is required for efficient recA coating of short targeting polynucleotides (Leahy et al., (1986) *J. Biol. Chem.* 261: 954).

A second method for evaluating protein binding to DNA is in the use of nitrocellulose fiber binding assays (Leahy et al., (1986) *J. Biol. Chem.* 261:6954; Woodbury, et al., (1983) *Biochemistry* 22(20):4730–4737. The nitrocellulose filter binding method is particularly useful in determining the dissociation-rates for protein:DNA complexes using labeled DNA. In the filter binding assay, DNA:protein complexes are retained on a filter while free DNA passes through the filter. This assay method is more quantitative for dissociation-rate determinations because the separation of DNA:protein complexes from free targeting polynucleotide is very rapid.

Alternatively, recombinase protein(s) (prokaryotic, eukaryotic or endogeneous to the target cell) may be exogenously induced or administered to a target cell simultaneously or contemporaneously (i.e., within about a few hours) with the targeting polynucleotide(s). Such administration is typically done by micro-injection, although electroporation, lipofection, and other transfection methods known in the art may also be used. Alternatively, recombinase-proteins may be produced in vivo. For example, they may be produced from a homologous or heterologous expression cassette in a transfected cell or transgenic cell, such as a transgenic totipotent cell (e.g. a fertilized zygote) or an embryonal stem cell (e.g., a murine ES cell such as AB-1) used to generate a transgenic non-human animal line or a somatic cell or a pluripotent hematopoietic stem cell for reconstituting all or part of a particular stem cell population (e.g. hematopoietic) of an individual. Conveniently, a heterologous expression cassette includes a modulatable promoter, such as an ecdysone-inducible promoter-enhancer combination, an estrogen-induced promoter-enhancer combination, a CMV promoter-enhancer, an insulin gene promoter, or other cell-type specific, developmental stage-specific, hormone-inducible, or other modulatable promoter construct so that expression of at least one species of recombinase protein from the cassette can by modulated for transiently producing recombinase(s) in vivo simultaneous or contemporaneous with introduction of a targeting polynucleotide into the cell. When a hormone-inducible promoter-enhancer combination is used, the cell must have the required hormone receptor present, either naturally or as a consequence of expression a co-transfected expression vector encoding such receptor. Alternatively, the recombinase may be endogenous and produced in high levels. In this embodiment, preferably in eukaryotic target cells such as tumor cells, the target cells produce an elevated level of recombinase. In other embodiments the level of recombinase may be induced by DNA damaging agents, such as mitomycin C, UV or γ-irradiation. Alternatively, recombinase levels may be elevated by transfection of a plasmid encoding the recombinase gene into the cell.

Cell-Uptake Components

A targeting polynucleotide of the invention may optionally be conjugated, typically by covalently or preferably noncovalent binding, to a cell-uptake component. Various methods have been described in the art for targeting DNA to specific cell types. A targeting polynucleotide of the invention can be conjugated to essentially any of several cell-uptake components known in the art. For targeting to hepatocytes, a targeting polynucleotide can be conjugated to an asialoorosomucoid (ASOR)-poly-L-lysine conjugate by methods described in the art and incorporated herein by reference (Wu G Y and Wu C H (1987) *J. Biol. Chem.* 262:4429; Wu G Y and Wu C H (1988) *Biochemistry* 27:887; Wu G Y and Wu C H (1988) *J. Biol. Chem.* 263:14621; Wu G Y and Wu C H (1992) *J. Biol. Chem.* 267: 12436; Wu et al. (1991) *J. Biol. Chem.* 266: 14338; and Wilson et al. (1992) *J. Biol. Chem.* 267: 963, WO92/06180; WO92/05250; and WO91/17761, which are incorporated herein by reference).

Alternatively, a cell-uptake component may be formed by incubating the targeting polynucleotide with at least one lipid species and at least one protein species to form protein-lipid-polynucleotide complexes consisting essentially of the targeting polynucleotide and the lipid-protein cell-uptake component. Lipid vesicles made according to Feigner (WO91/17424, incorporated herein by reference) and/or cationic lipidization (WO91/16024, incorporated herein by reference) or other forms for polynucleotide administration (EP 465,529, incorporated herein by reference) may also be employed as cell-uptake components. Nucleases may also be used.

In addition to cell-uptake components, targeting components such as nuclear localization signals may be used, as is known in the art.

Homologous Pairing of Targeting Polynucleotides Having Chemical Substituents

In addition to recombinase and cellular uptake components, the targeting polynucleotides may include chemical substituents. Exogenous targeting polynucleotides that have been modified with appended chemical substituents may be introduced along with recombinase (e.g., recA) into a metabolically active target cell to homologously pair with a predetermined endogenous DNA target sequence in the cell. In a preferred embodiment, the exogenous targeting polynucleotides are derivatized, and additional chemical substituents are attached, either during or after polynucleotide synthesis, respectively, and are thus localized to a specific endogenous target sequence where they produce an alteration or chemical modification to a local DNA sequence. Preferred attached chemical substituents include, but are not limited to: cross-linking agents (see Podyminogin et al., Biochem. 34:13098 (1995) and 35:7267 (1996), both of which are hereby incorporated by reference), nucleic acid cleavage agents, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, labels, base-modification agents, agents which normally bind to nucleic acids such as labels, etc. (see for example Afonina et al., PNAS USA 93:3199 (1996), incorporated herein by reference) immunoglobulin chains, and oligonucleotides. Iron/EDTA chelates are particularly preferred chemical substituents where local cleavage of a DNA sequence is desired (Hertzberg et al. (1982) *J. Am. Chem. Soc.* 104: 313; Hertzberg and Dervan (1984) *Biochemistry* 23: 3934; Taylor et al. (1984) *Tetrahedron* 40: 457; Dervan, PB (1986) *Science* 232: 464, which are incorporated herein by reference). Further preferred are groups that prevent hybridization of the complementary single stranded nucleic acids to each other but not to unmodified nucleic acids; see for example Kutryavin et al., Biochem. 35:11170 (1996) and Woo et al., Nucleic Acid. Res. 24(13):2470 (1996), both of which are incorporated by reference. 2'-O methyl groups are also preferred; see Cole-Strauss et al., Science 273:1386 (1996); Yoon et al., PNAS 93:2071 (1996)). Additional preferred chemical substitutents include labeling moieties, including fluoroscent labels. Preferred attachment chemistries include: direct linkage, e.g., via an appended reactive amino group (Corey and Schultz (1988) *Science* 238:1401, which is incorporated herein by reference) and other direct linkage chemistries, although streptavidin/biotin and digoxigenin/antidigoxigenin antibody linkage methods may also be used. Methods for linking chemical substituents are provided in U.S. Pat. Nos. 5,135,720, 5,093,245, and 5,055, 556, which are incorporated herein by reference. Other linkage chemistries may be used at the discretion of the practitioner.

Typically, a targeting polynucleotide of the invention is coated with at least one recombinase and is conjugated to a cell-uptake component, and the resulting cell targeting complex is contacted with a target cell under uptake conditions (e.g., physiological conditions) so that the targeting polynucleotide and the recombinase(s) are internalized in the target cell. A targeting polynucleotide may be contacted simultaneously or sequentially with a cell-uptake component and also with a recombinase; preferably the targeting polynucleotide is contacted first with a recombinase, or with a mixture comprising both a cell-uptake component and a recombinase under conditions whereby, on average, at least about one molecule of recombinase is noncovalently attached per targeting polynucleotide molecule and at least about one cell-uptake component also is noncovalently attached. Most preferably, coating of both recombinase and cell-uptake component saturates essentially all of the available binding sites on the targeting polynucleotide. A targeting polynucleotide may be preferentially coated with a cell-uptake component so that the resultant targeting complex comprises, on a molar basis, more cell-uptake component than recombinase(s). Alternatively, a targeting polynucleotide may be preferentially coated with recombinase(s) so that the resultant targeting complex comprises, on a molar basis, more recombinase(s) than cell-uptake component.

Cell-uptake components are included with recombinase-coated targeting polynucleotides of the invention to enhance the uptake of the recombinase-coated targeting polynucleotide(s) into cells, particularly for in vivo gene targeting applications, such as gene therapy to treat genetic diseases, including neoplasia, and targeted homologous recombination to treat viral infections wherein a viral sequence (e.g., an integrated hepatitis B virus (HBV) genome or genome fragment) may be targeted by homologous sequence targeting and inactivated. Alternatively, a targeting polynucleotide may be coated with the cell-uptake component and targeted to cells with a contemporaneous or simultaneous administration of a recombinase (e.g., liposomes or immunoliposomes containing a recombinase, a viral-based vector encoding and expressing a recombinase).

Once the recombinase-targeting polynucleotide compositions are formulated, they are introduced or administered into target cells. The administration is typically done as is known for the administration of nucleic acids into cells, and, as those skilled in the art will appreciate, the methods may depend on the choice of the target cell. Suitable methods include, but are not limited to, microinjection, electroporation, lipofection, etc. By "target cells" herein is meant prokaryotic or eukaryotic cells. Suitable prokaryotic cells include, but are not limited to, bacteria such as *E. coli*, Bacillus species, and the extremophile bacteria such as thermophiles, etc. Preferably, the procaryotic target cells are recombination competent. Suitable eukaryotic cells include, but are not limited to, fungi such as yeast and filamentous fungi, including species of Aspergillus, Trichoderma, and Neurospora; plant cells including those of corn, sorghum, tobacco, canola, soybean, cotton, tomato, potato, alfalfa, sunflower, etc.; and animal cells, including fish, birds and mammals. Suitable fish cells include, but are not limited to, those from species of salmon, trout, tulapia, tuna, carp, flounder, halobut, swordfish, cod and zebrafish. Suitable bird cells include, but are not limited to, those of chickens, ducks, quail, pheasants and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes.

In a preferred embodiment, procaryotic cells are used. In this embodiment, a pre-selected target DNA sequence is chosen for alteration. Preferably, the pre-selected target DNA sequence is contained within an extrachromosomal sequence. By "extrachromosomal sequence" herein is meant a sequence separate from the chromosomal or genomic sequences. Preferred extrachromosomal sequences include plasmids (particularly procaryotic plasmids such as bacterial plasmids), p1 vectors, viral genomes, yeast, bacterial and mammalian artificial chromosomes (YAC, BAC and MAC, respectively), and other autonomously self-replicating sequences, although this is not required. As described herein, a recombinase and at least two single stranded targeting polynucleotides which are substantially complementary to each other, each of which contain a homology clamp to the target sequence contained on the extrachromosomal sequence, are added to the extrachromosomal sequence, preferably in vitro. The two single stranded targeting polynucleotides are preferably coated with recombinase, and at least one of the targeting polynucleotides contain at least one nucleotide substitution, insertion or deletion. The targeting polynucleotides then bind to the target sequence in the extrachromosomal sequence to effect homologous recombination and form an altered extrachromosomal sequence which contains the substitution, insertion or deletion. The altered extrachromosomal sequence is then introduced into the procaryotic cell using techniques known in the art. Preferably, the recombinase is removed prior to introduction into the target cell, using techniques known in the art. For example, the reaction may be treated with proteases such as proteinase K, detergents such as SDS, and phenol extraction (including phenol:chloroform:isoamyl alcohol extraction). These methods may also be used for eukaryotic cells.

Alternatively, the pre-selected target DNA sequence is a chromosomal sequence. In this embodiment, the recombinase with the targeting polynucleotides are introduced into the target cell, preferably eukaryotic target cells. In this embodiment, it may be desirable to bind (generally non-covalently) a nuclear localization signal to the targeting polynucleotides to facilitate localization of the complexes in the nucleus. See for example Kido et al., Exper. Cell Res. 198:107–114 (1992), hereby expressly incorporated by reference. The targeting polynucleotides and the recombinase function to effect homologous recombination, resulting in altered chromosomal or genomic sequences.

In a preferred embodiment, eukaryotic cells are used. For making transgenic non-human animals (which include homologously targeted non-human animals) embryonal stem cells (ES cells) and fertilized zygotes are preferred. In a preferred embodiment, embryonal stem cells are used. Murine ES cells, such as AB-1 line grown on mitotically inactive SNL76/7 cell feeder layers (McMahon and Bradley, *Cell* 62: 1073–1085 (1990)) essentially as described (Robertson, E. J. (1987) in *Teratocarcinomas and Embryonic Stem Cells: A Practical Approach*. E. J. Robertson, ed. (oxford: IRL Press), p. 71–112) may be used for homologous gene targeting. Other suitable ES lines include, but are not limited to, the E14 line (Hooper et al. (1987) *Nature* 326: 292–295), the D3 line (Doetschman et al. (1985) *J. Embryol. Exp. Morph.* 87: 21–45), and the CCE line (Robertson et al. (1986) *Nature* 323: 445–448). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal).

The pluripotence of any given ES cell line can vary with time in culture and the care with which it has been handled. The only definitive assay for pluripotence is to determine whether the specific population of ES cells to be used for targeting can give rise to chimeras capable of germline transmission of the ES genome. For this reason, prior to gene targeting, a portion of the parental population of AB-1 cells is injected into C57B1/6J blastocysts to ascertain whether the cells are capable of generating chimeric mice with extensive ES cell contribution and whether the majority of these chimeras can transmit the ES genome to progeny.

In a preferred embodiment, non-human zygotes are used, for example to make transgenic animals, using techniques known in the art (see U.S. Pat. No. 4,873,191). Preferred zygotes include, but are not limited to, animal zygotes, including fish, avian and mammalian zygotes. Suitable fish zygotes include, but are not limited to, those from species of salmon, trout, tuna, carp, flounder, halibut, swordfish, cod, tulapia and zebrafish. Suitable bird zygotes include, but are not limited to, those of chickens, ducks, quail, pheasant, turkeys, and other jungle fowl and game birds. Suitable mammalian zygotes include, but are not limited to, cells from horses, cows, buffalo, deer, sheep, rabbits, rodents such as mice, rats, hamsters and guinea pigs, goats, pigs, primates, and marine mammals including dolphins and whales. See Hogan et al., Manipulating the Mouse Embryo (A Laboratory Manual), 2nd Ed. Cold Spring Harbor Press, 1994, incorporated by reference.

The vectors containing the DNA segments of interest can be transferred into the host cell by well-known methods, depending on the type of cellular host. For example, microinjection is commonly utilized for target cells, although calcium phosphate treatment, electroporation, lipofection, biolistics or viral-based transfection also may be used. Other methods used to transform mammalian cells include the use of Polybrene, protoplast fusion, and others (see, generally, Sambrook et al. Molecular Cloning: A Laboratory Manual, 2d ed., 1989, Cold Spring Harbor Laboratory Press, Cold Spring Harbor, N.Y., which is incorporated herein by reference). Direct injection of DNA and/or recombinase-coated targeting polynucleotides into target cells, such as skeletal or muscle cells also may be used (Wolff et al. (1990) *Science* 247: 1465, which is incorporated herein by reference).

Targeting of Endogenous DNA Sequences

Once made and administered to a target host cell, the compositions of the invention find use in a number of applications, including the site directed modification of endogeneous sequences within any target cell, the creation of transgenic plants and animals, and the use of the compositions to do site-directed mutagenesis or modifications of target sequences.

Generally, any predetermined endogenous DNA sequence, such as a gene sequence, can be altered by homologous recombination (which includes gene conversion) with an exogenous targeting polynucleotides (such as a complementary pair of single-stranded targeting polynucleotides). The target polynucleotides have at least one homology clamp which substantially corresponds to or is substantially complementary to a predetermined endogenous DNA target sequence and are introduced with a recombinase (e.g., recA) into a target cell having the predetermined endogenous DNA sequence. Typically, a targeting polynucleotide (or complementary polynucleotide pair) has a portion or region having a sequence that is not present in the preselected endogenous targeted sequence(s) (i.e., a nonhomologous portion or mismatch) which may be as small as a single mismatched nucleotide, several mismatches, or may span up to about several kilobases or more of nonhomologous sequence. Generally, such nonhomologous portions are flanked on each side by homology clamps, although a single flanking homology clamp may be used. Nonhomologous portions are used to make insertions, deletions, and/or replacements in a predetermined endogenous targeted DNA sequence, and/or to make single or multiple nucleotide substitutions in a predetermined endogenous target DNA sequence so that the resultant recombined sequence (i.e., a targeted recombinant endogenous sequence) incorporates some or all of the sequence information of the nonhomologous portion of the targeting polynucleotide(s). Thus, the nonhomologous regions are used to make variant sequences, i.e. targeted sequence modifications. Additions and deletions may be as small as 1 nucleotide or may range up to about 2 to 4 kilobases or more. In this way, site directed directed modifications may be done in a variety of systems for a variety of purposes.

In a preferred application, a targeting polynucleotide is used to repair a mutated sequence of a structural gene by replacing it or converting it to a wild-type sequence (e.g., a sequence encoding a protein with a wild-type biological activity). For example, such applications could be used to convert a sickle cell trait allele of a hemoglobin gene to an allele which encodes a hemoglobin molecule that is not susceptible to sickling, by altering the nucleotide sequence encoding the β-subunit of hemoglobin so that the codon at position 6 of the β-subunit is converted Valβ6-->Gluβ6 (Shesely et al. (1991) op.cit.). Other genetic diseases can be corrected, either partially or totally, by replacing, inserting, and/or deleting sequence information in a disease allele using appropriately selected exogenous targeting polynucleotides. For example but not for limitation, the ΔF508 deletion in the human CFTR gene can be corrected by targeted homologous recombination employing a recA-coated targeting polynucleotide of the invention.

For many types of in vivo gene therapy to be effective, a significant number of cells must be correctly targeted, with a minimum number of cells having an incorrectly targeted recombination event. To accomplish this objective, the combination of: (1) a targeting polynucleotide(s), (2) a recombinase (to provide enhanced efficiency and specificity of correct homologous sequence targeting), and (3) a cell-uptake component (to provide enhanced cellular uptake of the targeting polynucleotide), provides a means for the efficient and specific targeting of cells in vivo, making in vivo homologous sequence targeting, and gene therapy, practicable.

Several disease states may be amenable to treatment or prophylaxis by targeted alteration of heptocytes in vivo by homologous gene targeting. For example and not for limitation, the following diseases, among others not listed, are expected to be amenable to targeted gene therapy: hepatocellular carcinoma, HBV infection, familial hypercholesterolemia (LDL receptor defect), alcohol sensitivity (alcohol dehydrogenase and/or aldehyde dehydrogenase insufficiency), hepatoblastoma, Wilson's disease, congenital hepatic porphyrias, inherited disorders of hepatic metabolism, ornithine transcarbamylase (OTC) alleles, HPRT alleles associated with Lesch Nyhan syndrome, etc. Where targeting of hepatic cells in vivo is desired, a cell-uptake component consisting essentially of an asialoglycoprotein-poly-L-lysine conjugate is preferred. The targeting complexes of the invention which may be used to target hepatocytes in vivo take advantage of the significantly increased targeting efficiency produced by association of a targeting polynucleotide with a recombinase which, when combined with a cell-targeting method such as that of WO92/05250 and/or Wilson et al. (1992) *J. Biol. Chem.* 267:963, provide a highly efficient method for performing in vivo homologous sequence targeting in cells, such as hepatocytes.

In a preferred embodiment, the methods and compositions of the invention are used for gene inactivation. That is, in addition to correcting disease alleles, exogenous targeting polynucleotides can be used to inactivate, decrease or alter the biological activity of one or more genes in a cell (or transgenic nonhuman animal). This finds particular use in the generation of animal models of disease states, or in the elucidation of gene function and activity, similar to "knock out" experiments. These techniques may be used to eliminate a biological function; for example, a galT gene (alpha galactosyl transferase genes) associated with the xenoreactivity of animal tissues in humans may be disrupted to form transgenic animals (e.g. pigs) to serve as organ transplantation sources without associated hyperacute rejection responses. Alternatively, the biological activity of the wild-type gene may be either decreased, or the wild-type activity altered to mimic disease states. This includes genetic manipulation of non-coding gene sequences that affect the transcription of genes, including, promoters, repressors, enhancers and transcriptional activating sequences.

Once the specific target genes to be modified are selected, their sequences may be scanned for possible disruption sites (convenient restriction sites, for example). Plasmids are engineered to contain an appropriately sized gene sequence with a deletion or insertion in the gene of interest and at least one flanking homology clamp which substantially corresponds or is substantially complementary to an endogenous target DNA sequence. Vectors containing a targeting polynucleotide sequence are typically grown in *E. coli* and then isolated using standard molecular biology methods, or may be synthesized as oligonucleotides. Direct targeted inactivation which does not require vectors may also be done. When using microinjection procedures it may be preferable to use a transfection technique with linearized sequences containing only modified target gene sequence and without vector or selectable sequences. The modified gene site is such that a homologous recombinant between the exogenous targeting polynucleotide and the endogenous DNA target sequence can be identified by using carefully chosen primers and PCR, followed by analysis to detect if PCR products specific to the desired targeted event are present (Erlich et al., (1991) *Science* 252: 1643, which is incorporated herein by reference). Several studies have already used PCR to successfully identify and then clone the desired transfected cell lines (Zimmer and Gruss, (1989) *Nature* 338: 150; Mouellic et al., (1990) *Proc. Natl. Acad. Sci. USA* 87: 4712; Shesely et al., (1991) *Proc. Natl. Acad. Sci. USA* 88: 4294, which are incorporated herein by reference). This approach is very effective when the number of cells receiving exogenous targeting polynucleotide(s) is high (i.e., with microinjection, or with liposomes) and the treated cell populations are allowed to expand to cell groups of approximately $1 \times 10^4$ cells (Capecchi, (1989) *Science* 244: 1288). When the target gene is not on a sex chromosome, or the cells are derived from a female, both alleles of a gene can be targeted by sequential inactivation (Mortensen et al., (1991) *Proc. Natl. Acad. Sci. USA* 88: 7036).

In addition, the methods of the present invention are useful to add exogeneous DNA sequences, such as exogeneous genes or extra copies of endogeneous genes, to an organism. As for the above techniques, this may be done for a number of reasons, including: to alleviate disease states, for example by adding one or more copies of a wild-type gene or add one or more copies of a therapeutic gene; to create disease models, by adding disease genes such as oncogenes or mutated genes or even just extra copies of a wild-type gene; to add therapeutic genes and proteins, for example by adding tumor suppressor genes such as p53, Rb1, Wt1, NF1, NF2, and APC, or other therapeutic genes; to make superior transgenic animals, for example superior livestock; or to produce gene products such as proteins, for example for protein production, in any number of host cells. Suitable gene products include, but are not limited to, Rad51, alpha-antitrypsin, antithrombin III, alpha glucosidase, collagen, proteases, viral vaccines, tissue plaminogen activator, monoclonal antibodies, Factors VIII, IX, and X, glutamic acid decarboxylase, hemoglobin, prostaglandin receptor, lactoferrin, calf intestine alkaline phosphatase, CFTR, human protein C, porcine liver esterase, urokinase, and human serum albumin.

Thus, in a preferred embodiment, the targeted sequence modification creates a sequence that has a biological activity or encodes a polypeptide having a biological activity. In a preferred embodiment, the polypeptide is an enzyme with enzymatic activity.

In addition to fixing or creating mutations involved in disease states, a preferred embodiment utilizes the methods of the present invention to create novel genes and gene products. Thus, fully or partially random alterations can be incorporated into genes to form novel genes and gene products, to produce rapidly and efficiently a number of new products which may then be screened, as will be appreciated by those in the art.

In a preferred embodiment, the compositions and methods of the invention are useful in site-directed mutagenesis techniques to create any number of specific or random changes at any number of sites or regions within a target sequence (either nucleic acid or protein sequence), similar to traditional site-directed mutagenesis techniques such as cassette mutagenesis and PCR mutagenesis. Thus, for example, the techniques and compositions of the invention may be used to generate site specific variants in any number of systems, including *E. coli,* Bacillus, Archebacteria, Thermus, yeast (Sacchromyces and Pichia), insect cells (Spodoptera, Trichoplusia, Drosophila), Xenopus, rodent cell lines including CHO, NIH 3T3 and primate cell lines including COS, or human cells, including HT1080 and BT474, which are traditionally used to make variants. The techniques can be used to make specific changes, or random changes, at a particular site or sites, within a particular region or regions of the sequence, or over the entire sequence.

In this and other embodiments, suitable target sequences include nucleic acid sequences encoding therapeutically or commercially relevant proteins, including, but not limited to, enzymes (proteases, recombinases, lipases, kinases, carbohydrases, isomerases, tautomerases, nucleases etc.), hormones, receptors, transcription factors, growth factors, cytokines, globin genes, immunosupppressive genes, tumor suppressors, oncogenes, complement-activating genes, milk proteins (casein, $\alpha$-lactalbumin, $\beta$-lactoglobulin, bovine and human serum albumin), immunoglobulins, milk proteins, and pharmaceutical proteins and vaccines.

In a preferred embodiment, the methods of the invention are used to generate pools or libraries of variant nucleic acid sequences, and cellular libraries containing the variant libraries. Thus, in this embodiment, a plurality of targeting polynucleotides are used. The targeting polynucleotides each have at least one homology clamp that substantially corresponds to or is substantially complementary to the target sequence. Generally, the targeting polynucleotides are generated in pairs; that is, pairs of two single stranded targeting polynucleotides that are substantially complementary to each other are made (i.e. a Watson strand and a Crick strand). However, as will be appreciated by those in the art, less than a one to one ratio of Watson to Crick strands may be used; for example, an excess of one of the single stranded target polynucleotides (i.e. Watson) may be used. Preferably, sufficient numbers of each of Watson and Crick strands are used to allow the majority of the targeting polynucleotides to form double D-loops, which are preferred over single D-loops as outlined above. In addition, the pairs need not have perfect complementarity; for example, an excess of one of the single stranded target polynucleotides (i.e. Watson), which may or may not contain mismatches, may be paired to a large number of variant Crick strands, etc. Due to the random nature of the pairing, one or both of any particular pair of single-stranded targeting polynucleotides may not contain any mismatches. However, generally, at least one of the strands will contain at least one mismatch.

The plurality of pairs preferably comprise a pool or library of mismatches. The size of the library will depend on the number of residues to be mutagenized, as will be appreciated by those in the art. Generally, a library in this instance preferably comprises at least 40% different mismatches, with at least 30% mismatches being preferred and at least 10% being particularly preferred. That is, the plurality of pairs comprise a pool of random and preferably degenerate mismatches over some regions or all of the entire targeting sequence. As outlined herein, "mismatches" include substitutions, insertions and deletions. Thus, for example, a pool of degenerate variant targeting polynucleotides covering some, or preferably all, possible mismatches over some region are generated, as outlined above, using techniques well known in the art. Preferably, but not required, the variant targeting polynucleotides each comprise only one or a few mismatches (less than 10), to allow complete multiple randomization, as outlined below.

As will be appreciated by those in the art, the introduction of a pool of variant targeting polynucleotides (in combination with recombinase) to a target sequence, either in vitro to an extrachromosomal sequence or in vivo to a chromosomal or extrachromosomal sequence, can result in a large number of homologous recombination reactions occuring over time. That is, any number of homologous recombination reactions can occur on a single target sequence, to generate a wide variety of single and multiple mismatches within a single target sequence, and a library of such variant target sequences, most of which will contain mismatches and be different from other members of the library. This thus works to generate a library of mismatches.

In a preferred embodiment, the variant targeting polynucleotides are made to a particular region or domain of a sequence (i.e. a nucleotide sequence that encodes a particular protein domain). For example, it may be desirable to generate a library of all possible variants of a binding domain of a protein, without affecting a different biologically functional domain, etc. Thus, the methods of the present invention find particular use in generating a large number of different variants within a particular region of a sequence, similar to cassette mutagenesis but not limited by sequence length. In addition, two or more regions may also be altered simultaneously using these techniques. Suitable domains include, but are not limited to, kinase domains, nucleotide-binding sites, DNA binding sites, signaling domains, receptor binding domains, transcriptional activating regions, promoters, origins, leader sequences, terminators, localization signal domains, and, in immunoglobulin genes, the complementaity determining regions (CDR), Fc, $V_H$ and $V_L$.

In a preferred embodiment, the variant targeting polynucleotides are made to the entire target sequence. In this way, a large number of single and multiple mismatches may be made in an entire sequence.

Thus for example, the methods of the invention may be used to create superior recombinant reporter genes such as lacZ and green fluorescent protein (GFP); superior antibiotic and drug resistance genes; superior recombinase genes; superior recombinant vectors; and other superior recombinant genes and proteins, including immunoglobulins, vaccines or other proteins with therapeutic value. For example, targeting polynucleotides containing any number of alterations may be made to one or more functional or structural domains of a protein, and then the products of homologous recombination evaluated.

Once made and administered to target cells, the target cells may be screened to identify a cell that contains the targeted sequence modification. This will be done in any number of ways, and will depend on the target gene and targeting polynucleotides as will be appreciated by those in the art. The screen may be based on phenotypic, biochemical, genotypic, or other functional changes, depending on the target sequence. In an additional embodiment, as will be appreciated by those in the art, selectable markers or marker sequences may be included in the targeting polynucleotides to facilitate later identification.

In a preferred embodiment, kits containing the compositions of the invention are provided. The kits include the compositions, particularly those of libraries or pools of degenerate cssDNA probes, along with any number of reagents or buffers, including recombinases, buffers, ATP, etc.

The broad scope of this invention is best understood with reference to the following examples, which are not intended to limit the invention in any manner. All references cited herein are expressly incorporated by reference.

Experimental Examples

EXAMPLE 1

Homologous Targeting of recA-Coated Chemically-Modified Polynucleotides in Cells Homologously targeted exogenous targeting polynucleotides specifically target human DNA sequences in intact nuclei of metabolically active cells. RecA-coated complementary exogenous targeting polynucleotides were introduced into metabolically active human cells encapsulated in agarose microbeads and permeabilized to permit entry of DNA/protein complexes using the Jackson-Cook method (Cook, P. R. (1984) *EMBO J.* 3: 1837; Jackson and Cook (1985) *EMBO J.* 4: 919; Jackson and Cook (1985) *EMBO J.* 4: 913; Jackson and Cook (1986) *J. Mol. Biol.* 192: 65; Jackson et al. (1988) *J. Cell. Sci.* 90: 365, which are incorporated herein by reference). These experiments were designed to specifically target homologous DNA sequences with recA protein in intact nuclei of metabolically active human HEp-2 cells.

Jackson and Cook previously demonstrated that the nuclear membranes of human or other cells may be permeabilized without loss of metabolic function of the cells are first encapsulated in a gel of agarose microbeads. The agarose microbead coat contains the cell constituents and preserves native conformation of chromosomal DNA, while permitting diffusion of macromolecules into and out of the cell compartment. Wittig et al.(1991) *Proc. Natl. Acad. Sci. (U.S.A.)*, 88: 2259, which is incorporated herein by reference, demonstrated that monoclonal antibodies directed against left-handed Z-DNA could be diffused into these agarose-embedded cells, and that the antibodies were specifically targeted to chromosomal sequences and conformations. In a similar manner, we incubated biotin- or FITC-labeled complementary DNA targeting polynucleotides coated with recA with agarose-coated cell nuclei and verified the correct homologous targeting of the exogenous targeting polynucleotides to specific predetermined human DNA sequences in cell nuclei of metabolically active cells.

RecA-mediated homologous gene targeting with complementary oligonucleotides in intact human cell nuclei was verified directly by homologous targeting using targeting polynucleotides that were biotinylated. These were subsequently labeled with a fluorescent reporter compound to verify homologous pairing at specific locations having the predetermined sequence(s). RecA-coated targeting polynucleotides for human chromosome 1 pericentrometric alpha-satellite DNA sequences were specifically targeted to chromosome 1 centromere sequences in living human cell nuclei that were permeabilized and suspended in agarose.

In these experiments, recA-coated biotinylated exogenous targeting polynucleotides containing homologous sequences to human chromosome 1 alpha satellite DNA were incubated with human HEp-2 cells. The cells were embedded in agarose, then treated with standard buffers (according to Jackson and Cook, op.cit.) to remove the cytoplasmic membrane and cytoplasm immediately before the addition of targeting polynucleotide coated with recA protein.

The experiments were performed with the following results:

First, in order to test protocols to be used in nuclear encapsulation, freshly trypsinized growing human HEp-2 tumor cells were suspended in complete DMEM encapsulated in a mixture of agarose (2.5%, Fisher-Bioteck) and complete DMEM media adapting the protocols of Nilsson et al., 1983, so that the final agarose concentration was 0.5% (4 volumes cells in suspension with 1 volume 2.5% agarose), and the final cell concentration range was approximately $2.4 \times 10^7$ to $8 \times 10^5$. The encapsulated cells in agarose "beads" were placed in petri dishes to which DMEM complete media was added and were allowed to grow for 24 hr in an incubator at 37° C., 7% $CO_2$. At 24 hr, the cells were clearly growing and multiplying and thus were alive and metabolically active.

An aliquot of agarose containing cells (in beads in DMEM medium) was treated to remove the cytoplasmic membrane and cytoplasm by addition of ice-cold sterile PBS, New Buffer (Jackson et al. (1988) op.cit.; 130 mM KCl, 10 mM $Na_2HPO_4$, 1 mM $MgCl_2$, 1 mM $Na_2ATP$, and 1 mM dithithreitol, pH 7.4), New Buffer with 0.5% Triton-X 100, New Buffer with 0.2% BSA, then was centrifuged at low speed using protocols developed by Jackson and Cook, 1985 and 1986 op.cit.; Wittig et al. (1989) *J. Cell. Biol.* 108: 755; Wittig et al. (1991) op.cit.) who have shown that this treatment allows the nuclear membrane to remain morphologically intact. The nuclei are metabolically active as shown by a DNA synthesis rate of 85 to 90% compared with that of untreated control cells.

Cytoplasm was effectively removed by the above treatment, and the encapsulated nuclei were intact as demonstrated by their morphology and exclusion of 0.4% trypan blue. Nuclei in agarose were returned to the humidified $CO_2$ incubator at 37° C. for 24 hr and remained metabolically active. We observed that sterile mineral oil used in the emulsification process was difficult to remove entirely and interfered with the microscopic visualization of suspended nuclei. Therefore, the cell-agarose suspension process was simplified. In subsequent experiments cells were gently vortexed with melted (39° C.) agarose, then the agarose-cell mixture was sterilely minced before New Buffer treatments. This simpler process, eliminating the oil step, makes it easier to visualize the cells and chromosomes at the completion of reactions.

After mincing of the agar and New Buffer treatments of the cells, the above protocols were used to homologously target endogenous DNA sequences in encapsulated nuclei as follows: 16.5 μl recA-coated (or non-recA-coated control) nick-translated DNA (labeled with biotin-14-dATP) targeting polynucleotide was prepared and bound under standard native recA protocols (see U.S. Ser. Nos. 07/755,462 and 07/910,791). Minced agarose fragments were centrifuged and New Buffer supernatant removed. The fragments were resuspended in 1xAC buffer in a 1.5-ml Eppendorf tube, then centrifuged for removal of the buffer (leaving an estimated 50 to 75 μl of buffer), and prepared targeting polynucleotide was mixed with the fragments of agarose-containing nuclei. Reactions were incubated in a 37° C. water bath for 2 to 4 hr, then washed, incubated in standard preblock solution, then in preblock supplement with 10 μg/ml FITC-avidin (Vector, DCS grade), and again washed. Experimental results were analyzed by placing a minute amount of a reaction with 3 to 4 μl antifade on a slide with a slide cover and viewing it by using the Zeiss CLSM-10 confocal laser scanning microscope (CLSM). Completed reactions were also stored refrigerated for later examination.

In the first in vivo experiment, metabolically active HEp-2 cells suspended in 1xPBS were encapsulated in agarose by gentle vortexing, treated using New Buffer protocols, then incubated for 3 hr 15 min with 100 ng of recA-coated targeting polynucleotide specific for Chromosome 1 alpha-satellite DNA biotinylated with bio-14-dATP by nick translation (BRL, Nick Translation System) using pUC 1.77 plasmid DNA (a 1.77 kb long EcoRI fragment of human DNA in the vector pUC9; Cooke et al. (1979) *Nucleic Acids Res.* 6: 3177; Emmerich et al. (1989) *Exp. Cell. Res.* 181: 126). We observed specific targeting by the alpha-satellite targeting polynucleotide to pericentromeric chromosome 1 targets in intact nuclei of metabolically active cells. The signals were essentially identical to those using the same targeting polynucleotide with methanol (or ethanol) fixed HEp-2 cell targets in suspension. FIG. 1 shows specific targeting signals in several metabolically active cells from this experiment.

In the second in vivo experiment, cells suspended in incomplete DMEM media instead of 1xPBS were encapsulated in agarose and treated with 62.5 ng of the same targeting polynucleotide used in the first experiment described above and 62.5 ng of a freshly biotinylated targeting polynucleotide prepared under the same protocols. In this experiment, the minced agarose fragments were not resuspended in 1xAC buffer before addition of targeting polynucleotide and some nuclei disintegrated, especially with subsequent centrifugation. The results show that in the nuclei that remained intact, the targeting polynucleotides coated with recA specifically targeted predetermined human DNA targets. In contrast, targeting polynucleotides in control reactions without recA did not target the human DNA sequences.

Thus, the recA-coated targeting polynucleotides were targeted to the repetitive alpha satellite sequences of chromosome 1. This result showed DNA targeting in intact nuclei to specific human chromosome 1 sequences (data not shown).

In the third experiment, cells were suspended in 1xPBS or in incomplete DMEM media before vortexing with agarose and were tested using 62.5 ng of targeting polynucleotide in reactions with and without recA protein. In addition, the reactions were divided in half and washed and FITC-avidin treated in either buffer adjusted to pH 7 or pH 7.4. Cells were incubated with the recA coated targeting polynucleotide for 3 hr 25 min. Live nuclei treated with targeting polynucleotide alone without recA showed no signals. In the recA-treated reactions, relatively weaker signals were observed in nuclei incubated in 1xPBS, whereas very strong specific signals were present in nuclei that had been incubated in incomplete DMEM. There was clearly significantly more signal present in nuclei that were washed and treated with FITC-avidin at pH 7.4 compared with nuclei incubated at pH 7.0. FIG. 4 shows nuclei that were treated with recA coated targeting polynucleotides and incubated at both pH 7.4 and 7.0.

In a fourth experiment, HEp-2 cells were embedded in agarose prepared with 1xPBS, New Buffer treated, then treated with 100 ng of biotinylated targeting polynucleotide complementary to chromosome 1 alpha-satellite DNA. Controls in this experiment also included reactions without recA protein and additional control reactions supplemented with an identical amount of BSA protein to replace the recA protein. Additionally, cells were also embedded in agarose prepared with 1xAC buffer. Examples of specific targeting to endogenous target sequences were recorded.

In a fourth experiment, we directly determined if the embedded nuclei under the conditions used above were metabolically active. The nuclei in agarose were incubated with bio-21-rUTP in complete medium, then incubated for 2 days in the humidified $CO_2$ atmosphere. After 2 days at 37° C., the cells were examined. Bio-21-rUTP was incorporated in RNA and incubated with FITC-streptavidin. FITC was specifically associated with nucleoli indicative of ribosomal RNA biosynthesis, thus directly showing metabolic activity in these human cells. Similar results were obtained using DNA precursors to measure DNA synthesis. In this experiment it was clear that the majority of nuclei in the PBS agarose reaction had condensed chromosomes. There was nuclear division in a number of these nuclei also, indicative of full metabolic viability, which was also shown in the AC buffer-treated cells.

A fifth experiment was performed using, again, HEp-2 cells embedded in agarose. Final concentration of the cells in agarose was $3.7\times10^6$/ml. The cells were suspended in 1xPBS prior to combining with agarose. The final agarose concentration was 0.5%. There were two reactions, one in which recA was used to coat targeting polynucleotide, the second in which recA protein was replaced by BSA at the same protein concentration followed by New Buffer treatments to remove the cytoplasm. The nuclei in agarose were incubated for 3 hr with targeting polynucleotide, then processed for detection of correctly targeted polynucleotide using the protocols describe previously. FITC-avidin was used to visualize the biotinylated targeting polynucleotide at a concentration of 20 μg/ml. Results showed that cells with the recA-coated complementary targeting polynucleotide displayed specific signals in 25% or more of the intact nuclei. In contrast, the BSA-treated controls (without RecA) did not show any signal.

Cells in agarose from this experiment were further incubated at 37° C. in the $CO_2$ incubator in complete medium. At 22 hr, these cells were metabolically active. Chromosomes were condensed, and a number of nuclei were in the process of dividing. In these experiments, a significant number of the cells incubated with recA-coated complementary targeting polynucleotides showed specific signal, whereas 0% of the cells incubated with targeting polynucleotide alone showed specific signal.

In summary, recA-coated biotinylated targeting polynucleotides for human chromosome 1 alpha-satellite DNA were specifically targeted to human HEp-2 epithelial carcinoma chromosomal DNA in intact cell nuclei of metabolically active cells that had been suspended in agarose, then treated with buffers and recA-coated targeting polynucleotides under suitable reaction conditions (supra and U.S. Ser. No. 07/755,462, U.S. Pat. No. 5,273,881; U.S. Ser. No. 07/755,462, U.S. Pat. No. 5,273,881; and U.S. Ser. No. 07/520,321, U.S. Pat. No. 5,223,414 incorporated herein by reference). Specific binding by the recA-coated targeting polynucleocide to chromatin alpha-satellite DNA was observed only in the agarose embedded nuclei which were incubated with recA-coated targeting polynucleotides. Control nuclei incubated with targeting polynucleotides in the absence of recA and/or with nonspecific protein exhibited no signal.

Targeting of Human p53 Gene

We performed recA-mediated homologous targeting of biotinylated targeting polynucleotides that were homologous to the human p53 tumor suppressor gene, and compared the results to targeting of alpha satellite DNA sequences in human chromosome 1. In these experiments, exponentially growing cells were trypsinized, washed, suspended in incomplete medium and encapsulated in agarose. The agarose was minced into pieces with a razor blade and the encapsulated cells were treated with New Buffer. A sample from each group was removed to verify that nuclei were intact.

Nuclei were washed in 1×AC buffer and incubated with recA-coated complementary single-stranded DNA oligonucleotides (i.e., exogenous targeting polynucleotides) for 3.5 hours at 37° C. The alpha satellite DNA targeting polynucleotides for chromosome 1 were previously described and were nick-translated with biotinylated deoxyribonucleotides (bio-14-dATP). The p53 tumor suppressor gene polynucleotide was obtained from Oncor (209 Perry Parkway, Gaithersburg, Md. 20877) and is a 1.2 kilobase cDNA fragment from a wild-type human p53 gene (Fields and Jang, (1990) Science 242: 1046; Miller et al. (1986) Nature 319: 783; Zakut-Houre et al. (1985) EMBO J. 4: 1251). The 1.2 kilobase human p53 DNA was nick-translated with biotinylated deoxyribonucleotides and yielded a population of biotinylated targeting polynucleotides having a size range (about 100 to 600 nucleotides) similar to that obtained for the human chromosome 1 alpha satellite targeting polynucleotides. The targeting polynucleotides were separately incubated with encapsulated cells. Following incubation 3 washes of 1.75×SSC were done, and sampled nuclei were verified as intact after the washing step. After washing, the targeted encapsulated cell nuclei were incubated in preblock and FITC-avidin was added to preblock buffer to a final concentration of 20 μg/ml for 15 minutes in the dark. The targeted encapsulated cell nuclei were washed sequentially in 4×SSC, 4×SSC with 0.1% Triton X-100, and then 4×SSC. Samples of nuclei were again taken and used to verify that the targeted nuclei were metabolically active. Microscopic examination showed that metabolically active cells contained specific FITC-targeting polynucleotide: targeted endogenous sequence complexes (shown in FIG. 2). The p53 targeting polynucleotides were specifically targeted to human chromosome 17, the location of the endogenous human p53 gene sequences, indicating specific pairing of a targeting polynucleotide to a unique endogenous DNA target sequence. The human chromosome 1 alpha satellite DNA was also specifically targeted to the chromosome 1 pericentromeric satellite sequences.

The experiments validated a highly specific DNA targeting technique for human or other cells as evidenced by homologous sequence targeting techniques in metabolically active cells. The targeting technique employs the unique properties of recA-mediated DNA sequence targeting with single-stranded (complementary) short targeting polynucleotides. Native intact nuclei were incubated with labeled, heat-denatured targeting polynucleotides coated with recA protein. The DNA hybridized to the predetermined targeted homologous sequences. In these experiments, the targeting polynucleotides formed paired complexes with specific gene sequences within metabolically active cell nuclei. This in vivo targeting by recA-mediated homologous targeting polynucleotides shows the targeting specificity and therapeutic potential for this new in vivo methodology. Application of recA or other recombinase-mediated targeting of (complementary) ssDNA or denatured dsDNA targeting polynucleotides to predetermined endogenous DNA targets is important for gene entry, gene knockout, gene replacement, and gene mutation or correction.

EXAMPLE 2

Correcting a Mutant Gene to Produce a Functional Gene Product

Homologously targeted complementary DNA oligonucleotides were used to correct 11 bp insertion mutations in vector genes and restore vector gene expression and vector protein function in microinjected mammalian cells.

Experiments were designed to test whether homologously targeted complementary 276-bp oligonucleotide targeting polynucleotides could correct an 11-bp insertion mutation in the lacZ gene of a mammalian DNA vector, which encoded a nonfunctional β-galactosidase, so that a corrected lacZ gene encoded and expressed a functional enzyme. Functional enzyme (β-galactosidase) was detected by an X-gal assay that turns cells expressing a revertant (i.e., corrected) lacZ gene a blue color.

NIH3T3 cells microinjected with the mutant test vector bearing an 11 basepair insertion in the lacZ coding sequence do not produce any detectable functional β-galactosidase enzyme. In contrast, cells microinjected with the wild type test vector do produce functional enzyme.

We obtained the functional lac plasmid pMC1lacpA for use as a positive control for expression of β-galactosidase. pMC1lacXpA is the target test mutant plasmid (shown in FIG. 3). It is identical to pMC1lacpA (shown in FIG. 4) but has a 11-bp XbaI linker insertional mutation. This plasmid does not express β-galactosidase activity in mouse NIH3T3 cells when introduced by electroporation. It does not produce blue color in the presence of X-gal indicative of β-galactosidase production following vector microinjection. Negative controls with mock or noninjected cells we also done. Using these conditions and NIH3T3 cells have no detectable background blue staining.

The plasmid pMC1lacpA (8.4 kb) contains the strong polyoma virus promoter of transcription plus ATG placed in front of the lacZ gene. The polyadenylation signal from SV40 virus was placed in back of the lacZ gene. The plasmid vector was pIB130 from IBI (New Haven, Conn.). The mutant vector pMC1lacpA has a 11-bp insertion in the XbaI site consisting of the inserted sequence CTCTAGACGCG (SEQ ID NO:1) (see FIG. 5).

In several control micro-injection experiments using pMC1lacXpA we consistently failed to detect any blue microinjected cells. In contrast, in various experiments monitored early after microinjection approximately 9 to 13% of the NIH3T3 cells injected with pMC1lacpA DNA expressed β-galactosidase as evidenced by their blue color. No cells microinjected with injection buffer alone or mock injected were observed as blue.

We synthesized two 20-bp primers (PCRα and PCRβ) for producing a 276-bp PCR product (see FIG. 5) from the wild-type lacZ sequence for use as targeting polynucleotides. We chose this 276-bp fragment to span the 11 bp insertion mutation as a nonhomologous sequence. The 276-bp DNA oligonucleotide was separated by gel electrophoresis and electroeluted from agarose, ethanol precipitated, and its concentration determined by absorbance at 260 nm. The 276-bp fragment was 5' end-labeled with $^{32}P$ and specifically D-looped with the pMc1lacXpA or pMC1lacpA plasmid DNA using recA as shown by agarose gel electrophoresis.

Experiments were designed to test for β-galactoside production in cells microinjected with pMC1lacXpA vectors with targeting polynucleotide-target complexes using complementary 276-bp oligonucleotide targeting polynucleotide treated with recA. The 276-mer targeting polynucleotides in 1×TE buffer: were denatured by heating at 100° C. for 5 min and immediately quenched in an ice bath for 1 min. The DNA solution was collected at 4° C. by centrifugation. RecA-mediated targeting polynucleotide reactions containing a final volume of 10 μl were assembled using 1.0 μl 10×AC buffer, 1.5 μl 16 mM ATPγS, 3.8 μl dd $H_2O$, 1.2 μl recA protein solution (13 μg/μl), and 2.5 μl of a 30 μg/ml stock of heat-denatured 276-bp targeting polynucleotide. The recA protein was allowed to coat the DNA for 10 min at 37° C. Next, 1.0 μl of 10×AC buffer, 1.0 μl of 0.2 M magnesium acetate, 1.3 μl of pMC1lacXpA (1.0 μg/μl), and 6.7 μl of dd $H_2O$ was added to a final volume of 20 μl. Control reactions were performed without added recA protein.

NIH3T3 cells were capillary needle microinjected with targeting polynucleotide-target DNA mixtures loaded in glass pipettes freshly pulled into microneedles using a Sutter instruments microprocessor controlled apparatus. An ECET Eppendorf microinjection pump and computerized micromanipulator were used for computer-assisted microinjection using an Olympus IMT-2 inverted microscope. Cells were carefully microinjected under controlled pressure and time. NIH3T3 cells injected with pMC1lacpA showed approximately 9% of the injected cells were blue. None (0%) of the cells injected with pMC1lacXpA DNA in reactions containing the 271 bp oligonucleotide but without recA protein showed a blue color. In marked contrast, approximately 3.6% of the cells microinjected with the recA-coated 271-bp targeting polynucleotide targeted to-the pMC1lacXpA target hybrid were blue (FIG. 6), indicating that the mutant pMC1lacXpA gene can be targeted and corrected by the 271-bp oligonucleotide, which has been targeted with recA-coated targeting polynucleotides. In summary, these measurements show that the 11 bp Xba I insertion mutation can be corrected with the recA-mediated targeted corrected in vivo, but not with the 271-bp oligonucleotide alone. Note that the in situ identification of 3T3 cells expressing β-galactosidase was performed following incubation with X-gal (5-bromo-4-chloro-3-indolyl-β-galactopyranoside) (Sigma), as described by Fischer et al. (1988) *Nature* 332: 853; Price et al. (1987) *Proc. Natl. Acad. Sci.* (*U.S.A.*) 84: 156; Lim and Chae (1989) *BioTechniques* 7: 576.

EXAMPLE 3

Correcting a Human CFTR Disease Allele

Homologously targeted complementary DNA oligonucleotides were used to correct a naturally occurring 3 bp deletion mutation in a human CFTR allele and restore expression of a functional CFTR protein in targeted mammalian cells.

A major goal of cystic fibrosis (CF) gene therapy is the correction of mutant portions of the CF transmembrane conductance regulator (CFTR) gene by replacement with wild-type DNA sequences to restore the normal CFTR protein and ion transport function. Targeting polynucleotides that were coated with recA protein were introduced into transformed CF airway epithelial cells, homozygous for both alleles ΔF508 CFTR gene mutation, by either intranuclear microinjection, electroporation, or by transfection with a protein-DNA-lipid complex.

Isolation and characterization of the CFTR gene (Rommens et al. (1989) *Science* 245: 1059; Riordan et al. (1989) *Science* 245: 1066, incorporated herein by reference) has been crucial for understanding the biochemical mechanism(s) underlying CF pathology. The most common mutation associated with CF, a 3-base-pair, in-frame deletion eliminating a phenylalanine at amino acid position 508 (ΔF508) of CFTR, has been found in about 70% of all CF chromosomes (Kerem et al. (1989) *Science* 245: 1073; Kerem et al. (1990) *Proc. Natl. Acad. Sci.* (*U.S.A.*) 87:

8447). Correction of ΔF508 and other CFTR DNA mutations lies at the basis of DNA gene therapy for CF disease. Elimination of the cAMP-dependent Cl ion transport defect associated with CFTR gene mutations has been accomplished through the introduction of the transcribed portion of wild-type CFTR cDNA into CF epithelial cells (Rich et al. (1990) *Nature* 347: 358; Drumm et al. (1990) *Cell* 62: 1227).

An immortalized CF tracheobronchial epithelial human cell line, ΣCFTE29o-, is homozygous for the ΔF508 mutation (Kunzelmann et al. (1992) *Am. J. Respir. Cell. Mol. Biol.*, in press). These cells are useful as targets for homologous recombination analysis, because they contain the same 3 basepair deletion in CFTR allele on all copies of chromosome 7. Replacement of the ΔF508 allele with wild-type CFTR DNA in indicated only when homologous recombination has occurred. The 491 bp region of the CFTR gene spanning exon 11 and containing 3' and 5' flanking intron sequences was selected from sequence data published previously (Zielenski et al. (1991) *Genomics* 10: 214, incorporated herein by reference) and used as a targeting polynucleotide. The DNA fragment was PCR amplified in preparative quantities and then denatured for introduction into cells as recA-coated complementary ssDNA (or dsDNA). Exponentially growing cells were transfected by intranuclear microinjection and were propagated on the same petri dishes in which they were microinjected. Cells outside the microinjected area were removed by scraping with a rubber policeman. Exponentially growing cells were typsinized and washed before electroporation. Cells transfected with protein-DNA-lipid complexes were grown to approximately 70–80% confluence before transfection.

The 491 bp fragment was generated by PCR amplification from the T6/20 plasmid (Rommens et al. (1989) op.cit., incorporated herein by reference) and verified by restriction enzyme mapping and propagated as described previously. After digestion with EcoRI and HindIII, a 860 bp insert was isolated following electrophoresis in 0.8% SeaPlaque agarose gel. The 860 bp fragment contained CFTR exon 10, as well as 5' and 3' intron sequences, as defined by the restriction enzyme cleavage sites (Zielenski et al. (1991) op.cit.). A 50 ng aliquot of the fragment was amplified by PCR using primers CF1 and CF5 (Table 1) to generate a 491 bp fragment. The conditions for amplification were denaturation, 94° C. for 1 annealing, 53° C. for 30 sec; extension, 72° C. for 30 sec with a 4 sec/cycle increase in the extension time for 40 cycles. The fragment size was confirmed by electrophoresis on a 1% agarose gel, then amplified in bulk in 20 separate PCR amplifications, each containing 50 ng of target DNA. The 491 bp PCR products were extracted with phenol:chloroform:isoamyl alcohol (25:24:1) extraction and precipitated with ethanol. DNA precipitates were collected by centrifugation in an Eppendorf microcentrifuge and resuspended at a final concentration of 1 mg/ml. The 491 bp fragment contained exon 10 (193 bp), as well as 5' (163 bp) and 3' (135 bp) flanking intron sequences, as defined by primers CF1 and CF5.

The 491 nucleotide fragments were coated with recA protein using the reaction buffer of Cheng (Cheng, et al. (1988) *J. Biol. Chem.* 263:15110, incorporated herein by reference). Typically, the 491 bp DNA fragment (5 μg) was denatured at 95° C. for 10 min, then added to a 63 μl of coating buffer containing 200 μg of recA protein, 4.8 mM ATPγS, and 1.7 μl reaction buffer (100 mM Tris-Ac, pH 7.5 at 37° C.; 10 mM dithiothreitol; 500 mM NaOAc, 20 mM MgOAc, 50 percent glycerol) and incubated for 10 min at 37° C. Next, the MgOAc concentration was increased to a final concentration of about 22 mM by addition of 7 μl of 200 mM MgOAc. Under these conditions, the 491 nucleotide fragment was coated with recA protein at a molar ratio of 3 bases per 1 recA molecule. After coating the fragments were immediately placed on ice at 4° C. until transfection (10 min to 1 hr).

Microinjection, when used, was performed with an Eppendorf 5242 microinjection pump fitted to an Eppendorf 5170 micromanipulator using borosilicate pipettes (Brunswick, 1.2 OD×1.9 ID) fabricated into a microneedle with a Sutter Instruments (P-87) micropipette puller. The micropipettes were filled by capillary force from the opposite side of the needle. Approximately 100 pipettes were used for injecting of 4000 cells. Cells were injected with approximately 1,000–10,000 fragments per cell by intranuclear injection with 120 hPa for 0.1–0.3 s at a volume of 1–10 fl/nucleus. Microinjected cells were viewed with an Olympus IMT-2 inverted microscope during the injection. The area of the petri dish containing injected cells was marked with 2 to 5 mm diameter rings. Needle microinjection was performed in cells grown on 10 separate 60 mm petri dishes. Cells were injected at room temperature in culture medium after two washes in phosphate buffered saline (PBS). After microinjection, noninjected cells in the culture were removed by scraping. Injected cells were grown at 37° C. in a humidified incubator at 7 days and then harvested for DNA and RNA.

Electroporation experiments were performed using recA-coated 491-mer ssDNA as described above. Approximately 1×10$^8$ exponentially growing cells were suspended in 400 μl of coating buffer with 5 μg of recA coated-DNA. The cell suspension was pre-incubated on ice for 10 min and electroporated at room temperature with 400 V and 400 μF in a BTX 300 electroporator (BTX Corporation, San Diego, Calif.). After electroporation, cells were incubated on ice for an additional 10 min, diluted in Eagle's minimal essential medium (MEM) supplemented with 10% fetal bovine serum (FBS) and 100 μg/ml streptomycin, 100 U/ml penicillin (Cozens et al. (1992) *Proc. Natl. Acad. Sci. (U.S.A.)* 89: 5171; Gruenert et al. (1988) *Proc. Natl. Acad. Sci. (U.S.A.)* 85: 5951; Kunzelmann, (1992) op.cit.), and then seeded in T75 flasks. Under these conditions of elecroporation, approximately 30–50% of the cells survive. Cells were cultured for 507 days at 37° C. and then harvested for DNA and RNA.

Protein DNA-lipid complexes (liposomes) were prepared. Briefly, dioleoylphosphatidyl-ethanolamine (PtdEtn, DOPE) was used for preparing liposomes by drying 4 μM solutions of the lipid under nitrogen at room temperature. The lipid film was rehydrated with 4 ml of 30 mM Tris-HCl buffer (pH 9), then sonicated for 15 minutes under an atmosphere or argon. The protein-DNA complex was prepared in polystyrene tubes by diluting 20 μg of recA-coated 491-base DNA in 30 mM Tris-HCl, (pH 9) buffer. Protein (GmS) was also diluted with 30 mM Tris HCl (pH 9) to a final concentration of 2 mg/ml from a 20 mg/ml stock solution prepared in dimethyl sulfoxide. The protein (40 μg) was added to the DNA and rapidly mixed. Next, 175 μl of the liposome solution (175 nmoles of lipid) were added to the peptide DNA mixture.

Genomic DNA was isolated and purified from cells as described in Maniatis op.cit. to test for homologous DNA recombination. Cellular DNA was first PCR-amplified with primers CF1 and CF6 (Table 1). CF1 is within the region of homology defined at the 5' end of the 491 bp CFTR fragment CF6 is outside the region of homology at the 3' end of this fragment.

The conditions for the PCR amplification were as follows: CF1/CF6; 684/687 bp fragment; primers, 0.5 μM; DNA, 1–2

μg; denaturation; 94° C. for 1 min; annealing; 53° C. for 45 s; extension; 72° C. for 90 s with a 4-s/cycle increase in extension time for 40 cycles; $Mg^{+2}$ 1.5 mM. DNA fragments were separated by agarose electrophoresis and visualized by staining with ethidium bromide, then transferred to Gene Screen Plus filters (DuPont). The DNA was then hybridized with the allele-specific normal CFTR $^{32}$P-end-labeled DNA probe defined by oligo N as described by Cozens et al. (1992) op.cit.; Kunzelmann (1992) op.cit., incorporated herein by reference. The presence of wild-type (WT) sequences was determined autoradiographically by hybridization with the radiolabeled DNA probe.

Homologous recombination was verified in a second round of PCR DNA amplification using the 687/684 bp fragment as a DNA template for amplification. The primers used in this allele-specific reaction were CFI and the oligo N or oligo ΔF. The size of the DNA fragments was 300 bp (oligo N) or 299 bp (oligo ΔF).

The conditions for the reaction were as follows: CF1/oligo N/ΔF; 300/299 bp fragment; primers, 0.5 μM; DNA, 1–2 μg; denaturation, 95° C. for 45s; annealing, 51° C. for 30s; extension, 72° C. for 30s with a 3-s/cycle increase in extension time for 40 cycles; $Mg^{+2}$, 1.5 mM. In DNA from transfected ΣCFTE29o- cells, amplified with the CF1/oligo N primers, a PCR product was detected only if the wild-type CFTR sequences were present. Amplification with the CFl/oligo ΔF gives a PCR DNA product of DNA targets purified from transfected and nontransfected ΣCFTE29o- cells but not for DNA targets isolated from control normal cells (16HBE14o-). The presence of wild-type CFTR sequences in the amplified DNA fragments was also determined autoradiographically after hybridization with $^{32}$P-5'-end-labeled oligo N as probe.

Cytoplasmic RNA was isolated and denatured at 95° C. for 2 min, then reverse-transcribed using the DNA polymerase provided in a PCR RNA Gene Amp kit according to manufacturer's instructions (Perkin-Elmer/Cetus). First strand cDNA was amplified by using primer CF17 at the 5' end of exon 9 and the allele-specific oligo N or oligo ΔF primers. The length of the PCR fragments is 322 bp (CF17/oligo N) and 321 bp (CF17/oligo ΔF).

The conditions for PCR amplification are CF17/oligo N/ΔF, 322/321 bp fragment; primers, 1 μM; denaturation, 94° C. for 1 min; annealing, 51° C. for 30s; extension, 72° C. for 20s with a 4-s/cycle increase in extension time for 40 cycles; $Mg^{+2}$, 0.8 mM. DNA fragments were visualized after electrophoresis on ethidium bromide-stained 1% agarose gels. In addition to the allele-specific PCR amplification of first-strand cDNA, Southern hybridization was performed as described above. Fragments were transferred to Gene Screen Plus filters then hybridized with allele-specific oligo N probe under the same conditions used for the Southern analysis of the genomic DNA (Kunzelmann et al. (1992) op.cit.; Cozens et al. (1992) op.cit.). The presence of wild-type CFTR RNA was confirmed by hybridization and autoradiography of RNA extracted from normal (16HBE14o-) control DNA and in DNA of transfected ΣCFTE29o- cells.

Hybridization was performed as described previously (Cozens et al. (1992) op.cit.). DNA fragments were separated by agarose gel electrophoresis. DNA was denatured with 0.4 N NaOH and 0.6 M NaCl for 30 min, then washed once with 1.5 M NaCl and 0.5 M Tris-HCl for 30 min. DNA was transferred to Gene Screen Plus membrane (NEN-DuPont) by capillary blot, again denatured with 0.4 N NaOH for 1 min, and then neutralized with 0.2 M Tris-HCl (pH 7.0). DNA on membranes was prehybridized for 1 h at 37° C. in 6×SSC, 5×Denhardt's solution, 1% SDS, containing 100 μg/ml of denatured salmon sperm DNA (Sigma). Oligonucleotide probes (oligo N or oligo ΔF; 10 ng) were $^{32}$P-5'-end-labeled with 20 units of T4 kinase and 40 μCi $^{32}$P-γ-ATP for 30 min at 37° C. Unincorporated nucleotides were removed by centrifugation of the reaction mix through a minispin column (Worthington Biochemical Corp., Freehold, N.J.). Hybridization was performed overnight at 37° C. Membranes were washed twice for 5 min each time in 2×SSC at room temperature, twice for 30 min in 2×SSC, 0.1% SDS at 45° C., and once in 0.1×SSC for 30 min at room temperature. After washing, hybrids on membranes were analyzed autoradiographically by exposure to x-ray film.

Analysis of ΣCFTE29o- DNA shows replacement of the endogenous mutant (ΔF508) sequences with the exogenous normal fragment as evidenced by PCR amplification of genomic DNA and allele-specific Southern blot hybridization. PCR primers, one inside (CF1), and one outside (CF6) the region of homology (491 bp), were used to test whether the amplified DNA band was possibly due to amplification of any residual DNA fragment remaining in the cell after the transfection or by possible random DNA integration. A 687 bp fragment contains normal CFTR sequences while the 684 bp fragment is generated from ΔF508 CFTR DNA. To determine whether endogenous ΔF508 sequences were replaced with exogenous normal CFTR sequences, we analyzed aliquots of the 687 or 684 bp amplification fragments by Southern hybridization using $^{32}$P-end-labeled DNA probes specific for the ΔF508 or wild-type sequences (Table 1). In addition, the 687 bp fragment was PCR amplified by using the CF6 primer and a primer specific for either ΔF508 (oligo ΔF) or normal sequences (oligo N). The second round of DNA amplification with the CF1/oligo N or ΔF primer pair combination yields 300/299 bp fragments, respectively. With the CF1/oligo N primer pair combination, a fragment will be detected only if the mutant DNA has been replaced by normal sequences. Further confirmation of homologous DNA recombination was tested by allele-specific Southern blot hybridization of the 300/299 bp fragments.

Analysis of cytoplasmic RNA to detect normal exon 10 sequences in CFTR mRNA, verify that the homologous DNA recombination was legitimate and that normal CFTR mRNA is expressed in the cytoplasm. To test whether the PCR generated DNA fragments were exclusively CFTR mRNA-derived, primers in exon 9 (CF17) and allele-specific (normal, oligo N or ΔF508, oligo ΔF) primers in exon 10. This amplification with primers CF17/N yields a 322 bp normal fragment only if transcription of homologously recombined DNA has occurred. A 321 bp DNA fragment would be generated if the ΔF508 mutation were present. Furthermore, Southern hybridization analysis with allele-specific $^{32}$P-end-labeled probes differentiated between normal and ΔF508 mutant sequences and were also used to confirm expression of wild-type CFTR mRNA in the cytoplasm.

Figure 7B:
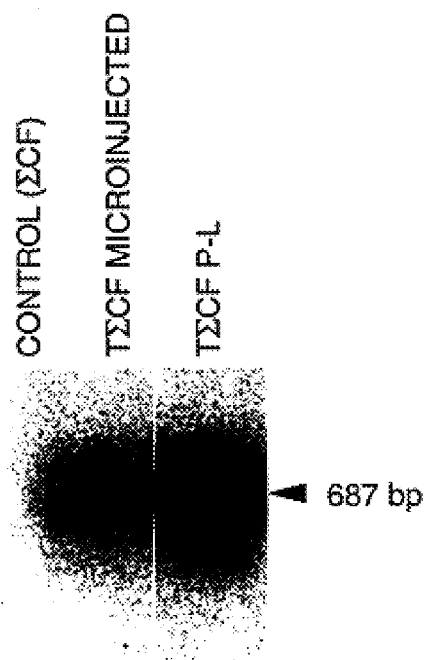
FIG. 7B. Autoradiographic analysis of DNA transferred to Gene Screen Plus filters and hybridized with a $^{32}$P-labeled oligonucleotide specific for normal exon 10 sequences in the region of the ΔF508 mutation. Cells transfected by microinjection or protein-lipid-DNA complexes both were positive for homologous targeting, whereas control cells were not.
Figure 9:
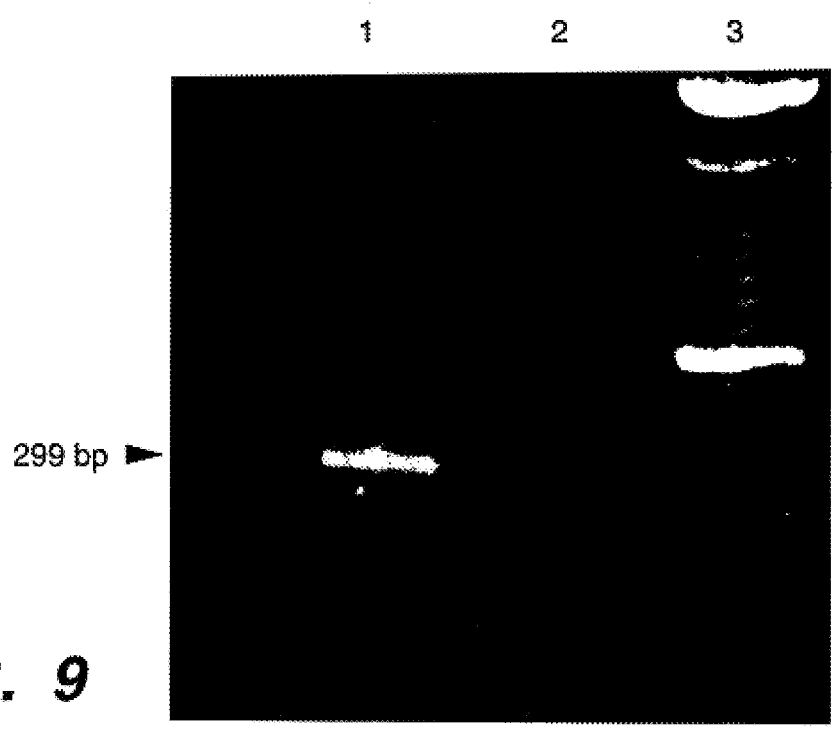
FIG. 9. PCR analysis of ΣCFTE29o-genomic DNA reconstructed with the addition of $2 \times 10^5$ copies of recA-coated 491-nucleotide DNA fragments per microgram of genomic DNA. This number of DNA fragments represents the total number of DNA copies microinjected into cells and tests whether the 491-nucleotide fragment can act as a primer for the 687/684-bp fragment amplification. DNA was amplified as described in FIG. 8A. When the second round of amplification was conducted with CF1 and oligo N primers (lane 2), the 300-bp DNA band was not detected when aliquots of the amplification reaction were separated electrophoretically. Amplification of the ΣCFTE29o/491 bp DNA fragment with the CF1/oligo ΔF primer pair produced a 299-bp DNA product (lane 1). Marker DNA is in lane 3.

Homologous recombination between the targeting polynucleotide comprising WT CFTR DNA and ΔF508 mutant cellular DNA allelic targets was evaluated by analysis or cellular DNA and RNA isolated from transfected and non-transfected ΣCFTE29o- cell cultures. Nuclear genomic DNA and cytoplasmic RNA were isolated 6 days after transfection, CFTR exon I sequences were amplified by PCR. Oligonucleotide primers (Table 1) were used to amplify the region of CFTR DNA spanning exon 10. One PCR primer (CFI) was within the region of homology defined by the 491 bp DNA fragment (sense primer), and the other (CF 6) was outside the homologous region in the 3' intron (antisense primer). This DNA amplification reaction produces a 687 bp fragment with normal human CFTR DNA or a 684 bp fragment if the DNA contains the ΔF508 mutation, as shown in FIG. 7A. Southern hybridization was carried out on the 687/684 bp DNA fragments generated from amplification of genomic DNA from cell cultures by microinjection or by transfection with the protein-DNA-lipid complex, shown in FIG. 7B. A probe consisting of $^{32}$P-end-labeled oligonucleotide DNA that hybridized only to DNA sequences generated from a normal exon 10 was used. DNA from all microinjected and transfected cells produced specific hybrids as evidenced by autoradiographic hybridization. For cells microinjected with the 491 nucleotide fragment (FIG. 7B, lane 2), the present of normal exon 10 sequences indicated homologous replacement at least a frequency of $\geq 2.5 \times 10^{-4}$. This result indicates at least one correctly targeted homologous DNA replacement in about 4000 microinjected nuclei. Other similar experiments using either electroporation or protein-DNA-lipid transfection to transfer the recA-coated 491 nucleotide CFTR DNA fragments also showed homologous recombination with the normal CFTR sequence in transfected CF cells. No hybridization was observed in control nontransfected (or mock-injected ΣCFTE29o- cells). In each cell transfected with normal CFTR DNA, analysis of the genomic DNA in a second round of allele-specific amplification of the 681/684 bp fragments with primers CFI/oligo N (Table 1) clearly showed the 300 bp fragment expected when wild-type CFTR sequences are present, as shown in FIG. 8A. Fragments were detected for control 16HBE14o- cells (FIG. 8A, lane 2) and cells transfected with recA-coated DNA (FIG. 8A, lanes 5 and 6). A 299 bp fragment (ΔF508-specific primer ends one base closer to the CF1 than the oligo N) was detected in DNA from nontransfected ΣCFTE29o- cells amplified with CF1/oligo ΔF primers (FIG. 8A, lane 4). No fragment was detected in DNA from nontransfected ΣCFTE29o- cells reamplified with the CF1/oligo N primers (FIG. 8A, lane 3). Allele-specific Southern blot hybridization of these fragments with the $^{32}$P-end-labeled oligo N probe resulted in autoradiographic hybridization signals from control normal and transfected CF cells (FIG. 8B, lanes 1, 4, and 5) but not from DNA of nontransfected CF cells amplified with CF1 and oligo-N or -ΔF (FIG. 8B lanes 2 and 3). We tested whether any residual 491 nucleotide DNA fragments, which might remain in the cell after 6 days could act as a primer for the PCR reaction, genomic ΣCFTE29o- DNA was incubated with an equivalent number of recA-coated DNA fragments ($10^3$–$10^4$) introduced by microinjection (FIG. 9). One antisense primer contains the wild-type normal (N) sequence while the other contains the ΔF508 (ΔF) mutation. Amplification with the CFI/ΔF primer combination gives a 299 bp fragments when the ΔF508 mutation is present. No DNA fragment product was detected when the CF1/N primer combination wee used with control nontransfected ΣCFTE29o- DNA (FIG. 9, lane 2). However, when the CF1/ΔF primer combination was used for DNA amplification in nontransfected ΣCFTE29o- cells, a DNA product of the expected size (299 bp) was produced (FIG. 9, lane 1). These results indicate that all residual 491 nucleotide DNA fragments which might remain in the cells after 6 days of culture were incapable of competing with the CF1 PCR primers in the PCR amplification of the 687/684 bp fragments.

TABLE 1

PCR Primers and Oligonucleotides

| Oligonucleotide | DNA Strand | DNA Sequence |
| --- | --- | --- |
| CF1 (SEQ ID NO:2) | S | 5'-GCAGAGTACCTGAAACAGGA |
| CF5 (SEQ ID NO:3) | A | 5'-CATTCACAGTAGCTTACCCA |
| CF6 (SEQ ID NO:4) | A | 5'-CCACATATCACTATATGCATGC |
| CF17 (SEQ ID NO:5) | S | 5'-GAGGGATTTGGGGAATTATTTG |
| OLIGO N (SEQ ID NO:6) | A | 5'-CACCAAAGATGATATTTTC |
| OLIGO ΔF (SEQ ID NO:7) | A | 5'-AACACCAAGATATTTTCTT |

Notes:
(1) CF1 and CF5 PCR primers were used to synthesize the 491 bp fragment used for the--targeting polynucleotide.
(2) CFI and CF6 PCR primers were used to amplify the 687/684 bp CFTR fragment.
(3) The CF 17 primer is located at the 5' end of exon 9 and was used for amplification of first strand cDNA derived from CFTR mRNA.
(4) Oligo N and Oligo ΔF are allele-specific probes and can also be used as allele-specific PCR primers for amplifying the 300/299 bp fragments (DNA analysis) and the 322/321 bp fragments (RNA analysis).
(5) Sense (S) and antisense (A) primers are designated under DNA Strand and indicate the sense of the strand relative to the transcribed direction (i.e., the CFTR mRNA).

The corrected CFTR DNA must also be expressed at the mRNA level for normal function to be restored. Therefore, cytoplasmic CFTR mRNA was analyzed for the presence of a normal CFTR RNA sequence in the ΔF508 region of exon 10. Cytoplasmic RNA was isolated from the cells, reverse-transcribed with DNA polymerase and PCR-amplified as first-strand cDNA. This amplification was performed with a PCR primer located in exon 9 (CF17, sense) and CFTR allele-specific PCR primer in exon 10 (oligo N or ΔF, antisense). The exon 10 primer contains the CF mutation site, and the resulting fragment is 322 bp in normal DNA or 321 bp in DNA containing the ΔF508 mutation. Amplification of genomic DNA is eliminated by using primers that require amplification across intron/exon boundaries. Amplified cDNA generated from normal control 16HBE140- cells and experimentally transfected cells yielded DNA product fragments with the CF17/oligo N, whereas nontransfected ΣCFTE29o- cells only showed a DNA fragment after amplification with the CF17/oligo ΔF primers but not with the CF17/oligo N primers. Cells electroporated with wild-type 491-mer CFTR DNA showed the presence of wild-type CFTR mRNA. In addition, protein-DNA-lipid-transfected ΣCFTE29o- cell cultures also showed the presence of wild-type CFTR mRNA in cells transfected with the recA-coated 491 nucleotide fragment. Southern hybridization of the 322/321 bp cDNA fragments with the $^{32}$P-end-labeled N oligonucleotide DNA probe showed the specificity of the PCR amplification and produced specific autoradiographic hybridization signals from all cell cultures transfected with recA-coated 491 nucleotide targeting polynucleotide. No autoradiographic hybridization signals were detected in nontransfected ΣCFTE29o- cells amplified with the CF17/oligo N or oligo ΔF primers. These analyses verify that the genomic DNA homologously recombined with the WT 491-mer DNA at the ΔF508 CFTR DNA locus resulting in RNA expressed and transported to the cytoplasm as wild-type CFTR mRNA.

This evidence demonstrates that human CFΔF508 epithelial cells CFTR DNA can homologously recombine with targeting polynucleotides comprising small fragments of WT CFTR DNA resulting in a corrected genomic CFTR allele, and that a recA-coated targeting polynucleotide can be used in transfection reactions in cultured human cells, and that cystic fibrosis ΔF508 mutations can be corrected in genome DNA resulting in the production of normal CFTR cytoplasmic mRNA.

Taken together, the data provided indicates that 491-mer ssDNA fragments can find their genomic homologues when coated with recA protein and efficiently produce homologously targeted intact cells having a corrected gene sequence. Analysis of CFTR in cytoplasmic RNA and genomic DNA by allele-specific polymerase chain reaction (PCR) amplification and Southern hybridization indicated wild-type CFTR DNA sequences were introduced at the appropriate nuclear genomic DNA locus and was expressed as CFTR mRNA in transfected cell cultures. Thus, in human CF airway epithelial cells, 491 nucleotide cytoplasmic DNA fragments can target and replace the homologous region of CFTR DNA containing a 3 bp ΔF508 deletion.

Correctly targeted homologous recombination was detected in one out of one microinjection experiment with recA-coated targeting polynucleotide, two of two different electroporation experiments with recA-coated targeting polynucleotide, and one of one lipid-DNA-protein complex transfection experiment with recA-coated targeting polynucleotide. Taken together, these 4 separate experiments strongly indicate that homologous recombination with recA-coated targeting polynucleotides (491-mer CFTR DNA) is feasible for treatment of human genetic diseases, and can be performed successfully by using various methods for delivering the targeting polynucleotide-recombinase complex.

EXAMPLE 4

Homologous Recombination in Procaryotic Cells

In order to study the biological consequences of the cssDNA probe:target hybrid DNA structures in cells, we developed a simple and elegant assay to rapidly screen for in vivo homologous recombination events in *Escherichia coli*. The principle of this assay is to screen for the recombinogenocity of hybrid structures formed between a dsDNA plasmid target carrying a 59 bp deletion in the lacZ gene (pRD.59) and cssDNA probes from the wild type lacZ (IP290) gene by introducing these pre-formed protein-free hybrids into *E coli* by electroporation (FIG. 10). Homologous recombination frequencies are scored by plating transformed cultures in the presence of a chromogenic substrate (X-gal) so that recombinant bacterial cells (carrying plasmids that encode a wild type lacZ gene resulting from homologous recombination) appear blue.

DNA plasmids and DNA probes: The plasmid pRD.59 was made from the 2.9 kb cloning vector pBluescript IISK(-) (pRD.0) (Stratagene). The pRD.0 DNA was linearized at a unique EcoRI site in the polylinker region of the lacZ gene and digested with mung bean nuclease (Boehringer-Mannheim). The plasmids were then ligated and transformed into the RecA(-) *E coli* host XL1-Blue (Stratagene). The resulting alpha peptide mutant clones were screened for lack of alpha-complementation of β-galactosidase activity, which results in white colonies when grown on plates containing X-gal and IPTG (Sambrook et al., 1989). Plasmid DNAs recovered from white colonies by a mini-prep procedure (Qiagen) lacked the unique EcoRI site, as well as the XhoI and XbaI sites. These mutant clones were then sequenced using Sanger dideoxy sequencing methods (Sequenase Kit version 2, USB) to determine the length of the deletion. Several clones containing deletions ranging from 4 bp to 967 bp were sequenced and named pRD for plasmids with an EcoRI deletion. The cloning vector pBluescript IISK(-) was named pRD.0 because it does not contain any deletions.

All samples of the plasmid DNA were then prepared by the Qiagen Maxi-Prep (Qiagen) procedure from strain of XL1-Blue (Stratagene) containing the plasmids. The cultures were grown on Luria-Broth (LB) media (Sambrook, et al., 1989) containing 100 μg/ml ampicillin. Recovered plasmids were more than 90% negatively supercoiled Form I DNA as judged by agarose gel electrophoresis.

Biotinylated cssDNA probes were made from a fragment of the normal pBluescript IISK(-) plasmid. The plasmid DNA was linearized with BglI and run on a 1% agarose gel in 1X TAE. After ethidium bromide staining, the 1.6 kB fragment band was excised from the gel and purified using the Qiaex II gel purification method (Qiagen). This 1.6 kb fragment was diluted 1:20 and then used as a template for PCR. The PCR reaction mixture contained biotin-14-dATP (GIBCO-BRL) in order to synthesize IP290, a 290 bp biotinylated cssDNA probe homologous to the LacZ region of pRD.0. In addition, pRD.59 was linearized with BglI and the 1.55 kb fragment was purified in the same manner as the pRD.0 1.6 kb fragment. Using the same primers that were used to synthesize IP290, the pRD.59 1.55 kb fragment was used as a template for PCR to synthesize DP231, a 231 bp biotinylated cssDNA probe homologous to the LacZ region of pRD.59. It is missing the 59 base pair sequence that flanks the EcoRI site. Biotinylated cssDNA probe CP443 was made in the same manner except that pRD.0 was linearized with DraI and different primers were used. CP443 is completely homologous to pRD.0 and pRD.59 in a region outside of the LacZ gene.

RecA mediated cssDNA targeting reactions and purification of probe:target DNA hybrids: Before targeting, biotinylated cssDNA probes (70 ng) were denatured by heat at 98° C. for 10 minutes, cooled immediately in an ice-water bath, and then centrifuged at 4° C. for 10 seconds to recover all liquids. Reactions without cssDNA probe contained equivalent volumes of water. The denatured cssDNA probes were then coated with RecA protein (Boehringer-Mannheim) in Tris-acetate reaction buffer (Cheng et al., 1988; 10 mM Tris-acetate (pH 7.5), 1 mM dithiothreitol, 50 mM sodium acetate, 2 mM magnesium acetate, 5% (v/v) glycerol) with 2.43 mM ATPgS for 15 minutes at 37° C. in a 10 μl volume. Reactions without the RecA protein contained equivalent volumes of RecA storage buffer (20 mM Tris-HCl, pH 7.5, 0.1 mM EDTA, 1 mM DTT, and 20% glycerol).

The RecA mediated targeting reactions were performed by adding 1–4 μg of the appropriate plasmid DNA in an aqueous solution containing 22 mM magnesium acetate, bringing the final magnesium concentration to 11 mM and the final reaction volume to 20 μl. The reaction was incubated for another 60 minutes at 37° C.

At the end of the targeting reaction, SDS was added to a final concentration of 1.2% to deproteinize the complexes. If further enzymatic treatments were necessary on the targeted complexes, 3 volumes of phenol:choloform:isoamyl alcohol (Sigma), shaken on a Multi-Tube Vortexer (VWR) for 4 minutes at 4° C., and centrifuged for 5 minutes at 4° C. The supernatant was recovered, placed in a new tube, and extracted with 1 volume of chloroform. The mixture was shaken for 2 minutes at 4° C., and centrifuged for 5 minutes at 4° C. The supernatant was recovered, containing the purified targeted complexes.

Detection of probe:target DNA hybrids: After deproteinization, the complexes were run for 20 hours at 30 V on a 20 cm by 25 cm 1% agarose TAE gel (GIBCO-BRL) at room temperature. The gels were visualized by staining in 1 µg/ml ethidium bromide and then cut down to 11 cm by 14 cm before they were soaked in 10× SSC and transferred to positively charged Tropilon membranes (Tropix) by Southern blotting method under non-denaturing conditions. Blots were then UV cross-linked (Stratalinker).

Biotinylated cssDNA probes and probe:target hybrids were detected using the Southern-Light System (Tropix). The nylon bound DNA blots were treated with avidin conjugated to alkaline phosphatase, followed by the chemiluminescent substrate, CDP-Star (Tropix), in conditions described by the manufacturer. Blots were exposed to X-ray film (Kodak) for varying times (1 minute to 8 minutes) and developed.

Electroporation of probe:target DNA hybrids into metabolically active E. coli cells: After purification of targeted complexes, 40 µl of electro-competent RecA(+) and/or RecA(−) E. coli (Dower et al., 1988) was added to 30-200 ng of the targeted complexes in a chilled microfuge tube. The RecA(+) cells were BB4 (Stratagene) and the RecA(−) cells were XL1-Blue (Stratagene). The mixture was incubated on ice for 1 minute. This mixture was then transferred to a chilled 0.1 cm gap electroporation cuvette (Bio-Rad) and electroporated under the following conditions: 1.3 V, 200 ohms, 25 µF on a Bio-Rad Gene Pulser. The time constant ranged from 4.5–4.7 msec. Immediately afterwards,. 1 mL of SOC media (Sambrook, et al., 1989) was added and the mixture was transferred into a 10 mL culture tube. After all the electroporation groups were finished, the tubes were shaken at 225 rpm at 37° C. for 1 hour. Appropriate amounts were plated onto LB agar plates which already contained 100 µg/ml ampicillin (Sigma), 20 µg/ml X-gal (GIBCO-BRL), and 48 µg/ml IPTG (GIBCO-BRL), and incubated at 37°C. overnight.

Screening for homologous DNA recombination in LacZ: After overnight incubation (approximately 16 hrs.), colonies were counted to determine electroporation efficiency and scored for any blue colonies in plates. Blue colonies were scored if they resembled blue colonies displayed by the control plasmid pBluescript II SK(−), which is able to undergo alpha-complementation and produce blue colonies. Blue colonies were serially propagated on AIX plates at least twice to confirm recombinant stability as monitored by consistency of color. When the colonial streaks displayed a homogeneous color, plasmids were isolated by a mini-prep and digested with EcoRI, XhoI, and PvuII to confirm homologous recombination of the plasmid at the DNA level. EcoRI and XhoI sites are restored if homologous recombination has occurred. PvuII restriction sites which flank the LacZ region contains the 59 base pair deletion; if recombination has occurred, this fragment will be significantly larger than fragments lacking the 59 base pairs after digestion with PvuII.

RecA mediated cssDNA targeting to negatively supercoiled dsDNA substrates containing deletions: Stable probe:target hybrids formed in the RecA mediated targeting reaction between the biotinylated RecA coated cssDNA probes IP290 and the negatively supercoiled Form I dsDNA targets pRD.59, which contain a 59 base pair deletion respective to the cssDNA probe, were monitored by chemiluminescent detection of biotinylated hybrids (FIG. 11). The presence of a sizable region of non-homologous nucleotide sequences (59 bp) in the cssDNA probe IP290 does not significantly affect the ability of the RecA coated cssDNA probe IP290 to form stable probe:target hybrids with pRD.59 in comparison to completely homologous dsDNA pRD.0 (FIG. 11, lane 3 and 6). In each reaction, under these conditions, the presence of the RecA protein was absolutely required for hybrid detection (FIG. 11, lane 2 and 5).

Probe:target DNA hybrids formed when the RecA coated biotinylated cssDNA probe IP290 is hybridized to the completely homologous dsDNA target pRD.0 differ from probe:target hybrids formed when the same cssDNA probe is hybridized to the dsDNA target pRD.59 containing a 59 base pair deletion with respect to IP290. While more than 90% of both the dsDNA targets exist as negatively supercoiled Form I DNA, when hybrids formed between pRD.0 and RecA coated cssDNA probe IP290 are deproteinized, the probe:target hybrids migrate to a position that is similar to the migration of Form II, relaxed circular dsDNA, in 1% agarose gel in 1× TAE buffer (FIG. 11, lane 3 and 6), and there was no evidence of probe:target hybrids that co-migrate to Form I DNA on a 1% agarose gel (FIG. 11, lane 3). This probe:target hybrid is referred to as a relaxed Form I* hybrid or a rI* hybrid because the hybrid has the same elelctrophoretic mobility as relaxed circular DNA. In contrast, when the RecA coated cssDNA probe IP290 was hybridized to the dsDNA target pRD.59, which as a 59 bp deletion with respect to the probe, two different probe:target hybrids were apparent. One has an electrophoretic mobility comparable to that of Form I supercoiled dsDNA (FIG. 11, lane 6) while the other migrates to the same position as the rI* hybrid. These two forms appear to be present in equal amounts as indicated by the signal from chemiluminescent DNA detection. This probe:target hybrid is referred to as a Form I* hybrid or I* hybrid, differentiating it from Form I DNA because it is targeted with RecA coated cssDNA probe. In order to exclude the possibility that it is the structure of the dsDNA target that creates the formation of two major probe:target hybrid products, the cssDNA probe DP231 was hybridized to pRD.59. The cssDNA probe DP231 is completely homologous to the mutant region of the LacZ gene in pRD.59. The only probe:target hybrid detected has the electrophoretic mobility of Form II dsDNA, the rI* hybrid (FIG. 11, lane 8). In addition, when the cssDNA probe CP443, which is completely homologous to a region outside of the 59 base pair deletion, was hybridized to pRD.59, only the rI* hybrid product was detected (FIG. 11, lane 10). Thus, when the RecA coated cssDNA probes are targeted to homologous sequences, only the rI* hybrid is present, but when it is targeted to homologous sequences with relatively short heterologies, two forms of hybrids, rI* and I* hybrids are formed in apparently equivalent amounts.

Recombinogenicity of probe:target DNA hybrids: To study the biological consequences of the probe:target hybrid structures, we assayed for putative homologous recombination events in E. coli by the electroporation assay (described in FIG. 10).

FIG. 12 shows the percentage of potential recombinant blue colonies formed when IP290 probe:pRD.59 target hybrids were electroporated into RecA+ and RecA− cells. Blue colonies only arose when deproteinized hybrids formed with pRD.59 and cssDNA probe IP290 are introduced into RecA+ E. coli cells. Control experiments performed with cssDNA probes homologous to the mutant LacZ region of pRD.59 (DP231) and homologous to a region outside of the LacZ gene (CP443) did not yield any blue colonies. (FIG. 12). In addition, when all of these hybrids were transformed into RecA(−) hosts, no blue colonies were produced from any type of hybrid, indicating the the recombinogenic effect is also dependent on endogenous RecA protein produced in the cell. Thus only the cssDNA probe containing the 59 base pair correction produces recombinogenic clones in bacterial host cells that are RecA(+).

When potential homologous recombinant blue colonies were propagated by streaking out on AIX plates, only 50% of the colonies were blue. When a blue colony from the first streak was propagated by recombinant streaking, the colonies remained stably blue over several generations. If plasmid DNA was isolated from third generation propagations and then transformed into RecA(-) cells, this resulted in blue colonies which remained stably blue on continued propagation. Of the potential recombinants that have been rigorously screened by restriction enzyme digestion, at least 67% of the plasmids recovered from blue colonies are true homologous recombinants. This was deterimined by the restoration of EcoRI and XhoI restriction sites, and a PvuII digest of the DNA shows a fragment that migrates at a higher molecular weight than fragments which are missing the 59 base pair region.

This is consistent with the view that only one strand is exchanged in the these hybrids to form heteroduplex targets and that upon replication one strand will produce a plasmid that contains the 59 base pair correction while the other does produces the 1 5 mutant pRD59 plasmid.

As outlined in Example 5, we show that the recombinogenicity with probe:target hybrids of cssDNA probes and dsDNA targets containing deletions is associated with the re-annealing of regions of cssDNA probe that can not hybridize to dsDNA targets, by creating internal homology clamps (FIG. 13).

EXAMPLES 5

Enhanced Homologous Recombination with Targets Containing Insertions and Deletions Through the Formation of Internal Homology Clamps An in vitro DNA hybridization reaction that allows the pairing of RecA-coated complementary single-stranded (css) DNA probes to homologous regions in linear duplex target DNA has been used to study the effects of heterologies within the regions of homology between the probes and target DNA. In cssDNA targeting reactions catalysed by RecA protein, cssDNA probes are kinetically trapped within the duplex DNA target at homologous sites and form a highly stable four-stranded DNA hybrid structure. After removal of RecA protein, this homologous recombination reaction can be trapped at the DNA pairing step. The effect of defined heterologous insertions or deletions in linear duplex targets on the pairing of RecA-coated cssDNA probes was determined for heterologies ranging from 4 to 967 bp. We demonstrate that small deletions and insertions up to 10% of the total cssDNA probe lengths, ranging from 215–1246 bp do not significantly affect DNA pairing. Furthermore both insertions and deletions of the same size in the cssDNA probe have the same effect on DNA pairing. Moreover, large deletions, up to 967 bp, can be tolerated in deproteinized hybrids form with a RecA-coated 1.2 kb cssDNA probe. The stability of these hybrids with heterologous sequences within the homologous paired region is due to the re-annealing of the cssDNA probes to each other within the DNA hybrid producing a novel four-stranded heteroduplex DNA intermediate that contains a novel internal base-paired homology clamp.

Preparation of ds target substrates: A series of plasmid DNA targets with defined deletions were constructed by linearization of the plasmid vector pBluescript IISK(-) (Stratagene) at a unique EcoRI restriction site in the polylinker region following digestion with mung bean exonuclease (Boehringer-Mannheim), DNA ligation, and subsequent transformation into XL1-Blue E. coli (Stratagene) by standard methods. The resulting clones were sequenced using Sanger dideoxy sequencing methods (Sequenase Kit version 2, USB) to determine the extent of deletion. A series of plasmids with deletions ranging from 4 to 967 bp were prepared and named for the extent of size of the deletion (see FIG. 15). The size of the parent plasmid, pBluescript IISK (-), referred to as pRD.0 in this study, is 2960 bp. Plasmid DNA was prepared by a modified alkaline lysis procedure with anion-exchange purification (Qiagen). The DNA was further purified by phenol-chloroform-isoamyl alcohol extraction (24:25:1) (SIGMA) and ethanol precipitation, and then resuspended in TE (10 mM Tris HCl, pH7.5, 1 mM EDTA).buffer. These preparations contained greater than 90% Form I DNA. Preparations of linearized Form III DNA were made by digestion of the plasmids at a unique ScaI restriction site outside the polylinker, followed by phenol-chloroform-isoamyl alcohol extraction (SIGMA), chloroform extraction, ethanol precipitation, and resuspension in TE buffer.

Preparation of cssDNA probes: Biotin-labeled probes homologous to pRD.0 were synthesized by PCR with incorporation of biotin-14-dATP using previously described methods where the molar ratio of unlabelled dATP to biotin-labelled dATP was 3:1 (Griffin & Griffin, 1995). Primer pairs flanking the polylinker region of pRD.0 or analogous plasmids with a deletion were chosen to produce PCR fragments which span the deletion in the target plasmids. In addition a control PCR fragment (CP443) primer pair flanking sequences outside the polylinker was selected for production of a probe homologous to all clones in the plasmid series. The oligonucleotide products were purified by membrane ultrafiltration using Microcon 100 filters (Amicon).

Targeting of cssDNA probes to dsDNA targets in solution: cssDNA targeting was performed essentially as described in Sena & Zarling (1993), with the exception that cssDNA probes were synthesized and labeled by PCR in the presence of biotin-14-dATP (GIBCO/BRL), as indicated above. In each reaction 70 ng of biotin-labelled RecA-coated cssDNA probe was reacted with 1 μg of Sca1-digested target DNA, resulting in cssDNA probe:target ratios of 1:1 (for 215 bp cssDNA probes) to 1:5 (for 1246 bp cssDNA probes). The products of the targeting reactions were deproteinized by treatment with SDS (1.2% final concentration) or phenol:chloroform: isoamyl alcohol (24:25:1) and chloroform extraction and then separated by electrophoresis on 1% agarose gels in TAE buffer. The gels were run at 2V/cm at room temperature in the absence of ethidium bromide for 20 hours. After electrophoresis, gels were stained in 1 μg/ml ethidium bromide for 15 min. The DNA was transferred under non-denaturing conditions (10× SSC) onto nylon membranes (Tropix) and cross-linked using a Stratalinker (Stratagene) on the auto-crosslink setting. The extents of biotinylated cssDNA probe:target hybrid formation was measured by quantitating the amount of biotin-labeled probe DNA that co-migrates with ds DNA target DNA following electrophoretic separation of these biotinylated probe:target hybrid products from free unhybridized probe DNA. The amount of biotinylated probe DNA in probe:target complexes was visualized with a chemiluminescent substrate conjugated to streptavidin (CDP-STAR) (Tropix) after exposure to XAR-5 film (Kodak). The levels of exposure were analyzed by densitometry and quantitated using the software package, NIH Image.

In each case the relative level of hybrid formation with heterologous targets was expressed as a percentage of the level of hybrid formation of a standardized reactions with a completely homologous probe and target. These values were normalized to the level of hybrid formation that occured with control probe CP443 which hybridizes to all of the plasmid targets in a region away from the heterology. The data generally represent averages of at least three separate measurements from three independent targeting reactions.

Nomenclature and Assay for RecA-mediated pairing of cssDNA probes to dsDNA targets.: To investigate the effects of heterologous insertions and deletions on homologous pairing of cssDNA probes to double-stranded linear plasmid DNA, we employed a modification of an in vitro DNA targeting assay described in Sena and Zarling (1993). The target DNAs used in this study are a series of plasmid DNA constructs that contain defined deletions at the unique EcoRI site in pRD.0 (pbluescriptIISK(+), Stratagene FIG. 14A). Plasmid targets (pRD.4–pRD.967) are named for the size of deletion in bp at the EcoR1 site. CssDNA probes were made and labelled with biotin-14-dATP by PCR using primers which symetrically flank the deleted region of plasmids in the pRD series. CssDNA probes made from pRD.0 that were targeted to plasmids containing deletions are called insertion probes and named for the length of the probe in bp. For example, IP290 is a 290 bp cssDNA probe that contains an insertion with respect to a target containing a deletion, but is completely homologous to pRD.0. A cssDNA probe made from pRD.59 and targeted to pRD.0 is called DP231, since it contains a deletion with respect to pRD.0, but is completely homologous to pRD.59.

After the hybridization of RecA-coated cssDNA probes with dsDNA targets, the reactions products were separated by agarose gel electrophoresis. The extent of formation of stable deproteinized cssDNA probe:target hybrid was measured by the quantitation of the amount of biotinylated cssDNA probes that co-migrated with the dsDNA targets. In each case the level of probe:target formation between a totally homologous probe and target was normalized to 100%. Previous studies have shown that efficient cssDNA targeting is completely dependent on RecA protein, the nucleotide co-factor, specific to homologous DNA targets and that formation of deproteinized stable probe:target hybrids also requires both cssDNA strands (Sena and Zarling, 1993, Revet et al, 1993). Furthermore we targeted ScaI-digested pRD.0 with two synthetic RecA-coated 121-mer cssDNA oligonucleotides homologous to the region symetrically spanning the EcoR1 site in pRD.0 and demonstrated that both cssDNA strands are required for stable hybrid formation with linearized pRD.0 targets (data not shown).

Stable cssDNA probe:target hybrids are formed in linear dsDNA targets with deletions at internal sites. To determine if a target DNA deletion affects the reaction kinetics of RecA-mediated cssDNA pairing to linear DNA targets, we measured the relative amount of deproteinized cssDNA probe:target hybrid formation over time in reactions using cssDNA probe IP290 with either a completely homologous linear target, pRD.0 or a target carrying a 59 bp deletion, pRD.59. Probe IP290 symetrically spans the 59 bp deletion in pRD.59. FIG. 15B shows that in steady state hybrid reactions, the maximum level of stable hybrid formation when RecA-coated IP290 is targeted to pRD.59 is 62% of the steady state level obtained with the fully homologous target pRD.0. Furthermore steady state levels of hybrid formation occurs within 45 minutes with fully homologous pRD.0 targets, but requires 2 hours for pRD.59 targets. Thus, in all subsequent experiments RecA-coated probes were hybridized for 2 hours at 37° C. with the linear target DNAs.

The effect of duplex DNA target deletions on the formation of deproteinized cssDNA probe: target hybrids was determined by hybridizing RecA coated cssDNA probes which span the deleted regions in pRD.4–pRD.298 on DNA targets linearized by ScaI (FIG. 15A). The relative amount of biotinylated probe:target hybrids formed with each of these targets was compared with the amount of cssDNA probe target hybrids formed with pRD.0. These values were normalized to the level of hybrid formation obtained with the control probe, CP443, which is homologous to a region away from the deleted regions or pRD.0 and thus, is completely homologous to all target DNA substrates used in this study.

Our initial studies tested the effect of small target deletions on targeting efficiency using either cssDNA probes IP527 or IP407 (FIG. 15B and 15C). Because the 5'-and 3'-termini of both of these cssDNA probes are approximately symmetric with respect to the 4 to 59 bp deletions, the differences in the efficiency of hybrid formation are not due to the effects of the position of the deletion with respect to the probe in relation to probe ends. As expected, in experiments using either the IP527 or IP407 we observed a decrease in the level of hybrid formation with an increase deletion size. These data also show that relatively small deletions ($\leq 25$ bp) in the target do not dramatically affect the overall targeting efficiency of cssDNA probes to linear targets and that the deletions have relatively the same effect on the hybridization on either IP527 and IP407. However when the size of the deletion is increased to 59 bp (11% of the length of IP527), the relative targeting efficiency of probes IP527 and IP407 drops to 61% and 33%, respectively. Furthermore the amount of the difference between the targeting efficiency mediated by these probes continues to increase linearly as the size of the deletion increases (FIG. 15D). This indicates that when the size of the deletion is>10% of the length of the probe the efficiency of RecA-mediated DNA targeting is governed by the amount of homology between the cssDNA probe and target, while deletions<10% of the length of the probe are well tolerated for any length of cssDNA probe. Similar effects are observed with smaller cssDNA probes IP452, IP290 (data not shown) and IP215 (FIG. 16).

Heterologous Insertions and Deletions are similarly tolerated in the hybridization of cssDNA probes to linear dsDNA targets. Other studies by Bianchi and Radding (Cell 35:511–520 (1983)) in which RecA-coated circular ssDNA was hybridized to linear duplex targets demonstrated that heterologous inserts in the ssDNA were tolerated somewhat better than when the insert was in the dsDNA, presumably because the inserts in ssDNA could be folded out of the way. In contrast, Morel et al (J. Biol. Chem. 269:19830 (1994)) used somewhat similar substrates and demonstrated that RecA-mediated strand exchange could bypass heterologies with equal efficiency whether the insert was in the ssDNA or dsDNA. Since the formation of stable cssDNA:probe target hybrids with internal sequences in linear dsDNA requires two cssDNA probe strands, we compared the effects of insertions in the cssDNA probe with having the same sized insertion in the dsDNA to determine how these internal heterologies maybe accommodated within a four strand containing double-D-loop DNA structure.

In these studies we compared the effects of 4 to 59 bp insertions in either the dsDNA target or cssDNA probe (deletion in target) using cssDNA probes ranging in size from 156 bp to 215 bp. We used this smaller cssDNA probe to maximize the effects of the insertion or deletion of these sizes. We prepared cssDNA probe IP215 from pRD.0 using PCR and targeted pRD.0, pRD.4, pRD.25, and pRD.59 to measure the effects of insertions in cssDNA probes (target DNA deletion). Then using the same PCR primer set, we prepared cssDNA probes from templates pRD.0, pRD.4, pRD.25, and pRD.59 and then targeted pRD.0 to measure the effects of deletions in cssDNA (target DNA insertion). FIG. 16 shows that both deletions and insertions of the same size have exactly the same effect on RecA-mediated css-DNA targeting and are equally tolerated and stable.

Large Deletions in linear DNA are tolerated in cssDNA probe:target hybrids with linear dsDNA. To further define the extents of heterology that can be tolerated during css-DNA hybridization, we studied the effect of very large deletions, up to 448–967 bp on the targeting efficiency using a 1246 bp cssDNA probe (IP1246) (FIG. 17A). With target deletions in range of 500 bp (approx. 50% of the cssDNA probe length) there is only a slight reduction in the targeting efficiency achieved with this probe (80%), surprisingly the IP1246 can hybridize target DNA molecules bearing deletions up to 967 bp at a detectable efficiency (27%). When IP1246 is targeted to pRD.967, there are a total of 279 bp of homology between the cssDNA probe and target, with 147 bp5' to the 967 bp insert and 132 bp 3' to the insert (FIG. 17B). In order to account for such a high level of targeting efficiency with such a large deletion, we predict that the 967 bp insert in the two in the cssDNA probe strands, which are homologous to each other, may interact with each other to stabilize this hybrid.

Furthermore when using a large cssDNA probes of 1246 bp we can observe a visible shift the migration of the cssDNA probe:target hybrid in comparison to the linear dsDNA target. The positions of the migration of the of the 3.0 kb Sca1-digested ds DNA marker are shown in FIG. 17A. Note the cssDNA probe:target hybrids formed with IP1248 migrate slower than each of the Sca1-digested targets, but that cssDNA probe:target hybrids formed with CP443, a smaller probe migrate closer the positions of the formIII markers. The presence of this labelled slower-migrating species provides further evidence for the existence of the multi-stranded DNA hybrids.

EcoR1 Restriction Endonucleases cut duplex DNA in either homologous or heterologous cssDNA probe:target hybrids. To further characterize cssDNA probe:target hybrids formed with heterologous DNA targets, circular plasmids pRD.0 and pRD.59 were hybridized with biotin-labelled probe IP290 and then deproteinized and digested with EcoRI. While plasmid pRD.0 contains a unique EcoR1 site in the region of homology between IP290 and pRD.0, the EcoR1 site is deleted in pRD.59 (FIG. 14A). Digestion of cssDNA probe:target hybrids with EcoR1 indicates the restoration of Watson-Crick pairing to form a fully duplex EcoR1 recognition site. FIG. 18 shows both the ethidium bromide stained gel of the hybrid product of the targeting reaction (FIGS. 18A and 18B) and the corresponding autoradiograph that shows the electrophoretic migration of the biotin-labelled probes (FIGS. 18C and 18D). These data show that when RecA-coated IP290 is hybridized to the fully homologous pRD.0 plasmid all of the probe:target hybrids migrate to position of fully relaxed DNA (FIGS. 18 A and C, Lane 1). Furthermore, upon digestion with EcoR1 cssDNA:probe target hybrids can be completely cut as shown in FIGS. 18 A and C, Lane 2. When similar reactions are performed with uncut pRD.59 targets, we found that not all of the probe:target hybrids are relaxed as with pRD.0 targets, as judged by the appearance of two bands corresponding to a pRD59 I* hybrid, where the hybrids co-migrate with FormI supercoiled DNA and a pRD59 rI* hybrid that migrates with relaxed targets (FIGS. 18B and D, Lane 3). When these hybrids are digested with EcoRI we find that the pRD59 rI* hybrid is more susceptible to EcoRI cleavage than the pRD59 rI* hybrid (FIGS. 18B and D, Lane 4). This shows that there is a restoration of the EcoRI site in relaxed targets, but not in the non-relaxed I* hybrid. Since pRD59 targets do not contain an EcoRI site, cleavage by EcoRI can only be explained by re-annealing of cssDNA probe IP290 within the IP290 probe:target pRD59 hybrid.

To further characterize the structural differences between pRD59 rI* hybrids and pRD59 I* hybrids, cssDNA probe-:target hybrids were formed between IP290 and pRD59, deproteinized and thermally melted for 5 mins at 37° C., 45° C., 55° C., and 65° C., respectively. FIG. 19 shows that pRD59 rI* hybrids are more thermostable than pRD59 I* hybrids. For both types of hybrids probe:target hybrids are completely dissociated after heating to 95° C. (data not shown). Taken together these data support the structures of our models for hybrids (FIG. 13).

EXAMPLE 6

Homologous Recombination Targeting in Fertilized Mouse Zygotes

Ornithine transcarbamylase (OTC) is a mitochondrial matrix enzyme that catalyzes the synthesis of citrulline from ornithine and carbamylphosphate in the second step of the mammalian urea cycle. OTC deficiency in humans is the most common and severe defect of the urea cycle disorders. OTC is an X-linked gene that is primarily expressed in the liver and to a lesser extent in the small intestine. Affected males develop hyperammonemia, acidosis, orotic aciduria, coma and death occurs in up to 75% of affected males, regardless of intervention. Two allelic mutations at the OTC locus are known in mice: spf and spf-ash, (sparse fur-abnormal skin and hair). In addition to hyperammonemia and orotic aciduria spf-ash mice can be readily identified by the abnormal skin and hair phenotype. The spf-ash mutation is a single-base substitution at the end of exon 4 that results in alternative intron-exon splicing to produce of an aberrant non-functional elongated pre-mRNA. Because of the clinical importance of OTC defects in humans, there is an intensive effort to develop in vivo methods to correct the enzymatic defect in the spf-ash mouse model.

We used the spf-ash murine model of OTC deficiency to test the ability of RecA-coated complementary single-stranded DNA (css) OTC probes to target and correct a single-base substitution mutation in fertilized mouse zygotes. A 230 bp RecA-coated cssDNA probe amplified from the normal mouse OTC gene was microinjected into embryos made from the cross of B6C3H homozygous female spf-ash and normal B6D2F1J males. After re-implantation of 75 embryos that were microinjected with RecA-coated cssDNA into CD1 foster mothers, 25 developmentally normal pups (17 female and 8 male) were produced. Sequence analysis of the genomic DNA isolated from tails of the male pups show that in $3/8$ males a homologous recombination event occured that produced mosaic animals at the spf-ash site in exon4 of the mouse OTC gene. Subsequent breeding of the three the mosaic male founder mice with normal females demonstrated the gene corrected OTC allele was transmitted to the sperm germline from one of these three mosaic homologous recombinant mice, as determined by sequence analysis of the genomic DNA and transmission of phenotypic correction to F1 mice. These studies illustrate the utility of cssDNA probes to mediate high frequency homologous recombination in fertilized mouse zygotes to create subtle genetic modifications at a desired target site in the chromosome.

Preparation of RecA-coated probe: A 230 bp fragment from the normal mouse OTC gene was amplified by PCR with primers M9 and M8 from pTAOTC (FIG. 20). The PCR fragment was purified on Microcon-100 columns (Amicon) and then extensively dialyzed in ddH$_2$O. The M9-M8 amplicon was denatured by heating the fragments to 98° C. and then coated with RecA protein (Boehringer-Mannheim) at a ratio 3 nucleotides/ protein monomer. The final concentration of RecA-coated DNA in coating buffer (5 mM TrisOAc, pH 7.5, 0.5 mM DTT, 10 mM MgOAc, 1.22 mM ATPyS, 5.5 $\mu$M RecA) was 5 ng/ $\mu$L. RecA-coated filaments were made on the day of microinjection and then stored on ice until use.

Transgenic Mice: Five superovulated B6C3H (spf-ash/spf-ash) 5–7 week old females (Jackson Labs) were mated with five B6D2F1males (Jackson Labs). Approximately 80–100 embryos were isolated from oviducts as described in Hogan et al. (1988). The female pronucleus of fertilized embryos were microinjected with 2 pl of RecA-coated M9-M8 cssDNA probe (5 ng/$\mu$L). Approximately 75 embryos survived the microinjection procedure and were then re-implanted into a total of three CD1 pseudopregnant foster mothers (Charles River). Pseudopregnant females were produced by mating foster mothers with vasectomized CD1 males (Charles River).

DNA Analysis: Tail biopsies were taken from all founder mice after weaning at and ear-tagging at three weeks of age. Genomic DNA was isolated from tail biopsies using standard procedures. To obtain the sequence of the DNA at the OTC locus, genomic DNA was amplified with PCR using primers M10-M11 or M54-M11 that flank the cssDNA probe sequence to generate a 250 bp or 314 bp amplicon (FIG. 20). PCR fragments were sequenced manually using the Cyclist Exo- Kit (Stratagene), automatically on Applied Biosystems Model 373A sequencer, or by a MALDI-TOF mass spectrometry system (GeneTrace Systems, Menlo Park, Calif.)

Fertilized zygotes microinjected with RecA-coated DNA are viable. Plasmid pTAOTC1 carries a 250 bp segment of exon4 and surrounding intron sequences from the normal mouse OTC gene. A 230 bp cssDNA probe OTC1 was prepared by PCR amplification of pTAOTC1 with primers M9 and M8. cssDNA probe OTC1 was denatured and coated with RecA protein as described herein.

Homozygous spf-ash/spf-ash female and hemizygous (spf-ash/y) males can be phenotypically identified by the appearance of sparse fur and wrinkled skin early in development. A cross between homozygous spf-ash/spf-ash B6C3H females and normal B6D2F1 males yields heterozygous phenotypically normal females and hemizygous males with sparse fur and wrinkled skin. The RecA-coated cssDNA OTC probe was microinjected into embryos made from the cross of B6C3H homozygous female spf-ash and normal males. The female pronucleus of approximately 80–90 fertilized zygotes was microinjected with 2 pl of a 5ng/$\mu$L solution of RecA-coated cssDNA probe OTC1. Of these 75 embryos survived the microinjection procedure. To demonstrate that embryos that have been microinjected with RecA-coated cssDNA are viable, the embryos were re-implanted into three pseudopregnant CD1 foster mothers. From this, 25 developmentally normal pups (17 female and 8 male) were produced. All of the female mice were phenotypically normal. The eight male mice (mouse #7, 14,16, 17,22,23,24, and 25) were all affected with sparse-fur and wrinkled skin to various degrees.

RecA-coated cssDNA probe OTC1 recombines with the homologous chromosomal copy of the OTC gene in fertilized mouse zygotes. To determine the genotypes of the 25 founder mice produced from microinjected embryos, genomic DNA was isolated from tail biopsies containing skin, blood and bone cells. Genomic DNA was amplified with either the primer set M10-M11 or M54-M11 to produce either a 250 bp or 314 bp amplicon. By using these primer sets that flank the OTC1 probe, the DNA amplicon represents DNA from the endogenous OTC gene. PCR fragments from all of the eight mice and several female mice were sequenced to determine the base sequence at the spf-ash locus to determine if a normal allele (G) or a mutant allele (A) was present in the genomic DNA. FIG. 21 shows sequencing gels of representative reactions. The leftmost panel shows the sequence of the homozygous spf-ash females that donated the eggs to produce the fertilized zygotes where only the mutant base A is present at the spf-ash locus, as expected. The sequence of female mouse #8 that should be heterozygous shows the presence of equal amounts of the bases G and A as expected. Male mice 7, 14 (shown), 23, 24, and 25 all showed only the mutant base A at the spf-ash locus, however male mice 16, 17, and 22 (shown) displayed both G (normal) and A (mutant) at the spf-ash locus.

To eliminate the possibility of PCR artifacts during PCR cycle sequencing the base compositions of the samples was independently confirmed by mass spectrometry sequencing (GeneTrace, Menlo Park). The relative amounts of the A:G base composition at the spf-ash locus was also quantified and determined to be 70:30 for samples from mouse #16 and #17 and 10:90 for mouse#22. Since OTC is an X-linked gene the presence of mixed bases in male mice is likely the result of the mosaic animals produced of a mixture of mutant and gene corrected embryonic cells.

Germline transmission of the gene corrected OTC allele. To determine if the gene corrected allele in the mosaic male founder mice 16, 17, and 22 could be passed through to the germline, these mice and a control hemizygous mutant male #7 were bred with normal B6D2F1 females. In this cross if the male donates a mutant spf-ash X chromosome the resulting female progeny will be heterozygous spf-ash mutants. However if the male donates a normal (gene corrected) X chromosome the female progeny will be homozygous normal. In both cases the resulting F1 females will be phenotypically normal. The results of these crosses are summarized in FIG. 22. In the control cross of hemizygous mutant male#7 with B6D2F1 females, all 14 female progeny were heterozygous, as expected. In test crosses of mosaic male mouse #17 and #22 with normal females all resulting female progeny (5 and 9, respectively) were heterozygous. However in the cross with mosaic male mouse #16, one out nine total female progeny was a homozygous normal female (mouse #213) as determined mass spectrometry sequencing (GeneTrace, Menlo Park), demonstrating the gene corrected allele in founder mouse #16 was transmitted through the germline.

To further verify that F1 mouse #213 was in fact a germline-transmitted gene corrected homozygous normal female, this and a control heterozygous spf-ash/X mouse were bred with normal males. In the control cross B with the heterozygous female, 50% of the resulting male F2 progeny should be mutant spf-ash/y hemizygotes that can be easily determined by the visualization of sparse-fur and wrinkled skin. Of the 38 progeny produced in this control cross B, 14 were male, and of these, 8 were phenotypically normal and 6 were mutant as determined by the presence of wrinkled skin and abnormal fur. In the test cross with F1 mouse #213, of the 35 progeny produced in this cross, all eleven of the male progeny were phenotypically normal, clearly showing the genotyping of F1 mouse #213 as a germline transmitted gene corrected homozygous normal female.

As another test to determine if the normal gene corrected allele in mouse #16 could be transmitted through the germline, mouse #16 was mated with homozygous (spf-ash/spf-ash) mutant females. In this cross if mouse #16 does not transmit a normal allele, the resultant progeny will either be hemizygous (spf-ash/Y) mutant males or homozygous (spf-ash/spf-ash) mutant females, both of which are phenotypically mutant. However if the mouse allele is transmitted through the germline, heterozygous (spf-ash/+) females that are phenotypically normal will be produced. When mouse #16 was bred with homozygous (spf-ash/spf-ash) mutant females, two litters were produced that consisted of a total 5 hemizygous (spf-ash/Y) mutant males, 7 homozygous (spf-ash/spf-ash) mutant females, and 1 phenotypically normal female (mouse #1014). Pictures of representative mice from these crosses are shown in FIG. 23. The production of the phenotypically normal female mouse provides compelling genetic evidence that mouse#16 contains a normal gene corrected OTC allele that is germline transmissable.

Although the present invention has been described in some detail by way of illustration for purposes of clarity of understanding, it will be apparent that certain changes and modifications may be practiced within the scope of the claims.

We claim:

1. A method for targeting and altering, by homologous recombination, a pre-selected target nucleic acid sequence in an extrachromosomal sequence of a procaryotic cell, said method comprising:
   a) adding to said extrachromosomal sequence at least one recombinase and at least two single-stranded targeting polynucleotides each of which are substantially complementary to each other and comprise a homology clamp that substantially corresponds to or is substantially complementary to a preselected target nucleic acid sequence to form an altered extrachromosomal sequence; and
   b) introducing said altered sequence into a procaryotic cell.

2. A method according to claim 1 further comprising identifying a procaryotic cell having a targeted nucleic acid sequence modification at said preselected target nucleic acid sequence.

3. A method according to claim 1 wherein said targeting polynucleotides are coated with said recombinase.

4. A method according to claim 1, wherein said recombinase is a species of prokaryotic recombinase.

5. A method according to claim 1, wherein said recombinase is a species of eukaryotic recombinase.

6. A method according to claim 1, wherein at least one of said targeting polynucleotides is conjugated to a cell-uptake component.

7. A method according to claim 1, wherein at least one of said targeting polynucleotides is conjugated to a cell-uptake component and to a recombinase, forming a cell targeting complex.

8. A method according to claim 1, wherein said altered extrachromosomal sequence comprises a deletion of at least one nucleotide.

9. A method according to claim 1, wherein said altered extrachromosomal sequence comprises the addition of at least one nucleotide.

10. A method according to claim 1, wherein said altered extrachromosomal sequence comprises the substitution of at least one nucleotide.

11. A method according to claim 1, wherein the recombinase and the targeting polynucleotides are added simultaneously.

12. A method according to claim 1, wherein each targeting polynucleotide comprises a homology clamp that is less than 1200 nucleotides long.

13. A method according to claim 1, wherein the targeting polynucleotides are less than 1200 nucleotides long.

14. A method according to claim 1, wherein said altered extrachromosomal sequence adds a gene to said extrachromosomal sequence.

15. A method according to claim 1, wherein at least one of said targeting polynucleotides further comprises a chemical substituent.

16. A method according to claim 4, wherein said prokaryotic recombinase is a species of prokaryotic recA protein.

17. A method according to claim 5, wherein said recombinase is a Rad51 recombinase.

18. A method according to claim 5, wherein said eukaryotic recombinase is a complex of recombinase proteins.

19. A method according to claim 6 wherein said cell-uptake component is conjugated to at least one of said targeting polynucleotides by noncovalent binding.

20. A method according to claim 8, wherein said complementary single stranded targeting polynucleotides comprise an internal homology clamp.

21. A method according to claim 10, wherein said altered extrachromosomal sequence comprises a plurality of substitutions.

22. A method according to claim 1, wherein the introducing step is by a method selected from the group consisting of:

microinjection, electroporation, laser poration, biolistics, and liposome mediated transfection.

23. A method according to claim 15, wherein said chemical substituent is covalently attached to said at least one targeting polynucleotide.

24. A method according to claim 16, wherein said recA protein is *E. coli* recA protein.

25. A method according to claim 19, wherein the cell-uptake component comprises a protein-lipid complex.

26. A method of generating a library of variant nucleic acid sequences of a pre-selected target nucleic acid sequence, said method comprising adding to said pre-selected target nucleic acid sequence at least one recombinase and a plurality of pairs of single-stranded targeting polynucleotides which are substantially complementary to each other and each comprising a homology clamp that substantially corresponds to or is substantially complementary to a preselected target nucleic acid sequence, said plurality of pairs comprising a library of mismatches between said targeting polynucleotide and said target nucleic acid sequence, to form a library of variant nucleic acid sequences.

27. A method according to claim 26 further comprising transforming said library of variant nucleic acid sequences into a population of cells.

28. A method according to claim 27 wherein said cells are procaryotic.

29. A method of generating a cellular library comprising variant nucleic acid sequences of a pre-selected target nucleic acid sequence, said method comprising introducing into a population of target cells at least one recombinase and a plurality of pairs of single-stranded targeting polynucleotides which are substantially complementary to each other and each comprising a homology clamp that substantially corresponds to or is substantially complementary to a pre-selected target nucleic acid sequence, said plurality of pairs comprising a library of mismatches between said targeting polynucleotide and said target nucleic acid sequence, to form said cellular library comprising variant nucleic acid sequences.

30. A method according to claim 27 or 29 wherein said cells are eukaryotic.

31. A method of generating a cellular library comprising variant nucleic acid sequences of a pre-selected target nucleic acid sequence, said method comprising:

a) adding to said pre-selected nucleic acid sequence at least one recombinase and a plurality of pairs of single-stranded targeting polynucleotides which are substantially complementary to each other and each comprising a homology clamp that substantially corresponds to or is substantially complementary to said preselected target nucleic acid sequence, said plurality of pairs comprising a library of mismatches between said targeting polynucleotide and said pre-selected target nucleic acid sequence, to form a plurality of altered sequences; and b) introducing said altered sequences into a population of target cells to form said cellular library comprising variant nucleic acid sequences.

32. A method according to claim 31, wherein said target cells are procaryotic.

33. A method according to claim 31, wherein said target cells are eucaryotic.

34. A method according to claim 27, 29 or 31 further comprising screening said population for a desired phenotype.

35. A composition comprising at least one eucaryotic recombinase and a variant library comprising a plurality of pairs of single stranded targeting polynucleotides which are substantially complementary to each other and each comprising a homology clamp that substantially corresponds to or is substantially complementary to a preselected target nucleic acid sequence, said plurality of pairs comprising a library of mismatches between said targeting polynucleotide and said target nucleic acid sequence.

36. A composition according to claim 35 wherein said targeting polynucleotides are coated with said recombinase.

37. A composition according to claim 35 wherein said recombinase is Rad51 recombinase.

38. A composition according to claim 35 wherein said recombinase is a complex of recombinase proteins.

39. A kit comprising the composition of claim 35 and at least one reagent.

* * * * *